US008481737B2

(12) United States Patent
Neves et al.

(10) Patent No.: US 8,481,737 B2
(45) Date of Patent: Jul. 9, 2013

(54) SOLID FORMS OF A CHEMOKINE RECEPTOR ANTAGONIST AND METHODS OF USE THEREOF

(75) Inventors: Carole Neves, Paris (FR); Aurelia Chevalier, Dreux (FR); Pascal Billot, Montreuil (FR)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 13/116,130

(22) Filed: May 26, 2011

(65) Prior Publication Data

US 2012/0065223 A1    Mar. 15, 2012

Related U.S. Application Data

(62) Division of application No. 11/311,574, filed on Dec. 19, 2005, now Pat. No. 7,960,549.

(60) Provisional application No. 60/637,213, filed on Dec. 17, 2004.

(51) Int. Cl.
*C07D 491/044* (2006.01)
*A61K 31/4353* (2006.01)

(52) U.S. Cl.
USPC .............................. 546/80; 546/89; 514/290

(58) Field of Classification Search
USPC ........................ 546/80, 89; 514/290
See application file for complete search history.

(56) References Cited

U.S. PATENT DOCUMENTS

| 6,288,083 B1 | 9/2001 | Luly et al. |
|---|---|---|
| 6,288,084 B1 | 9/2001 | Luly et al. |
| 6,329,385 B1 | 12/2001 | Luly et al. |
| 6,433,165 B1 | 8/2002 | Luly et al. |
| 6,503,926 B2 | 1/2003 | Luly et al. |
| 6,509,346 B2 | 1/2003 | Luly et al. |
| 6,613,905 B1 | 9/2003 | Luly et al. |
| 7,271,176 B2 | 9/2007 | Luly et al. |
| 7,541,365 B2 | 6/2009 | Luly et al. |
| 8,058,287 B2 | 11/2011 | Luly et al. |
| 2002/0119973 A1 | 8/2002 | Luly et al. |
| 2002/0161005 A1 | 10/2002 | Luly et al. |
| 2002/0169155 A1 | 11/2002 | Luly et al. |
| 2003/0045516 A1 | 3/2003 | Luly et al. |
| 2004/0106639 A1 | 6/2004 | Carson et al. |
| 2005/0070549 A1 | 3/2005 | Luly et al. |
| 2005/0288319 A1 | 12/2005 | Carson et al. |
| 2007/0060592 A1 | 3/2007 | Luly et al. |
| 2008/0139602 A1 | 6/2008 | Carson et al. |
| 2009/0281081 A1 | 11/2009 | Luly et al. |
| 2012/0046311 A1 | 2/2012 | Luly et al. |

FOREIGN PATENT DOCUMENTS

| WO | WO 99/37619 A1 | 7/1999 |
|---|---|---|
| WO | WO 99/37651 A1 | 7/1999 |
| WO | WO 00/14086 A1 | 3/2000 |
| WO | WO 00/14089 A1 | 3/2000 |
| WO | WO 01/09119 A2 | 2/2001 |
| WO | WO 01/09137 A1 | 2/2001 |
| WO | WO 01/09138 A2 | 2/2001 |
| WO | WO 03/045942 A2 | 6/2003 |
| WO | WO 2004/043965 A1 | 5/2004 |

OTHER PUBLICATIONS

U.S. Appl. No. 12/436,271, filed May 6, 2009, Carson et al.
International Search Report dated Nov. 23, 2006 in corresponding PCT Application No. PCT/US05/045915.
Bastin, Richard J., et al., "Salt selection and optimisation procedures for pharmaceutical new chemical entities," *Organic Process Research & Development*, vol. 4 (2000) pp. 427-435.
Berge, Stephen M., et al., "Pharmaceutical salts," *Journal of Pharmaceutical Sciences*, vol. 66, No. 1, (Jan. 1977).
Cabri, Walter, et al., "Polymorphisms and patent, market, and legal battles: Cefdinir case study," *Organic Process Research & Development*, vol. 11 (2007) pp. 64-72.

*Primary Examiner* — Rita Desai
(74) *Attorney, Agent, or Firm* — Millennium Pharmaceuticals, Inc

(57) ABSTRACT

The citrate salt of (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol, which may be used in pharmaceutical applications, is disclosed. The crystalline Citrate Salt, including particular single crystal forms and combinations of the single crystalline forms, are also discussed. Mixtures for forming the crystalline salts are discussed. As well, methods of producing the Citrate Salt, and crystalline forms thereof, and using such Citrate Salt, and crystalline forms thereof, in treating diseases associated with aberrant leukocyte recruitment, activation, or recruitment and activation are also discussed.

9 Claims, 30 Drawing Sheets

SOLID FORMS OF A CHEMOKINE RECEPTOR ANTAGONIST AND METHODS OF USE THEREOF

PRIORITY INFORMATION

The present application is a Divisional of U.S. Ser. No. 11/311,574, filed Dec. 19, 2005 now U.S. Pat. No. 7,960,549, which claims priority under 35 U.S.C. §119(e) to U.S. Provisional Application No. 60/637,213, filed Dec. 17, 2004, both entitled "Solid Forms of a Chemokine Receptor Antagonist and Methods of Use Thereof", the entire contents of which are hereby incorporated by reference.

FIELD OF THE INVENTION

The large-scale manufacturing of a pharmaceutical composition poses many challenges to the chemist and chemical engineer. While many of these challenges relate to the handling of large quantities of reagents and control of large-scale reactions, the handling of the final product poses special, challenges linked to the nature of the final active product itself. Not only must the product be prepared in high yield, be stable, and capable of ready isolation, the product must possess properties that are suitable for the types of pharmaceutical preparations in which they are likely to be ultimately used. The stability of the active ingredient of the pharmaceutical preparation must be considered during each step of the manufacturing process, including the synthesis, isolation, bulk storage, pharmaceutical formulation and long-term formulation. Each of these steps may be impacted by various environmental conditions of temperature and humidity.

The pharmaceutically active substance used to prepare the pharmaceutical compositions should be as pure as possible and its stability on long-term storage must be guaranteed under various environmental conditions. This is absolutely essential to prevent the appearance of unintended degradation products in pharmaceutical compositions, which degradation products may be potentially toxic or result simply in reducing the potency of the composition.

A primary concern for the manufacture of large-scale pharmaceutical compounds is that the active substance should have a stable crystalline morphology to ensure consistent processing parameters and pharmaceutical quality. If an unstable crystalline form is used, crystal morphology may change during manufacture and/or storage resulting in quality control problems, and formulation irregularities. Such a change may affect the reproducibility of the manufacturing process and thus lead to final formulations which do not meet the high quality and stringent requirements imposed on formulations of pharmaceutical compositions. In this regard, it should be generally borne in mind that any change to the solid state of a pharmaceutical composition which can improve its physical and chemical stability gives a significant advantage over less stable forms of the same drug.

The present invention relates to forms of a pharmacologically active compound having activity as a chemokine receptor antagonist and having highly preferred properties for use in certain pharmaceutical formulations.

BACKGROUND OF THE INVENTION

Chemoattractant cytokines, Chemoattractant cytokines or chemokines are a family of proinflammatory mediators that are released by a wide variety of cells to promote recruitment and activation of cells such as T and B lymphocytes, eosinophils, basophils, and neutrophils (Luster et al. *New Eng. J. Med*, 1998, 338, 436). The chemokines are related in primary structure and contain four conserved cysteines, which form disulfide bonds. The chemokine family includes the C—X—C chemokines (α-chemokines), and the C—C chemokines (β-chemokines), in which the first two conserved cysteines are separated by an intervening residue, or are adjacent, respectively (Baggiolini, M. and Dahinden, C. A., *Immunology Today*, 1994, 15, 127).

Chemokines exert their biological activity by binding to specific cell-surface receptors belonging to the family of G-protein-coupled seven-transmembrane-domain proteins (Horuk, *Trends Pharm. Sci.* 1994, 15, 159) which are termed "chemokine receptors". On binding their cognate ligands, chemokine receptors then transduce signals important for the development and trafficking of specific leukocyte subsets (Baggiolini, et. al., *Nature* 1994, 15, 365). The chemokines and their cognate receptors have been implicated as being important mediators of inflammatory, and allergic diseases, disorders, and conditions, as well as autoimmune pathologies such as rheumatoid arthritis and atherosclerosis (see, Carter, *Current Opinion in Chemical Biology* 2002, 6, 510; Trivedi et al., *Ann. Reports Med. Chem.* 2000, 35, 191; Saunders et al., *Drug Disc. Today* 1999, 4, 80; and Premack et al., *Nature Medicine*, 1996, 2, 1174). Chemokines and their cognate receptors have also been implicated in the development of cancer and osteolytic bone disorders (see, *Leukemia* 2003, 17, 203; *J. Bone Miner. Res.* 2002, 19, 2065; *J. Cell. Biochem.* 2002, 87, 386; *J. Cell. Physiol.* 2000, 183, 196; *Exp. Hematol.* 2005, 33, 272; *J. Clin. Invest.* 2001, 108, 1833; *Cancer* 2003, 97, 813; *Blood* 2003, 102, 311).

Accordingly, agents that block the interaction of chemokines with their cognate receptors are useful in treating inflammatory, allergic, and autoimmune diseases, disorders, or conditions, and are also useful in the treatment of cancer and osteolytic bone disorders caused by aberrant activation of leukocytes or lymphocytes.

US Patent Application Number US2002/0169155 and International Publication Number WO 03/045942, both entitled "Chemokine Receptor Antagonists and Methods of Use Thereof", disclose compounds that exhibit an inhibitory effect on the chemokine receptor CCR1. These applications additionally disclose methods for the preparation of these compounds, pharmaceutical compositions containing these compounds, and methods for the prophylaxis and therapy of diseases, disorders, or conditions associated with aberrant leukocyte recruitment and/or activation, including but not limited to rheumatoid arthritis and multiple sclerosis.

(S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol (II) is also specifically disclosed:

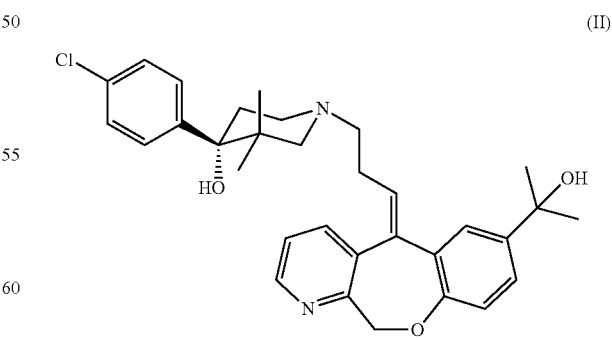

(II)

The structure and synthesis of the free-base amorphous form of this compound is provided in the working examples in US2002/0169155 and WO 03/045942, and only a general discussion of a wide variety of salts is disclosed. These applications do not disclose specific salts or crystalline forms of (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol (II).

When a compound crystallizes from a solution or slurry, it may crystallize, with different spatial lattice arrangements, a property referred to as "polymorphism." Each of the crystal forms is a "polymorph." While polymorphs of a given substance have the same chemical composition, they may differ from each other with respect to one or more physical properties, such as solubility and dissociation, true density, melting point, crystal shape, compaction behavior, flow properties, and/or solid state stability.

As described generally above, the polymorphic behavior of drugs can be of crucial importance in pharmacy and pharmacology. The differences in physical properties exhibited by polymorphs affect practical parameters such as storage stability, compressibility and density (important in formulation and product manufacturing), and dissolution rates (an important factor in determining bio-availability). Differences in stability can result from changes in chemical reactivity (e.g., differential oxidation, such that a dosage form discolors more rapidly when it is one polymorph than when it is another polymorph) or mechanical changes (e.g., tablets crumble on storage as a kinetically favored polymorph converts to thermodynamically more stable polymorph) or both (e.g., tablets of one polymorph are more susceptible to breakdown at high humidity). In addition, the physical properties of the crystal may be important in processing: for example, one polymorph might be more likely to form solvates that cause the solid form to aggregate and increase the difficulty of solid handling, or might be difficult to filter and wash free of impurities (i.e., particle shape and size distribution might be different between one polymorph relative to other).

While drug formulations having improved chemical and physical properties are desired, there is no predictable means for preparing new drug forms (e.g., polymorphs) of existing molecules for such formulations. These new forms would provide consistency in physical properties over a range of environments common to manufacturing and composition usage. In the instant case, no art describes a citrate salt of (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol, and crystalline forms thereof. More particularly, no art describes a citrate salt of (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol, and crystalline forms thereof, that have unexpected properties that are useful for large-scale manufacturing, pharmaceutical formulation, and storage.

SUMMARY OF THE INVENTION

The present invention is directed to the citrate salt of (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol, and crystalline forms thereof. Those forms also have unexpected properties that are useful for large-scale manufacturing, pharmaceutical formulation, and storage. The present invention also provides pharmaceutical compositions comprising said salt, and crystalline forms thereof; methods for the preparation of said citrate salt and crystalline forms thereof; and methods for uses of these salts and crystalline forms thereof for the treatment of a variety of diseases, disorders or conditions as described herein.

The present invention shall be more fully discussed with the aid of the following figures and detailed description below.

DETAILED DESCRIPTION OF THE INVENTION

Figure 1:
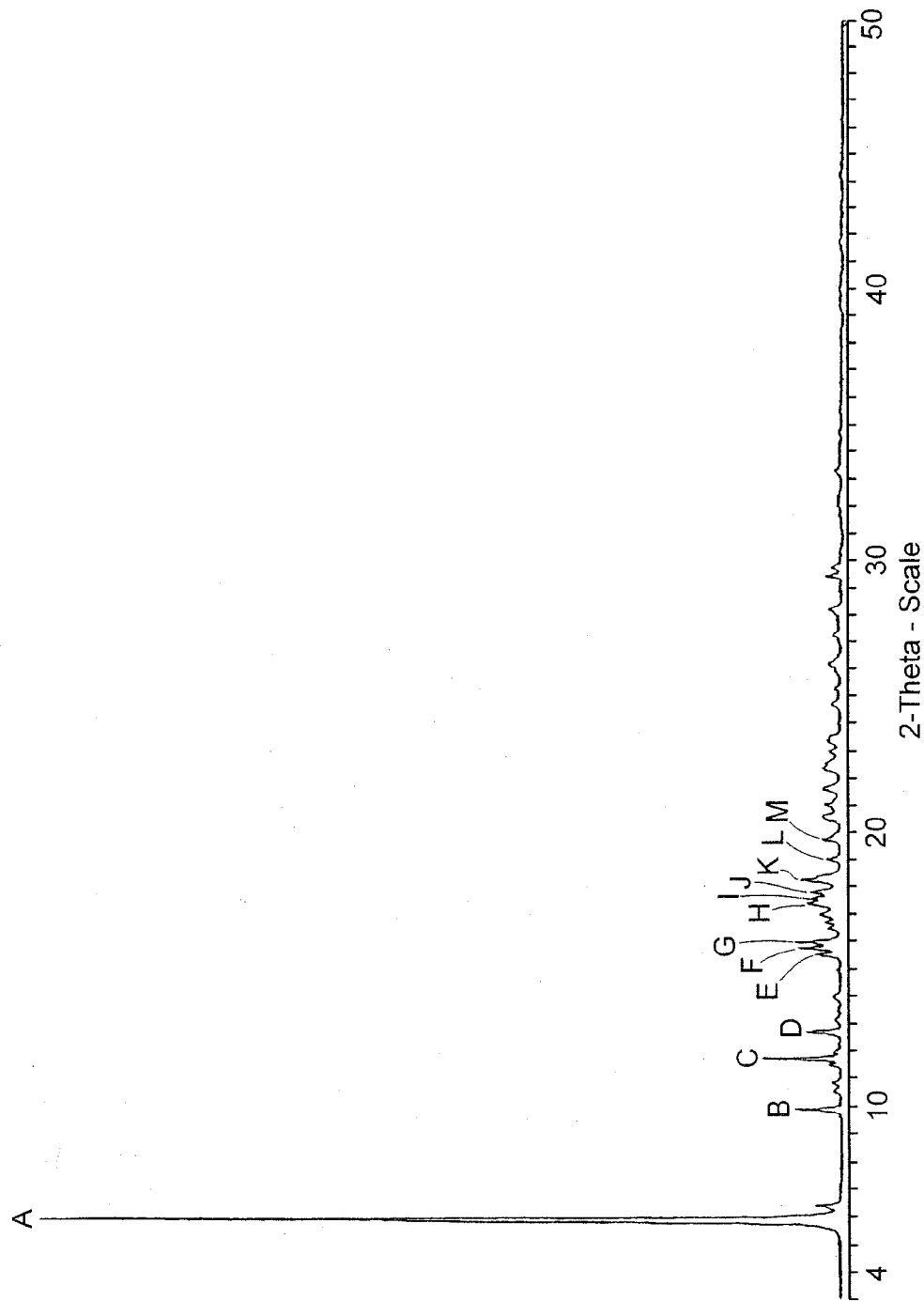
FIG. 1 depicts a X-ray powder diffraction pattern from a measurement on a sample of Form A using CuK$\alpha_1$ radiation, consistent with an embodiment of the invention.

As used above, and throughout the description of the invention, the following terms, unless otherwise indicated, shall be understood to have the following meanings.

"Citrate Salt" is meant to describe the citrate salt of (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol, and has the structure of formula III.

As used herein, "crystalline" refers to a solid having a highly regular chemical structure. In particular, a crystalline Citrate Salt may be produced as one or more single crystalline forms of the Citrate Salt. For the purposes of this application, the terms "single crystalline form" and "polymorph" are synonymous; the terms distinguish between crystals that have different properties (e.g., different XRPD patterns, different DSC scan results). Pseudopolymorphs are typically different solvates of a material, and thus their properties differ from one another. Thus, each distinct polymorph and pseudopolymorph of the Citrate Salt is considered to be a distinct single crystalline form herein.

"Substantially crystalline" refers to Citrate salts that may be at least a particular weight percent crystalline. Particular weight percentages are 10%, 20%, 30% 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. In some embodiments, substantially crystalline refers to Citrate Salts that are at least 70% crystalline. In other embodiments, substantially crystalline refers to Citrate Salts that are at least 90% crystalline.

"Form A" is meant to describe a crystalline form of a compound of formula III that may be characterized using distinguishing data. Exemplary data is found in FIGS. 1, 2, 3, 4, and 5, and in Tables 1 and 2.

"Form B" is meant to describe a crystalline form of a compound of formula III that may be characterized using distinguishing data. Exemplary data is found in FIGS. 6, 7, 8, 12, 13, and in Tables 3 and 4.

The term "solvate or solvated" means a physical association of a compound of this invention with one or more solvent molecules. This physical association includes hydrogen bonding. In certain instances the solvate will be capable of isolation, for example when one or more solvent molecules are incorporated in the crystal lattice of the crystalline solid. "Solvate or solvated" encompasses both solution-phase and isolable solvates. Representative solvates include, for example, a hydrate, ethanolates or a methanolate.

The term "hydrate" is a solvate wherein the solvent molecule is H$_2$O that is present in a defined stoichiometric amount, and may for example, include hemihydrate, monohydrate, dihydrate, or trihydrate.

The term "mixture" is used to refer to the combined elements of the mixture regardless of the phase-state of the combination (e.g., liquid or liquid/crystalline).

The term "seeding" is used to refer to the addition of a crystalline material to initiate recrystallization.

A "subject" is preferably a bird or mammal, such as a human, but can also be an animal in need of veterinary treatment, e.g., domestic animals (e.g., dogs, cats, and the like), farm animals (e.g., cows, sheep, fowl, pigs, horses, and the like) and laboratory animals (e.g., rats, mice, guinea pigs, and the like).

An "effective amount" of the Citrate Salt is an amount which results in the inhibition of one or more processes mediated by the binding of a chemokine to a receptor in a subject with a disease associated with aberrant leukocyte recruitment and/or activation. Examples of such processes include leukocyte migration, integrin activation, transient increases in the concentration of intracellular free calcium [Ca$^{2+}$]$_i$, and granule release of proinflammatory mediators. Alternatively, an "effective amount" of the Citrate Salt is a quantity sufficient to achieve a desired therapeutic and/or prophylactic effect, such as an amount which results in the prevention of or a decrease in the symptoms associated with a disease associated with aberrant leukocyte recruitment and/or activation.

As used herein, "pro-inflammatory cells" includes but is not limited to leukocytes, since chemokine receptors can be expressed on other cell types, such as neurons and epithelial cells.

In one aspect, the present invention is directed to a citrate salt of the compound (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol. Accordingly, the present invention provides a compound having structural formula (III):

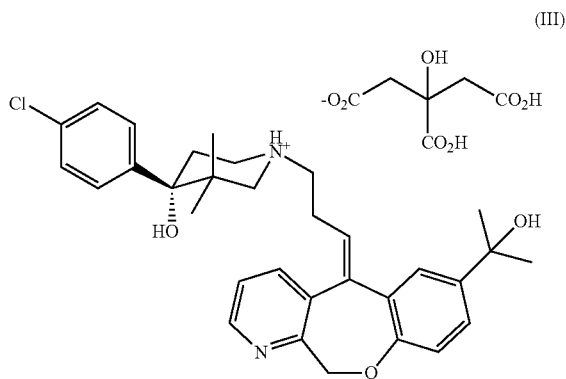

Provided herein is an assortment of characterizing information to describe the citrate salt forms of (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol. It should be understood, however, that not all such information is required for one skilled in the art to determine that such particular form is present in a given composition, but that the determination of a particular form can be achieved using any portion of the characterizing information that one skilled in the art would recognize as sufficient for establishing the presence of a particular form, e.g., even a single distinguishing peak can be sufficient for one skilled in the art to appreciate that such particular form is present.

In some embodiments, the Citrate Salt is substantially crystalline. Non-limiting examples of crystalline Citrate Salts include a single crystalline form of the Citrate Salt (e.g., Form A); a mixture of different single crystalline forms (e.g., a mixture of Form A and B, a mixture of any combination of Forms A, C, and D, a mixture of any combination of Forms B, E, F, G, and H); and a mixture of one or more single crystalline forms that excludes one or more designated single crystalline forms (e.g., a mixture of crystalline forms of the Citrate Salt excluding Form A). An embodiment of the invention is also directed to a Citrate Salt that excludes one or more designated single crystalline forms from a particular weight percentage of the Citrate Salt (e.g., the Citrate Salt being at least 90% by weight other than Form A). Particular weight percentages may be 10%, 20%, 30% 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%.

Alternatively, embodiments of the invention are directed to a crystalline Citrate Salt, wherein at least a particular percentage by weight of the crystalline Citrate Salt is a specific single crystalline form, a combination of particular crystalline forms, or excludes one or more particular crystalline forms. Particular weight percentages may be 10%, 20%, 30% 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%.

Other embodiments of the invention are directed to the Citrate Salt being a single crystalline form, or being substantially a designated single crystalline form. The single crystalline form may be a particular percentages by weight of the Citrate Salt. Particular weight percentages are 10%, 20%, 30% 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. When a particular percentage by weight of a citrate salt is a single crystalline form, the remainder of the citrate salt is some combination of amorphous form of the Citrate Salt, and one or more crystalline forms of the Citrate Salt excluding the single crystalline form.

Examples of a single crystalline form include Form A, B, C, D, E, F, G, and H of the Citrate Salt, as well as descriptions of a single crystalline form characterized by one or more properties as discussed herein. The descriptions characterizing the single crystalline forms may also be used to describe the mixture of different forms that may be present in a crystalline Citrate Salt.

In the following description of particular polymorphs of the citrate salt of (S)-4-(4-Chloro-phenyl)-1-{3-[7-(1-hydroxy-1-methyl-ethyl)-11H-10-oxa-1-aza-dibenzo[a,d]cyclohepten-5-ylidene]propyl}-3,3-dimethyl-piperidin-4-ol, embodiments of the invention may be described with reference to a particular crystalline "Form" of the Citrate Salt (e.g., Form B). However, the particular crystalline forms of the Citrate Salt may also be characterized by one or more of the characteristics of the polymorph as described herein, with or without regard to referencing a particular "Form".

Form A

Particular embodiments of the invention are directed toward a single crystalline form of the citrate salt of (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol having Form A. In one particular embodiment of the invention, the single crystalline form of the Citrate Salt is characterized by a X-ray powder diffraction (XRPD) pattern substantially similar to FIG. 1, the pattern generated using CuK$\alpha_1$ radiation. The single crystalline form of the Citrate Salt may alternatively be characterized by the lines derived from profile fitting the pattern of FIG. 1 as listed in Table 1.

TABLE 1

Indexing of XRPD Pattern of FIG. 1

| h | k | l | multiplicity J | d-spacing (Å) | 2-theta $\lambda_{Cu} K\bar{\alpha}$ 1.54184 Å |
|---|---|---|---|---|---|
| 0 | 1 | 0 | 2 | 15.1877 | 5.8191 |
| 1 | 0 | 0 | 2 | 14.0302 | 6.2996 |
| 1 | 1 | 0 | 2 | 12.3910 | 7.1340 |
| −1 | 1 | 0 | 2 | 9.0102 | 9.8165 |
| 0 | 0 | 1 | 2 | 8.4624 | 10.4538 |
| 0 | −1 | 1 | 2 | 8.2004 | 10.7887 |
| 1 | 2 | 0 | 2 | 7.7576 | 11.4064 |
| 0 | 2 | 0 | 2 | 7.5939 | 11.6533 |
| −1 | −1 | 1 | 2 | 7.4446 | 11.8878 |
| 1 | 0 | 1 | 2 | 7.4434 | 11.8897 |
| 2 | 1 | 0 | 2 | 7.2834 | 12.1519 |

TABLE 1-continued

Indexing of XRPD Pattern of FIG. 1

| h | k | l | multiplicity J | d-spacing (Å) | 2-theta $\lambda_{Cu}$ K$\hat{\alpha}$ 1.54184 Å |
|---|---|---|---|---|---|
| −1 | 0 | 1 | 2 | 7.0641 | 12.5305 |
| 2 | 0 | 0 | 2 | 7.0151 | 12.6184 |
| 0 | 1 | 1 | 2 | 6.7840 | 13.0501 |
| 1 | −1 | 1 | 2 | 6.7639 | 13.0892 |
| 1 | 1 | 1 | 2 | 6.6066 | 13.4022 |
| 0 | −2 | 1 | 2 | 6.3956 | 13.8465 |
| −1 | −2 | 1 | 2 | 6.3605 | 13.9232 |
| 2 | 2 | 0 | 2 | 6.1955 | 14.2959 |
| −1 | 2 | 0 | 2 | 5.9522 | 14.8835 |
| −2 | 1 | 0 | 2 | 5.7297 | 15.4649 |
| −1 | 1 | 1 | 2 | 5.7068 | 15.5275 |
| −2 | −1 | 1 | 2 | 5.6454 | 15.6972 |
| 2 | 0 | 1 | 2 | 5.5646 | 15.9267 |
| 2 | 1 | 1 | 2 | 5.4031 | 16.4060 |
| 1 | −2 | 1 | 2 | 5.3966 | 16.4261 |
| −2 | −2 | 1 | 2 | 5.3339 | 16.6204 |
| 1 | 3 | 0 | 2 | 5.3156 | 16.6778 |
| −2 | 0 | 1 | 2 | 5.2505 | 16.8863 |
| 1 | 2 | 1 | 2 | 5.2383 | 16.9259 |
| 0 | 2 | 1 | 2 | 5.1189 | 17.3236 |
| 2 | −1 | 1 | 2 | 5.0633 | 17.5153 |
| 0 | 3 | 0 | 2 | 5.0626 | 17.5180 |
| −1 | −3 | 1 | 2 | 4.9960 | 17.7531 |
| 3 | 1 | 0 | 2 | 4.9178 | 18.0380 |
| 2 | 3 | 0 | 2 | 4.8839 | 18.1641 |
| 0 | −3 | 1 | 2 | 4.8396 | 18.3318 |
| 2 | 2 | 1 | 2 | 4.7201 | 18.8000 |
| 3 | 2 | 0 | 2 | 4.6805 | 18.9608 |
| 3 | 0 | 0 | 2 | 4.6767 | 18.9760 |
| −2 | −3 | 1 | 2 | 4.5839 | 19.3641 |
| −2 | 2 | 0 | 2 | 4.5051 | 19.7060 |
| −2 | 1 | 1 | 2 | 4.4792 | 19.8213 |
| −1 | 2 | 1 | 2 | 4.4702 | 19.8613 |
| −1 | 3 | 0 | 2 | 4.3518 | 20.4077 |
| 0 | −1 | 2 | 2 | 4.3301 | 20.5110 |
| 2 | −2 | 1 | 2 | 4.2880 | 20.7147 |
| −3 | −1 | 1 | 2 | 4.2691 | 20.8073 |
| 1 | −3 | 1 | 2 | 4.2453 | 20.9254 |
| −3 | −2 | 1 | 2 | 4.2356 | 20.9735 |
| 3 | 1 | 1 | 2 | 4.2350 | 20.9768 |
| 0 | 0 | 2 | 2 | 4.2312 | 20.9958 |
| 3 | 0 | 1 | 2 | 4.1996 | 21.1555 |
| −1 | −1 | 2 | 2 | 4.1702 | 21.3064 |
| 3 | 3 | 0 | 2 | 4.1303 | 21.5144 |
| 1 | 3 | 1 | 2 | 4.1293 | 21.5197 |
| −3 | 1 | 0 | 2 | 4.1252 | 21.5414 |
| 1 | 0 | 2 | 2 | 4.1188 | 21.5755 |
| 1 | −1 | 2 | 2 | 4.1056 | 21.6458 |
| 0 | −2 | 2 | 2 | 4.1002 | 21.6746 |
| −1 | −2 | 2 | 2 | 4.0573 | 21.9067 |
| −3 | 0 | 1 | 2 | 3.9946 | 22.2548 |
| 1 | 4 | 0 | 2 | 3.9893 | 22.2845 |
| −1 | 0 | 2 | 2 | 3.9864 | 22.3010 |
| 0 | 3 | 1 | 2 | 3.9757 | 22.3621 |
| 3 | 2 | 1 | 2 | 3.9689 | 22.4009 |
| −1 | −4 | 1 | 2 | 3.9504 | 22.5069 |
| 2 | 3 | 1 | 2 | 3.9472 | 22.5256 |
| −3 | −3 | 1 | 2 | 3.9139 | 22.7197 |
| 3 | −1 | 1 | 2 | 3.8833 | 22.9011 |
| 2 | 4 | 0 | 2 | 3.8788 | 22.9279 |
| 0 | 1 | 2 | 2 | 3.8619 | 23.0297 |
| 1 | 1 | 2 | 2 | 3.8565 | 23.0623 |
| 1 | −2 | 2 | 2 | 3.8242 | 23.2597 |
| −2 | −4 | 1 | 2 | 3.8151 | 23.3162 |
| 0 | 4 | 0 | 2 | 3.7969 | 23.4293 |
| 0 | −4 | 1 | 2 | 3.7901 | 23.4720 |
| −2 | −1 | 2 | 2 | 3.7312 | 23.8482 |
| −2 | 2 | 1 | 2 | 3.7247 | 23.8906 |
| −2 | −2 | 2 | 2 | 3.7223 | 23.9060 |
| 2 | 0 | 2 | 2 | 3.7217 | 23.9099 |
| −1 | −3 | 2 | 2 | 3.7097 | 23.9884 |
| 4 | 1 | 0 | 2 | 3.6759 | 24.2123 |
| 0 | −3 | 2 | 2 | 3.6686 | 24.2611 |
| 4 | 2 | 0 | 2 | 3.6417 | 24.4431 |
| 2 | −1 | 2 | 2 | 3.6399 | 24.4556 |
| −2 | 3 | 0 | 2 | 3.6096 | 24.6640 |
| −1 | 1 | 2 | 2 | 3.6032 | 24.7081 |
| 2 | 1 | 2 | 2 | 3.5901 | 24.7997 |
| −1 | 3 | 1 | 2 | 3.5794 | 24.8750 |
| 2 | −3 | 1 | 2 | 3.5705 | 24.9380 |
| −3 | 1 | 1 | 2 | 3.5547 | 25.0511 |
| 3 | 3 | 1 | 2 | 3.5381 | 25.1702 |
| −2 | 0 | 2 | 2 | 3.5321 | 25.2141 |
| 3 | 4 | 0 | 2 | 3.5299 | 25.2301 |
| −3 | 2 | 0 | 2 | 3.5251 | 25.2649 |
| −2 | −3 | 2 | 2 | 3.5096 | 25.3784 |
| 4 | 0 | 0 | 2 | 3.5076 | 25.3932 |
| −3 | −4 | 1 | 2 | 3.4608 | 25.7420 |
| 1 | 2 | 2 | 2 | 3.4463 | 25.8526 |
| 3 | −2 | 1 | 2 | 3.4381 | 25.9148 |
| 1 | −4 | 1 | 2 | 3.4238 | 26.0253 |
| 4 | 3 | 0 | 2 | 3.4205 | 26.0507 |
| −1 | 4 | 0 | 2 | 3.4089 | 26.1408 |
| 1 | −3 | 2 | 2 | 3.4080 | 26.1478 |
| −4 | −2 | 1 | 2 | 3.4003 | 26.2083 |
| 0 | 2 | 2 | 2 | 3.3920 | 26.2734 |
| 4 | 1 | 1 | 2 | 3.3822 | 26.3513 |
| 2 | −2 | 2 | 2 | 3.3819 | 26.3532 |
| −4 | −1 | 1 | 2 | 3.3610 | 26.5200 |
| 1 | 4 | 1 | 2 | 3.3423 | 26.6716 |
| 4 | 0 | 1 | 2 | 3.3101 | 26.9353 |
| 2 | 2 | 2 | 2 | 3.3033 | 26.9922 |
| 2 | 4 | 1 | 2 | 3.2941 | 27.0688 |
| 4 | 2 | 1 | 2 | 3.2925 | 27.0823 |
| −4 | −3 | 1 | 2 | 3.2769 | 27.2141 |
| −1 | −4 | 2 | 2 | 3.2747 | 27.2324 |
| −3 | −2 | 2 | 2 | 3.2658 | 27.3079 |
| 3 | 0 | 2 | 2 | 3.2341 | 27.5810 |
| −3 | −1 | 2 | 2 | 3.2221 | 27.6853 |
| −1 | −5 | 1 | 2 | 3.2147 | 27.7508 |
| 0 | 4 | 1 | 2 | 3.2101 | 27.7914 |
| −2 | 1 | 2 | 2 | 3.2083 | 27.8076 |
| −4 | 1 | 0 | 2 | 3.2071 | 27.8180 |
| 0 | −4 | 2 | 2 | 3.1978 | 27.9004 |
| 3 | 1 | 2 | 2 | 3.1929 | 27.9444 |
| −2 | −5 | 1 | 2 | 3.1864 | 28.0019 |
| −2 | −4 | 2 | 2 | 3.1803 | 28.0575 |
| 1 | 5 | 0 | 2 | 3.1790 | 28.0687 |
| −4 | 0 | 1 | 2 | 3.1746 | 28.1085 |
| 2 | 5 | 0 | 2 | 3.1674 | 28.1740 |
| −1 | 2 | 2 | 2 | 3.1656 | 28.1896 |
| −3 | −3 | 2 | 2 | 3.1643 | 28.2017 |
| 3 | −1 | 2 | 2 | 3.1343 | 28.4773 |
| −2 | 3 | 1 | 2 | 3.1160 | 28.6482 |
| 4 | −1 | 1 | 2 | 3.1041 | 28.7601 |
| 4 | 4 | 0 | 2 | 3.0978 | 28.8205 |
| −3 | 2 | 1 | 2 | 3.0967 | 28.8309 |
| 3 | 4 | 1 | 2 | 3.0868 | 28.9253 |
| 0 | −5 | 1 | 2 | 3.0831 | 28.9605 |
| 4 | 3 | 1 | 2 | 3.0752 | 29.0364 |
| −3 | 0 | 2 | 2 | 3.0493 | 29.2887 |
| 2 | −3 | 2 | 2 | 3.0421 | 29.3594 |
| 0 | 5 | 0 | 2 | 3.0375 | 29.4047 |
| −4 | −4 | 1 | 2 | 3.0368 | 29.4125 |
| 3 | 2 | 2 | 2 | 3.0254 | 29.5249 |
| 1 | 3 | 2 | 2 | 3.0174 | 29.6049 |
| −3 | −5 | 1 | 2 | 3.0100 | 29.6798 |
| 3 | 5 | 0 | 2 | 3.0074 | 29.7065 |
| −3 | 3 | 0 | 2 | 3.0034 | 29.7464 |
| 2 | −4 | 1 | 2 | 2.9993 | 29.7881 |
| 3 | −3 | 1 | 2 | 2.9941 | 29.8414 |
| 1 | −4 | 2 | 2 | 2.9816 | 29.9696 |
| −2 | 4 | 0 | 2 | 2.9761 | 30.0258 |

The single crystalline form of the Citrate Salt may also be characterized by one or more of the peaks of a XRPD pattern. For example, one embodiment of the invention characterizes a single crystalline form of the Citrate Salt using at least one line corresponding to a major peak of the XRPD pattern of FIG. 1. The major peaks are labeled A-M on FIG. 1. The major peaks, as identified by their corresponding 2θ location from Table 1, are: 5.8, 9.8, 11.7, 12.6, 15.5, 15.7, 15.9, 17.3, 17.5, 17.8, 18.2, 19.0, and 19.7. The error in the 2θ locations are typically within ±0.1. Other examples of characterizing a single crystalline form utilize any number of the listed major peaks (e.g., 1, 2, 3, 4, 5, 6, 7, 8, 9, 10, 11, 12, or 13), or utilizing a subset of the major peaks that do not overlap peaks associated with one or more other polymorphs (e.g., utilizing one, two, three, four, five, six, seven or more of the major peaks listed above but excluding the peaks that overlap the peaks of Form B). In an alternative particular embodiment of the invention, the single crystalline form of the Citrate Salt is characterized by one or more of the calculated cell parameters found in Table 2. The calculated cell parameters are based upon analysis of corresponding XRPD measurements. From the results of the analysis, the crystalline structure is also characterized to be triclinic P1 (Z=1 and Z'=2).

TABLE 2

Cell Parameters from XRPD Scan of Form A a = 14.754(4) Å
b = 16.345(0) Å
c = 8.676(0) Å
α = 102.29(8)°
β = 90.56(8)°
γ = 72.29(7)°
V = 1944.1 Å$^3$
Density = 1.239 (Z = 1 and Z' = 2)

Figure 2:
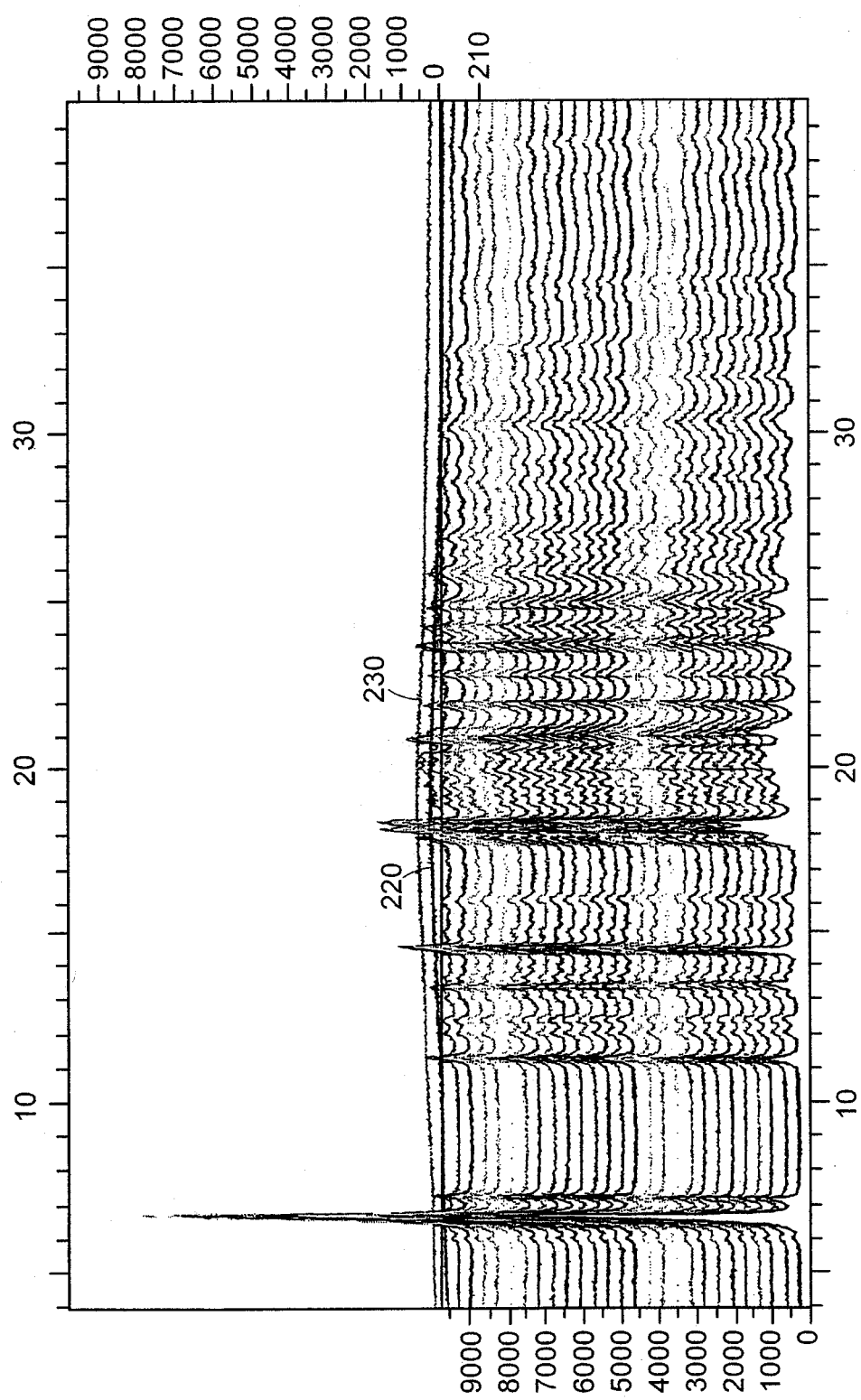
FIG. 2 depicts isothermal X-ray powder diffraction patterns from measurements on a sample of Form A using CoK$\alpha_1$ ($\lambda$=1.7890 Å) and CoK$\alpha_2$ ($\lambda$=1.7929 Å) radiation taken at temperatures from −80° C. to 190° C. at intervals of 10° C., in accord with an embodiment of the invention.

In another particular embodiment of the invention, the single crystalline form of the Citrate Salt is characterized by having a stability transition in the range of 150° C. and 160° C. as observed with controlled temperature X-ray powder diffraction. In FIG. 2, the results of a series of XRPD scans, measured at temperatures from −80° C. to 190° C. at intervals of 10° C. on a sample of Form A using CoKα$_1$ (λ=1.7890 Å) and CoKα$_2$ (λ=1.7929 Å) radiation, are presented. It is noted that from −80° C. to 150° C. the XRPD graphs do not show an appreciable change except for a typical heat-induced dilation as the temperature changes; the 150° C. measurement is shown in FIG. 2 by the scan 210. Above 150° C., however, the scans at progressively higher temperatures show a continuous evolution, corresponding to a transition away from a stable crystalline form between 150° C. and 160° C.

In another embodiment of the invention, Form A is characterized by a decomposition/melting phenomena above 170° C. as observed with controlled temperature X-ray powder diffraction. The measurements at 180° C. and 190° C. (shown by the scans 220, 230, respectively) in FIG. 2 have essentially no structural features, and correspond to a decomposed/melted crystalline Citrate Salt.

Figure 3:
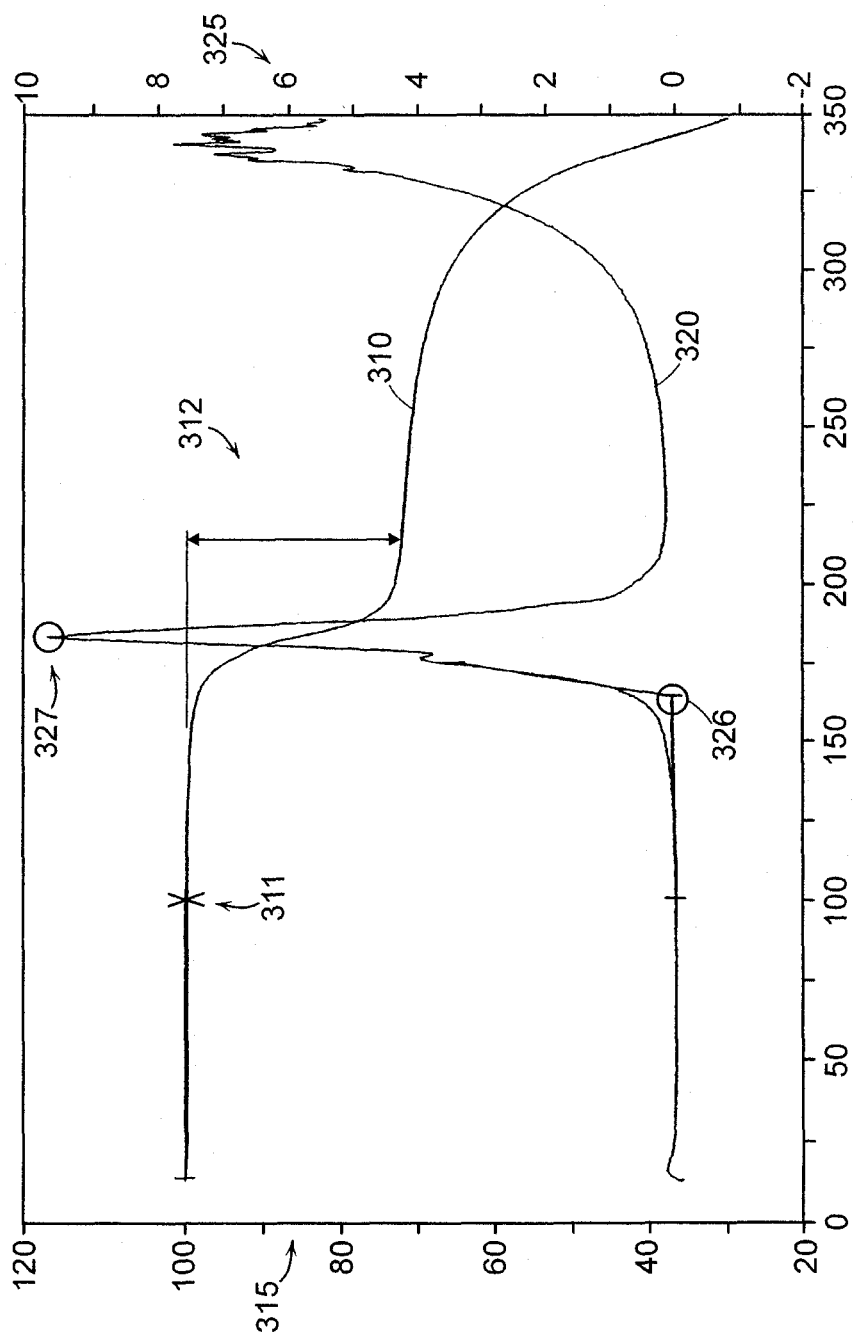
FIG. 3 depicts a thermal gravimetric analysis result from a measurement of a sample of Form A taken at a heating rate of 5° C./min in accord with an embodiment of the invention.

Form A is also characterized by a TGA measurement, in other embodiments of the invention. As shown in FIG. 3, the graph 310 corresponds to the weight of the sample 315 as a function of temperature, while graph 320 corresponds to a derived rate of weight loss 325 as a function of temperature, the measurement being performed at a constant rate of temperature change of 5° C./min. This polymorph is anhydrous; it has a very small weight loss 311 of about 0.23% (w/w) from ambient temperature to about 100° C. shown in FIG. 3. The polymorph is also characterized by the weight loss transition 312 corresponding to a weight loss of about 27.5% (w/w) beginning at about 164° C., as interpolated 326 from the derived rate of weight loss curve 320. The inflection point of this weight loss transition 312, corresponding to the maximum rate of weight loss 327, at 183° C. also characterizes this weight loss transition. The precision of all temperatures in all TGA scans herein are within ±3° C. of the stated temperatures.

Figure 4:
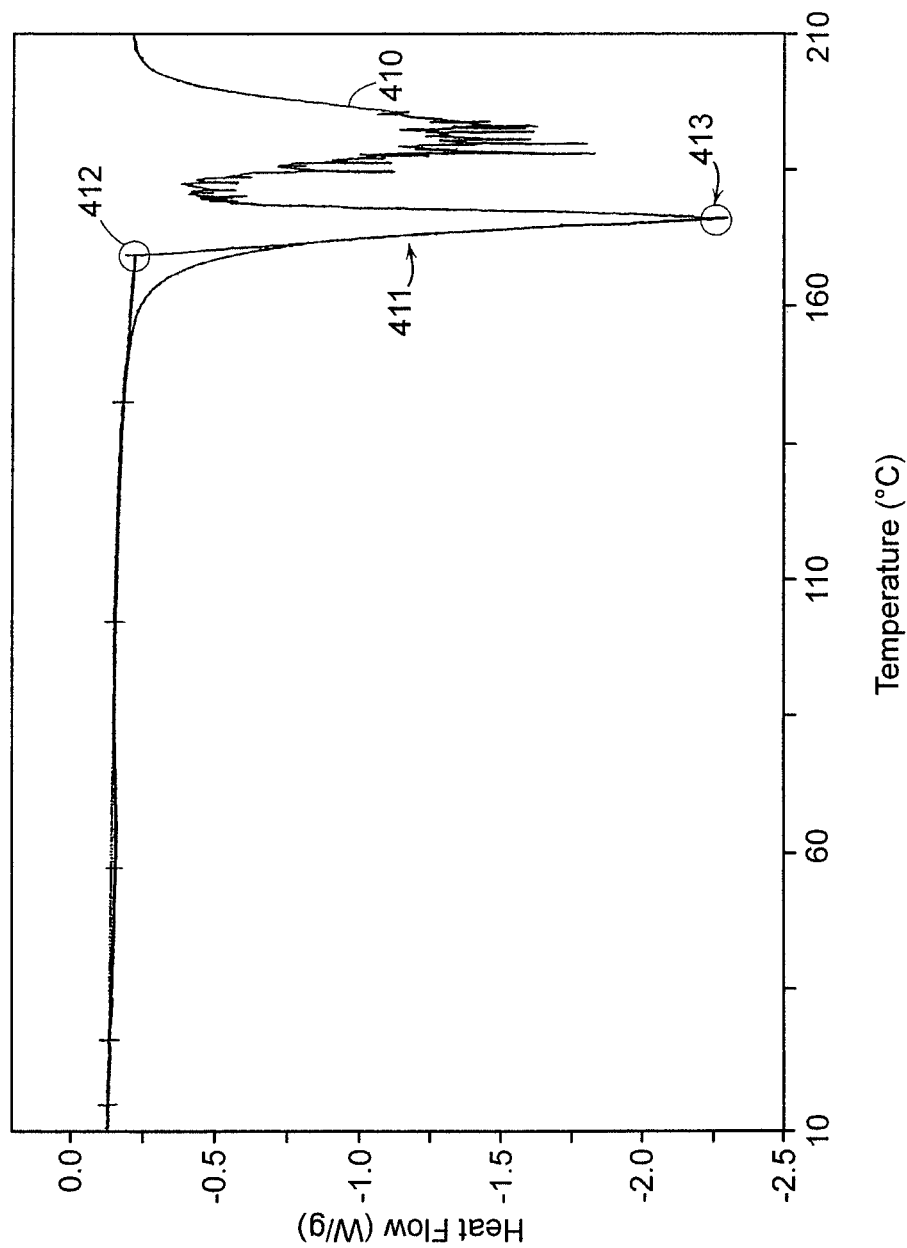
FIG. 4 depicts a differential scanning calorimetry result from a measurement of a sample of Form A taken at a heating rate of 5° C./min in accord with an embodiment of the invention.

A DSC measurement of a sample of Form A may be utilized to characterize a single crystalline form of the Citrate Salt in embodiments of the invention. FIG. 4 depicts the result of a DSC measurement on a sample of Form A at a heating rate of 5° C./min. The curve 410 depicts the heat flow into the sample as a function of temperature. A particular embodiment of the invention characterizes Form A by the endothermic transition 411 of the curve 410, the transition interpolated 412 to begin at 169° C., in FIG. 4. The maximum rate of heat loss 413 during the transition occurs at 176° C., the temperature being designated T$_{max}$, also characterizes this transition. The endothermic transition corresponds with the melting/decomposition of the crystalline sample. The precision of all temperatures in this DSC scans herein are within ±3° C. of the stated temperatures.

A DSC measurement on a sample of Form A performed at a heating rate of 1° C./min may also be used to characterize a single crystalline form of the Citrate Salt, in accordance with an embodiment of the invention. In such a measurement, the DSC scan is characterized by and endothermic transition interpolated to begin at 164° C.; a T$_{max}$=167° C. also serves to characterize the endothermic transition.

Figure 5:
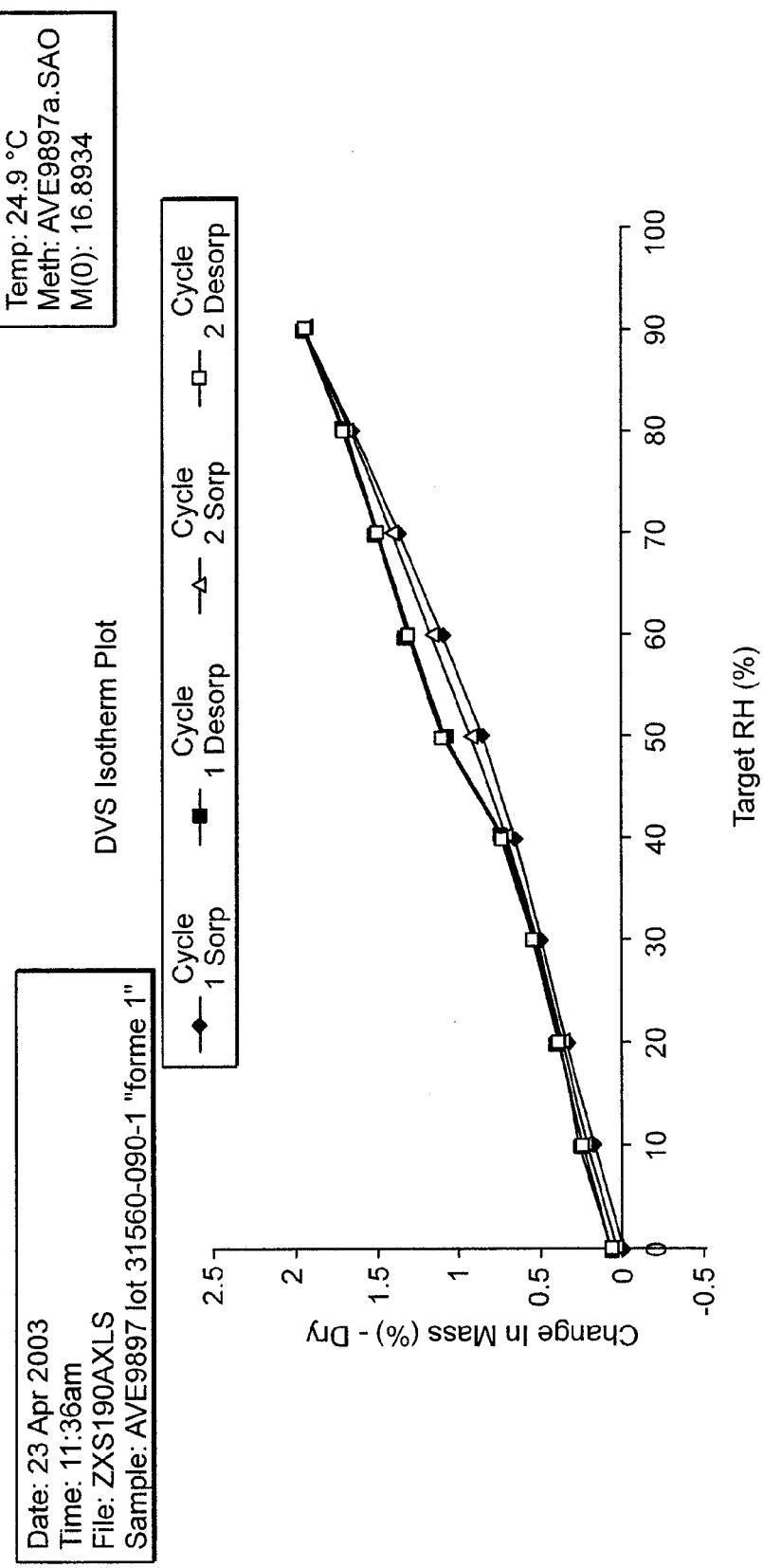
FIG. 5 depicts a water sorption/desorption isotherm result from a measurement of a sample of Form A taken at 25° C. in accord with an embodiment of the invention.

Particular embodiments of the invention utilize characterizations of Form A that refer to results of water sorption/desorption cycling. FIG. 5 depicts the result of two consecutive water sorption/desorption cycles performed at 25° C. on sample of Form A. The curves depict the percent change in mass, on a dry crystal basis, of the sample as a function of relative humidity.

The overlapping curves indicate the reversibility of the sorption phenomena. Correspondingly, Form A is also characterized from the observation that XRPD measurements made before and after cycling indicate no structural change in the sample.

In one embodiment of the invention, Form A is characterized by a change of about 1.9% in mass as the relative humidity is changed between 0% and 90% relative humidity, as shown in FIG. 5. The % change in mass is known to within ±0.1%. Alternatively, the embodiment may be characterized by a change of about 0.8 moles of water per mole of anhydrous crystal over the relative humidity range of 0% to 90%.

Embodiments of the invention also characterize Form A from XRPD measurements showing that the crystal does not change form when subjected to a week long exposure to a relative humidity of 97.5% at ambient temperature.

Form B

Form B is a single crystalline form of the Citrate Salt in a composition consistent with particular embodiments of the invention. One particular embodiment of the invention is directed towards Form B having a substantially similar XRPD pattern to what is displayed in FIG. 6. CuKα$_1$ radiation is used to generate the pattern of FIG. 6. Form B is alternatively characterized by the lines derived from profile fitting the XRPD pattern of FIG. 6, as listed in Table 3.

TABLE 3

Figure 6:
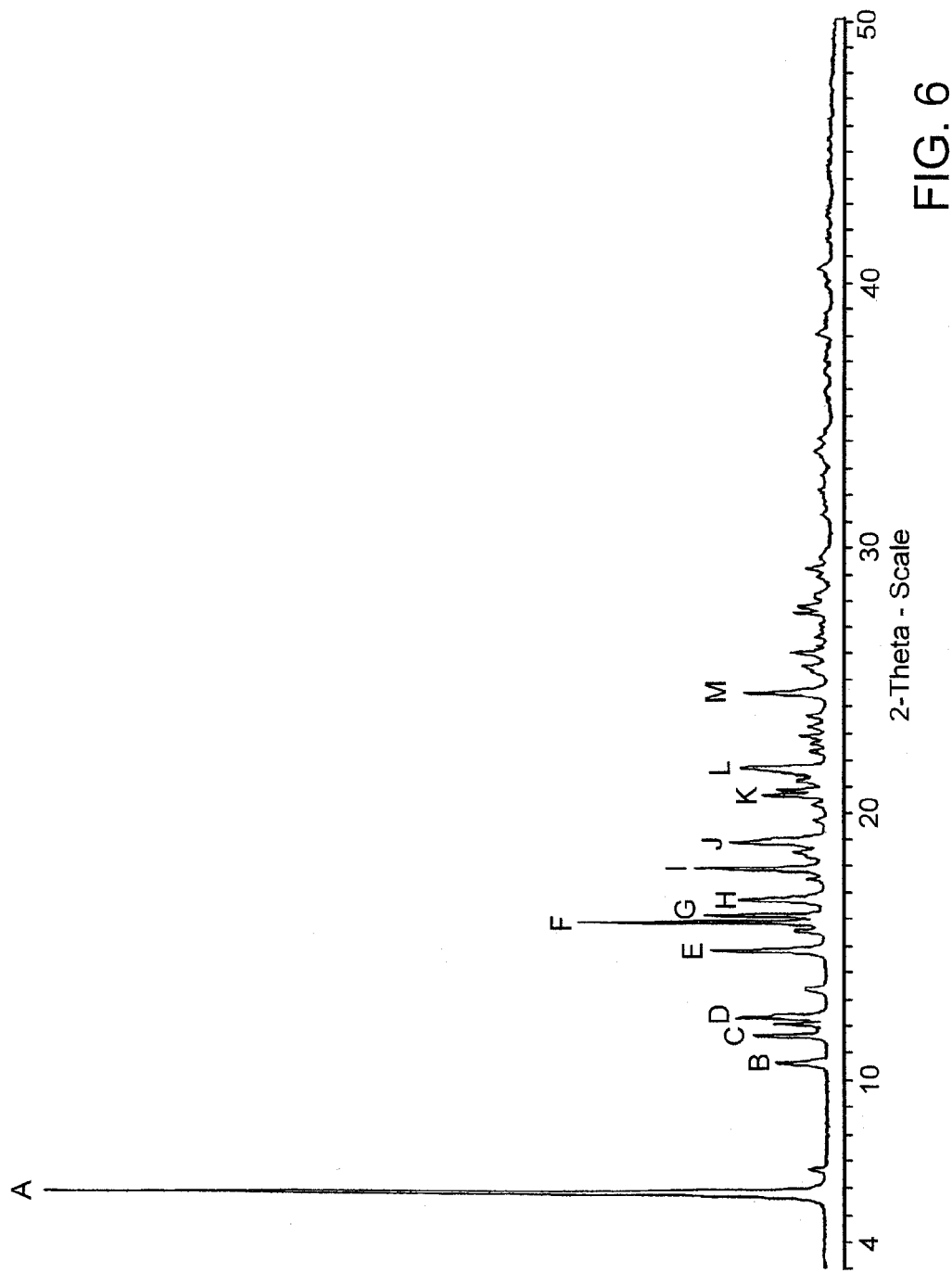
FIG. 6 depicts a X-ray powder diffraction pattern from a measurement on a sample of Form B using CuK$\alpha_1$ radiation, consistent with an embodiment of the invention.

Indexing of XRPD Pattern of FIG. 6

| h | k | l | multiplicity J | d-spacing (Å) | 2-theta $\lambda_{Cu} K\bar{\alpha}$ 1.54184 Å |
|---|---|---|---|---|---|
| 0 | 2 | 0 | 2 | 15.2730 | 5.7866 |
| 1 | 1 | 0 | 4 | 13.2774 | 6.6572 |
| 1 | 2 | 0 | 4 | 10.6073 | 8.3357 |
| 1 | 3 | 0 | 4 | 8.3781 | 10.5592 |
| 0 | 1 | 1 | 4 | 8.2924 | 10.6686 |
| 0 | 4 | 0 | 2 | 7.6365 | 11.5880 |
| 0 | 2 | 1 | 4 | 7.5043 | 11.7929 |
| 1 | 0 | 1 | 4 | 7.4388 | 11.8970 |
| 2 | 0 | 0 | 2 | 7.3715 | 12.0061 |
| 1 | 1 | 1 | 8 | 7.2276 | 12.2460 |
| 2 | 1 | 0 | 4 | 7.1658 | 12.3520 |
| 1 | 4 | 0 | 4 | 6.7808 | 13.0562 |
| 1 | 2 | 1 | 8 | 6.6877 | 13.2388 |
| 2 | 2 | 0 | 4 | 6.6387 | 13.3370 |
| 0 | 3 | 1 | 4 | 6.5772 | 13.4624 |
| 1 | 3 | 1 | 8 | 6.0066 | 14.7481 |
| 2 | 3 | 0 | 4 | 5.9710 | 14.8365 |
| 0 | 4 | 1 | 4 | 5.7149 | 15.5053 |
| 1 | 5 | 0 | 4 | 5.6438 | 15.7017 |
| 2 | 0 | 1 | 4 | 5.6012 | 15.8219 |
| 2 | 1 | 1 | 8 | 5.5094 | 16.0874 |
| 1 | 4 | 1 | 8 | 5.3286 | 16.6372 |
| 2 | 4 | 0 | 4 | 5.3036 | 16.7159 |
| 2 | 2 | 1 | 8 | 5.2587 | 16.8596 |
| 0 | 6 | 0 | 2 | 5.0910 | 17.4194 |
| 0 | 5 | 1 | 4 | 4.9836 | 17.7979 |
| 2 | 3 | 1 | 8 | 4.9077 | 18.0755 |
| 3 | 1 | 0 | 4 | 4.8519 | 18.2848 |
| 1 | 6 | 0 | 4 | 4.8122 | 18.4373 |
| 1 | 5 | 1 | 8 | 4.7211 | 18.7960 |
| 2 | 5 | 0 | 4 | 4.7038 | 18.8659 |
| 3 | 2 | 0 | 4 | 4.6781 | 18.9704 |
| 2 | 4 | 1 | 8 | 4.5165 | 19.6556 |
| 3 | 3 | 0 | 4 | 4.4258 | 20.0628 |
| 0 | 6 | 1 | 4 | 4.3830 | 20.2606 |
| 0 | 0 | 2 | 2 | 4.3080 | 20.6173 |
| 3 | 0 | 1 | 4 | 4.2688 | 20.8088 |
| 0 | 1 | 2 | 4 | 4.2658 | 20.8236 |
| 3 | 1 | 1 | 8 | 4.2277 | 21.0133 |
| 1 | 6 | 1 | 8 | 4.2013 | 21.1469 |
| 2 | 6 | 0 | 4 | 4.1891 | 21.2094 |
| 1 | 7 | 0 | 4 | 4.1843 | 21.2339 |
| 0 | 2 | 2 | 4 | 4.1462 | 21.4311 |
| 1 | 0 | 2 | 4 | 4.1351 | 21.4895 |
| 3 | 4 | 0 | 4 | 4.1326 | 21.5028 |
| 2 | 5 | 1 | 8 | 4.1286 | 21.5237 |
| 3 | 2 | 1 | 8 | 4.1112 | 21.6158 |
| 1 | 1 | 2 | 8 | 4.0977 | 21.6879 |
| 1 | 2 | 2 | 8 | 3.9914 | 22.2729 |
| 0 | 3 | 2 | 4 | 3.9675 | 22.4087 |
| 3 | 3 | 1 | 8 | 3.9368 | 22.5858 |
| 0 | 7 | 1 | 4 | 3.8929 | 22.8438 |
| 1 | 3 | 2 | 8 | 3.8312 | 23.2169 |
| 3 | 5 | 0 | 4 | 3.8292 | 23.2292 |
| 0 | 8 | 0 | 2 | 3.8182 | 23.2966 |
| 2 | 6 | 1 | 8 | 3.7674 | 23.6157 |
| 1 | 7 | 1 | 8 | 3.7639 | 23.6379 |
| 2 | 7 | 0 | 4 | 3.7551 | 23.6941 |
| 0 | 4 | 2 | 4 | 3.7521 | 23.7131 |
| 3 | 4 | 1 | 8 | 3.7261 | 23.8810 |
| 2 | 0 | 2 | 4 | 3.7194 | 23.9248 |
| 1 | 8 | 0 | 4 | 3.6963 | 24.0766 |
| 2 | 1 | 2 | 8 | 3.6921 | 24.1041 |
| 4 | 0 | 0 | 2 | 3.6858 | 24.1465 |
| 4 | 1 | 0 | 4 | 3.6592 | 24.3243 |
| 1 | 4 | 2 | 8 | 3.6362 | 24.4805 |
| 2 | 2 | 2 | 8 | 3.6138 | 24.6348 |
| 4 | 2 | 0 | 4 | 3.5829 | 24.8506 |
| 3 | 6 | 0 | 4 | 3.5358 | 25.1873 |
| 0 | 5 | 2 | 4 | 3.5207 | 25.2969 |
| 3 | 5 | 1 | 8 | 3.4992 | 25.4550 |
| 2 | 3 | 2 | 8 | 3.4936 | 25.4962 |
| 0 | 8 | 1 | 4 | 3.4908 | 25.5170 |
| 4 | 3 | 0 | 4 | 3.4657 | 25.7053 |
| 2 | 7 | 1 | 8 | 3.4424 | 25.8824 |
| 1 | 5 | 2 | 8 | 3.4244 | 26.0205 |
| 1 | 8 | 1 | 8 | 3.3969 | 26.2349 |
| 2 | 8 | 0 | 4 | 3.3904 | 26.2859 |
| 4 | 0 | 1 | 4 | 3.3887 | 26.2995 |
| 4 | 1 | 1 | 8 | 3.3680 | 26.4637 |
| 2 | 4 | 2 | 8 | 3.3439 | 26.6586 |
| 4 | 4 | 0 | 4 | 3.3194 | 26.8592 |
| 4 | 2 | 1 | 8 | 3.3083 | 26.9509 |
| 1 | 9 | 0 | 4 | 3.3075 | 26.9573 |
| 0 | 6 | 2 | 4 | 3.2886 | 27.1151 |
| 3 | 6 | 1 | 8 | 3.2710 | 27.2634 |
| 3 | 7 | 0 | 4 | 3.2630 | 27.3320 |
| 3 | 0 | 2 | 4 | 3.2395 | 27.5341 |
| 3 | 1 | 2 | 8 | 3.2214 | 27.6916 |
| 4 | 3 | 1 | 8 | 3.2153 | 27.7454 |
| 1 | 6 | 2 | 8 | 3.2097 | 27.7947 |
| 2 | 5 | 2 | 8 | 3.1769 | 28.0873 |
| 3 | 2 | 2 | 8 | 3.1690 | 28.1592 |
| 0 | 9 | 1 | 4 | 3.1578 | 28.2608 |
| 4 | 5 | 0 | 4 | 3.1559 | 28.2786 |
| 2 | 8 | 1 | 8 | 3.1549 | 28.2872 |
| 4 | 4 | 1 | 8 | 3.0974 | 28.8236 |
| 1 | 9 | 1 | 8 | 3.0878 | 28.9156 |
| 3 | 3 | 2 | 8 | 3.0870 | 28.9230 |
| 2 | 9 | 0 | 4 | 3.0829 | 28.9623 |
| 0 | 7 | 2 | 4 | 3.0657 | 29.1283 |
| 0 | 10 | 0 | 2 | 3.0546 | 29.2368 |
| 3 | 7 | 1 | 8 | 3.0515 | 29.2672 |
| 3 | 8 | 0 | 4 | 3.0151 | 29.6282 |
| 2 | 6 | 2 | 8 | 3.0033 | 29.7478 |
| 1 | 7 | 2 | 8 | 3.0015 | 29.7657 |
| 1 | 10 | 0 | 4 | 2.9911 | 29.8720 |
| 4 | 6 | 0 | 4 | 2.9855 | 29.9293 |
| 3 | 4 | 2 | 8 | 2.9823 | 29.9624 |
| 4 | 5 | 1 | 8 | 2.9634 | 30.1581 |

Form B is also characterized by one or more of the peaks in a XRPD pattern. For example, one embodiment of the invention characterizes a single crystalline form of the Citrate Salt using at least one line corresponding to a major peak of the XRPD pattern of FIG. 6. The major peaks are labeled A-M on FIG. 6. The major peaks, as identified by their corresponding 2θ location in Table 3, are: 5.8, 10.6, 11.6, 12.3, 14.8, 15.8, 16.1, 16.7, 17.8, 18.8, 20.6, 21.7, and 24.5. The error in the 2θ locations are typically within ±0.1. Other examples utilize any number of the listed major peaks (e.g., 1, 2, 3, 4, 5, 6, 7, 8, 9, 10, 11, 12, or 13), or utilizing a subset of the major peaks that do not overlap peaks associated with one or more other polymorphs (e.g., utilizing one, two, three, four, five, six, seven or more of the major peaks listed above but excluding the peaks that overlap the peaks of Form A). In another alternate embodiment of the invention, Form B is characterized by one or more of the calculated cell parameters of Table 4, derived from analysis conducted on a XRPD measurement. The crystalline structure is also characterized to be orthorhombic $P2_12_12_1$ (Z=4 and Z'=2).

TABLE 4

Cell Parameters from XRPD Scan of Form B $a = 14.743(8)$ Å
$b = 30.546(5)$ Å
$c = 8.616(4)$ Å
$\alpha = 90°$
$\beta = 90$ TABLE 4-continued Cell Parameters from XRPD Scan of Form B γ = 90°
V = 3880.6 Å$^3$
Density = 1.241 (Z = 4 and Z' = 1)

Figure 7:
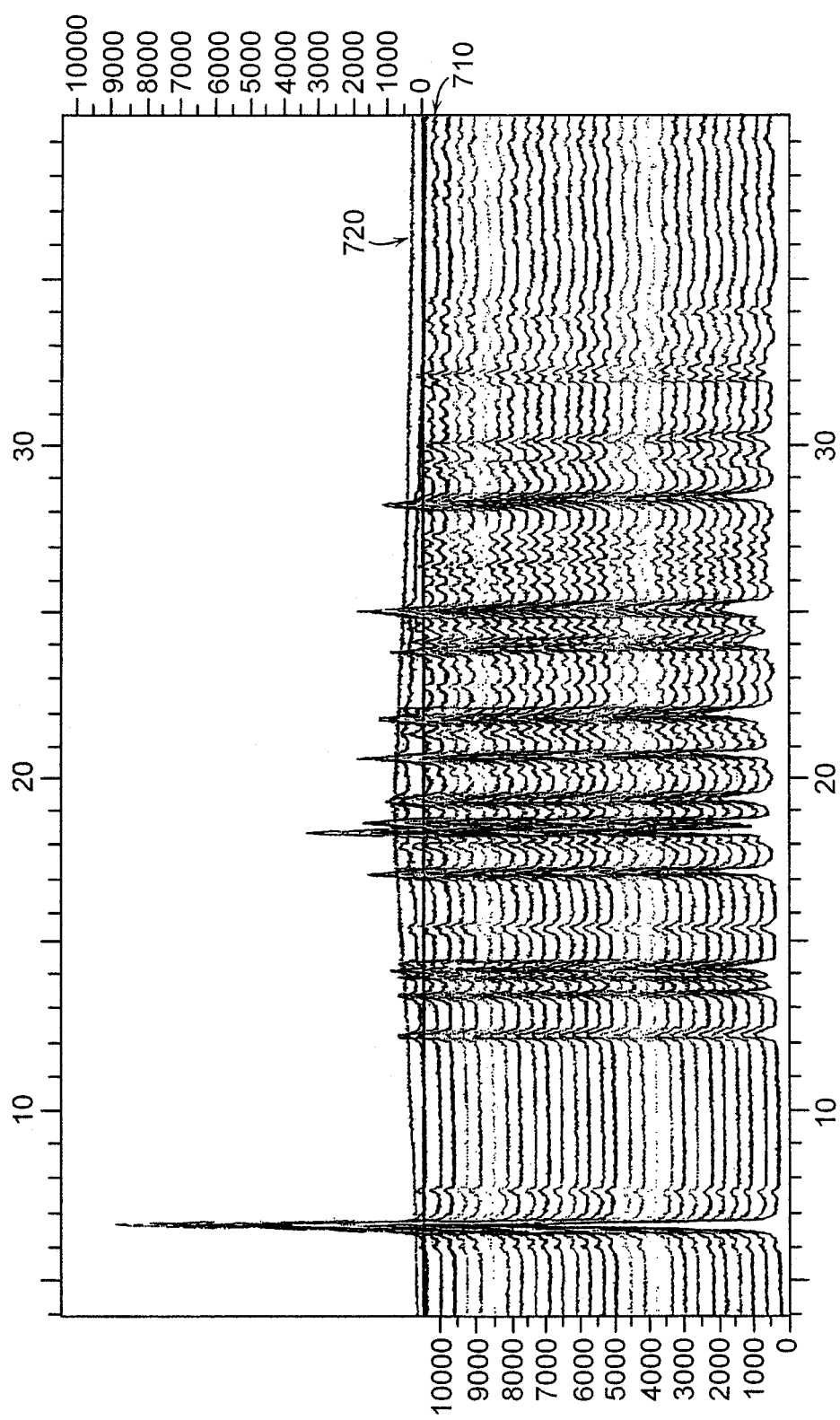
FIG. 7 depicts isothermal X-ray powder diffraction patterns from measurements on a sample of Form B using CoK$\alpha_1$ ($\lambda$=1.7890 Å) and CoK$\alpha_2$ ($\lambda$=1.7929 Å) radiation taken at temperatures from −80° C. to 190° C. at intervals of 10° C., in accord with an embodiment of the invention.

In a particular embodiment of the invention, Form B is characterized by a stability transition between 170° C. and 180° C. as detected from temperature controlled XRPD measurements. FIG. 7 depicts XRPD measurements on a sample Form B using CoKα$_1$ (λ=1.7890 Å) and CoKα$_2$ (λ=1.7929 Å) radiation. Each scan represents an isothermal measurement of the sample, the temperatures ranging from −80° C. to 190° C. at intervals of 10° C. Up to 170° C., the XRPD scans at different temperatures only display slight variations between each other due to typical heat-induced dilation (e.g., scan 710 corresponds with the measurement at 170° C.). Scans above 170° C. show alteration of spectral features corresponding to a transition away from a stable crystalline form.

In another embodiment of the invention, Form B is characterized by decomposition/melting between 180° C. and 190° C. as observed from isothermal XRPD measurements. This is indicated by the measurement at 190° C. (shown by scan 720) being essentially featureless and corresponding to decomposed/melted Form B.

Figure 8:
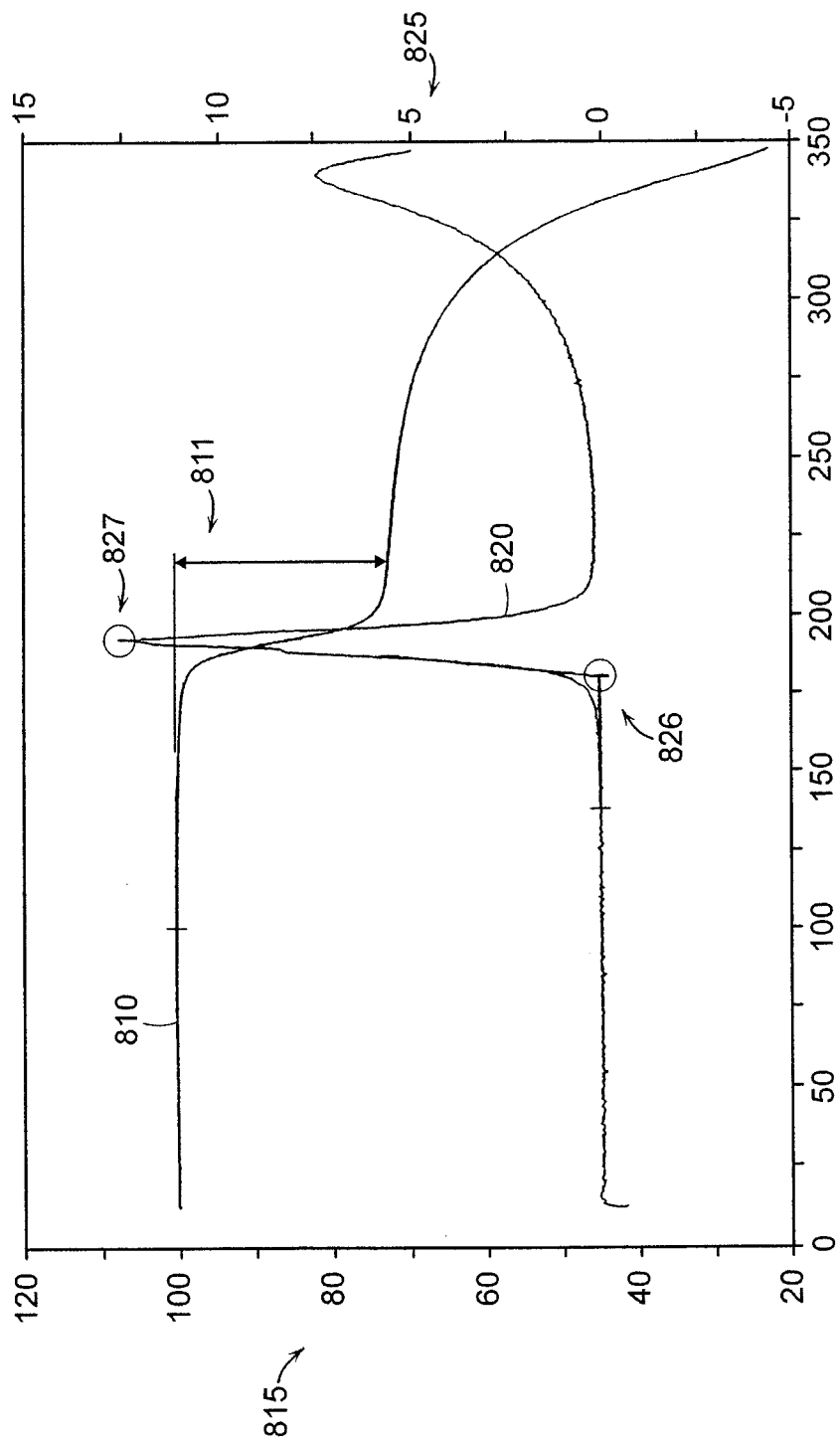
FIG. 8 depicts a thermal gravimetric analysis result from a measurement of a sample of Form B taken at a heating rate of 5° C./min in accord with an embodiment of the invention.
Figure 9:
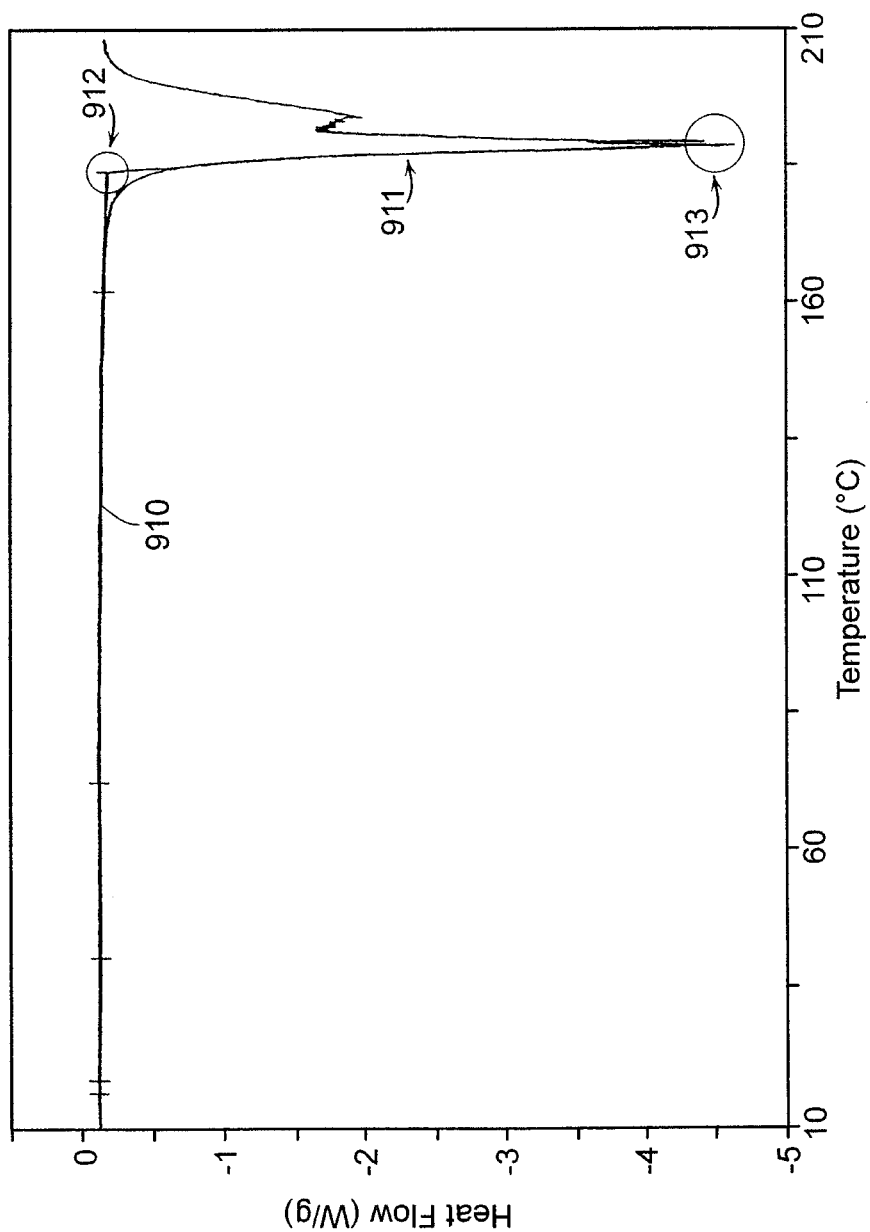
FIG. 9 depicts a differential scanning calorimetry result from a measurement of a sample of Form A taken at a heating rate of 5° C./min in accord with an embodiment of the invention.
Figure 10:
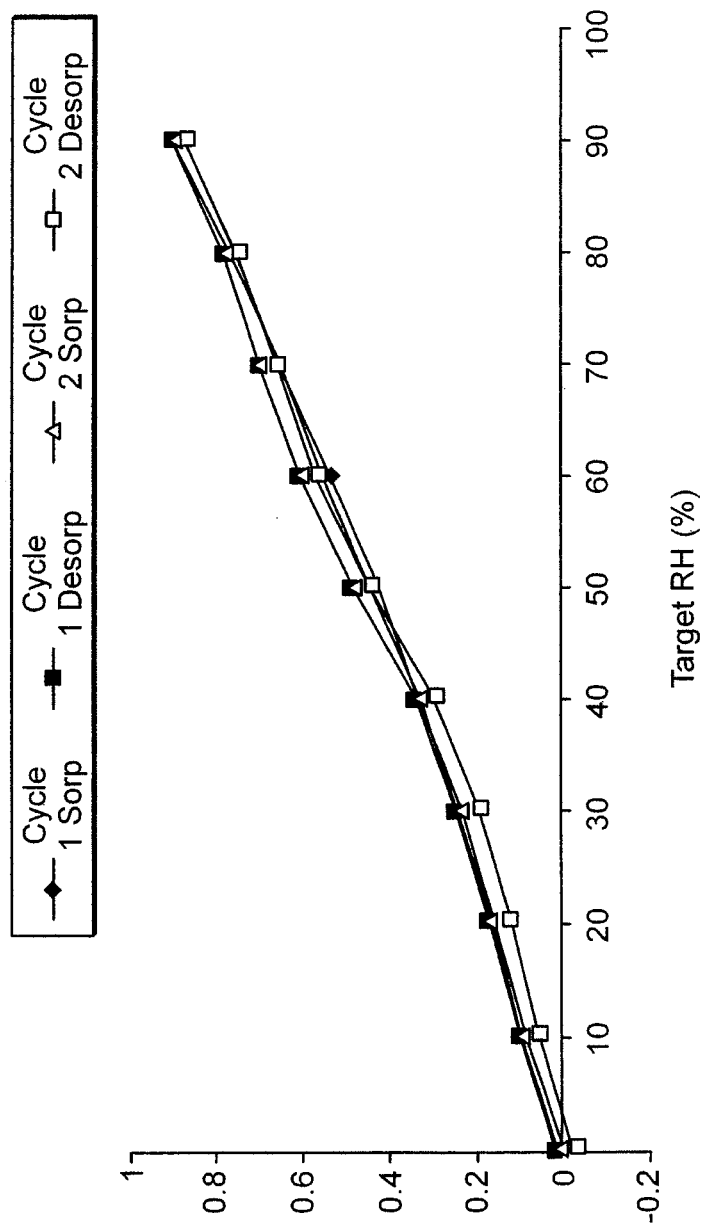
FIG. 10 depicts a water sorption/desorption isotherm result from a measurement of a sample of Form B taken at 25° C. in accord with an embodiment of the invention.

In a particular embodiment of the invention, Form B is characterized by one or more features of the TGA measurement in FIG. 8. The curve 810 graphs the weight of the sample 815 of Form B that is measured as a function of temperature; corresponding curve 820 graphs the derived rate of weight Loss 825 as a function of temperature. The heating rate of the measurement is 5° C./min. This polymorph is anhydrous. No weight loss is detected from ambient temperature to 100° C., as shown in FIG. 8. The single crystalline form is also be characterized by the weight loss transition 811 corresponding to a weight loss of about 27.5% (w/w) beginning at about 180° C., as interpolated 826 from the derived rate of weight loss curve 820. The inflection point of this weight loss transition 811, corresponding to the maximum rate of weight loss 827, at 192° C. also characterizes this weight loss transition.

Figure 12:
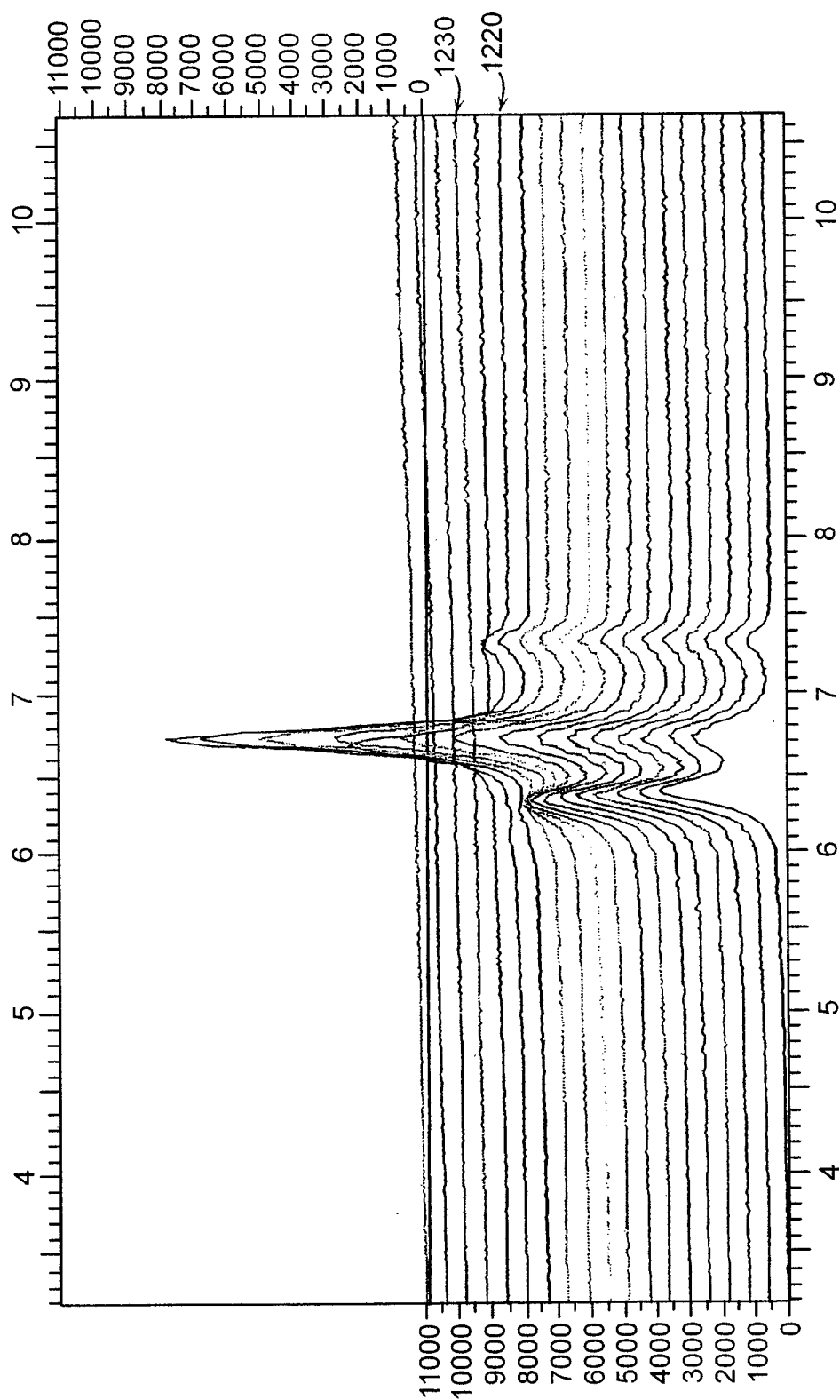
FIG. 12 depicts isothermal X-ray powder diffraction patterns from measurements using CoK$\alpha_1$ ($\lambda$=1.7890 Å) and CoK$\alpha_2$ ($\lambda$=1.7929 Å) radiation on a sample containing Forms A and C taken at temperatures from ambient to 210° C. at intervals of 10° C., in accord with an embodiment of the invention.

In another particular embodiment of the invention, Form B is characterized by one or more features of the DSC measurement depicted in FIG. 12. Using a heating rate of 5° C./min, the curve 1210 graphs the heat flow as a function of temperature. The endothermic transition (or heat flow transition) 1211 of the curve 1210 may be used to characterize the crystalline form. The transition is characterized by an interpolated 1212 beginning temperature at 184° C., and a maximum rate of heat loss 1213 during the transition at T$_{max}$=189° C. The transition corresponds with the melting/decomposition of the Form B sample.

In a related embodiment of the invention, Form B is characterized by a DSC measurement conducted at a heating rate of 1° C./min. In such a measurement, the DSC scan is characterized by and endothermic transition interpolated to begin at 174° C.; a T$_{max}$=179° C. also serves to characterize the endothermic transition.

Figure 13:
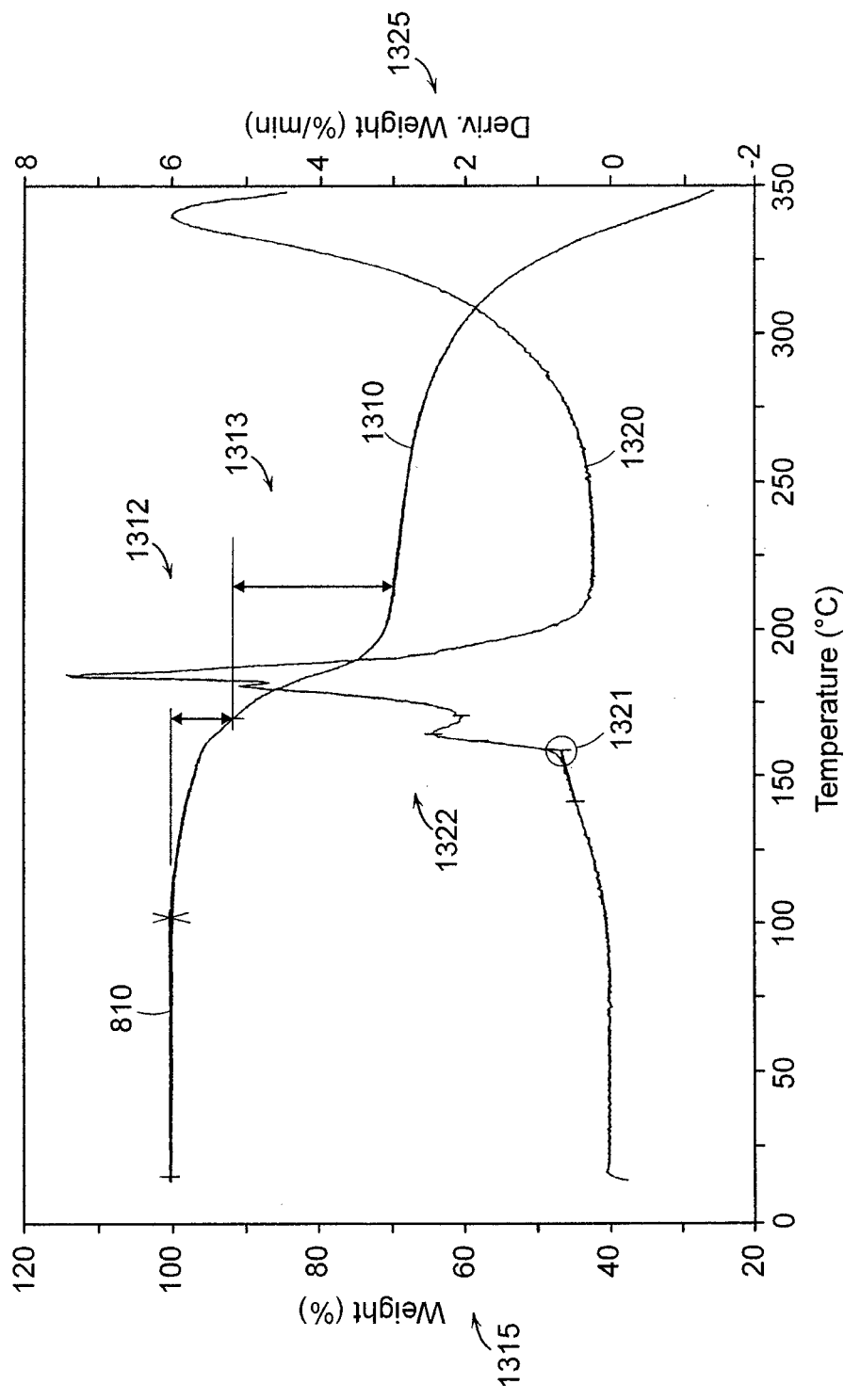
FIG. 13 depicts a thermal gravimetric analysis result from a measurement of a sample containing Forms A and C taken at a heating rate of 5° C./min in accord with an embodiment of the invention.

Other particular embodiments of the invention utilizing Form B may characterize the polymorph from a water sorption/desorption cycling experiment corresponding to the graph of FIG. 13. FIG. 13 shows the result of two consecutive water sorption/desorption cycles performed at 25° C. on sample of Form B, depicting the percent change in mass, on a dry crystal basis, of the sample as a function of relative humidity.

The overlapping curves indicate the reversibility of the sorption phenomena. Correspondingly, Form B is also be characterized from the observation that XRPD measurements made before and after cycling experiment indicate no structural change in the sample.

In one embodiment of the invention, Form B is characterized by a change of about 0.9% in mass as the relative humidity is changed between 0% and 90% relative humidity, as shown in FIG. 13. The % change in mass is known to within ±0.1%. Alternatively, the embodiment may be characterized by a change of about 0.4 moles of water per mole of anhydrous crystal over the relative humidity range of 0% to 90%.

Embodiments of the invention also characterize Form B from XRPD measurements showing that the crystal does not change form when subjected to a month long exposure to a relative humidity of 97.5% at ambient temperature. In addition, Form B is characterized by its stability when rinsed with water, as observed by XRPD before and after the rinsing; this also suggests the single crystalline form is characterized as being stable to 100% relative humidity at ambient temperature.

Form C

Figure 11:
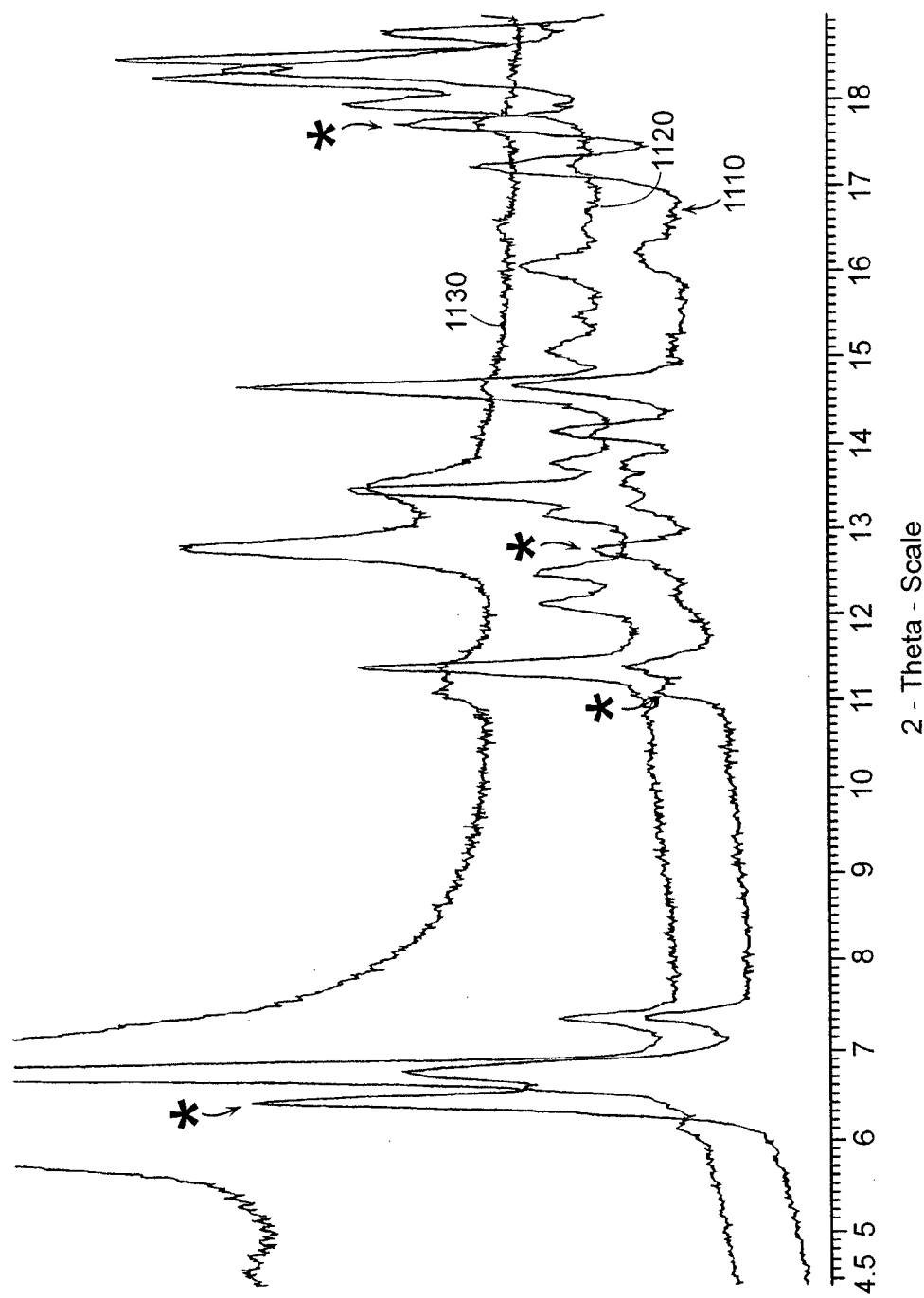
FIG. 11 depicts X-ray powder diffraction patterns from measurements using CoK$\alpha_1$ ($\lambda$=1.7890 Å) and CoK$\alpha_2$ ($\lambda$=1.7929 Å) radiation on a sample of Form A and two samples containing Forms A and C, consistent with an embodiment of the invention.

In an embodiment of the invention, a single crystalline form of the Citrate Salt is characterized as having Form C. In particular, the single crystalline form may be characterized by particular features from the XRPD measurements shown in FIG. 11 using CoKα$_1$ (λ=1.7890 Å) and CoKα$_2$ (λ=1.7929 Å) radiation. FIG. 11 compares the relative intensity as a function of 2θ for scans 1110, 1120, 1130. Scans 1110 and 1130 correspond to measurements of samples including a mixture of Form A and Form C crystals. Scan 1120, corresponding to a sample of pure Form A, is provided to distinguish features in the XRPD scans 1110, 1130 that are unique to Form C of the Citrate Salt. At least four peaks that appear unique to Form C of the Citrate Salt are designated with a * on scan 1110 of FIG. 11. Thus, the single crystalline form of the Citrate Salt is characterized any number of these four peaks.

In another embodiment of the invention, Form C is characterized by a loss of stability between 150° C. and 160° C. as observed with temperature dependent XRPD measurements. FIG. 12 depicts XRPD measurements, using CoKα$_1$ (λ=1.7890 Å) and CoKα$_2$ (λ=1.7929 Å) radiation, on the same sample used to generate scan 1110 in FIG. 11. Each curve represents an isothermal scan of the sample in a dry nitrogen environment; the temperatures ranging from ambient temperature to 210° C. in intervals of 10° C. As the temperature is raised, the peak at 2θ~6.35 begins to lose intensity, the successive scans progressively resembling Form A. For the scan 1220 corresponding to T=160° C., the peaks characteristic of Form C are essentially not present; the sample now corresponding to crystalline Form A. Further increases in temperature eventually bring about the decomposition/melting of the crystalline Form A (e.g., scan 1230 corresponding to T=180° C.). Thus, XRPD measurements indicate a conversion of the Form C crystals to Form A between 150° C. and 160° C. Form C may also be characterized by particular features of a TGA measurement as shown in FIG. 13. The curve 1310 graphs the weight of the tested sample 1315 including Forms A and C as a function of temperature; corresponding curve 1320 graphs the derived rate of weight loss 1325 as a function of temperature.

In particular, Form C is characterized by the weight loss 1312, interpolated to begin at 157° C. 1321 and having a maximum rate of weight loss at 162° C. 1322. This weight loss of about 8.22% (w/w) is related to the conversion away from Form C. Thus, Form C is characterized as a crystal of the Citrate Salt that converts to Form A, beginning at about 157° C. with a maximum rate of weight loss at 162° C. according to TGA. Corresponding measurements made using TGA simultaneously with DSC, and a TGA measurement coupled with mass spectrometry, confirm these results.

A weight loss 1313 corresponds to the decomposition/melting of the subsequent Form A crystal; the third weight loss of 21.9% (w/w) having a maximum weight loss rate at 183° C. and beginning at 168° C.

Figure 14:
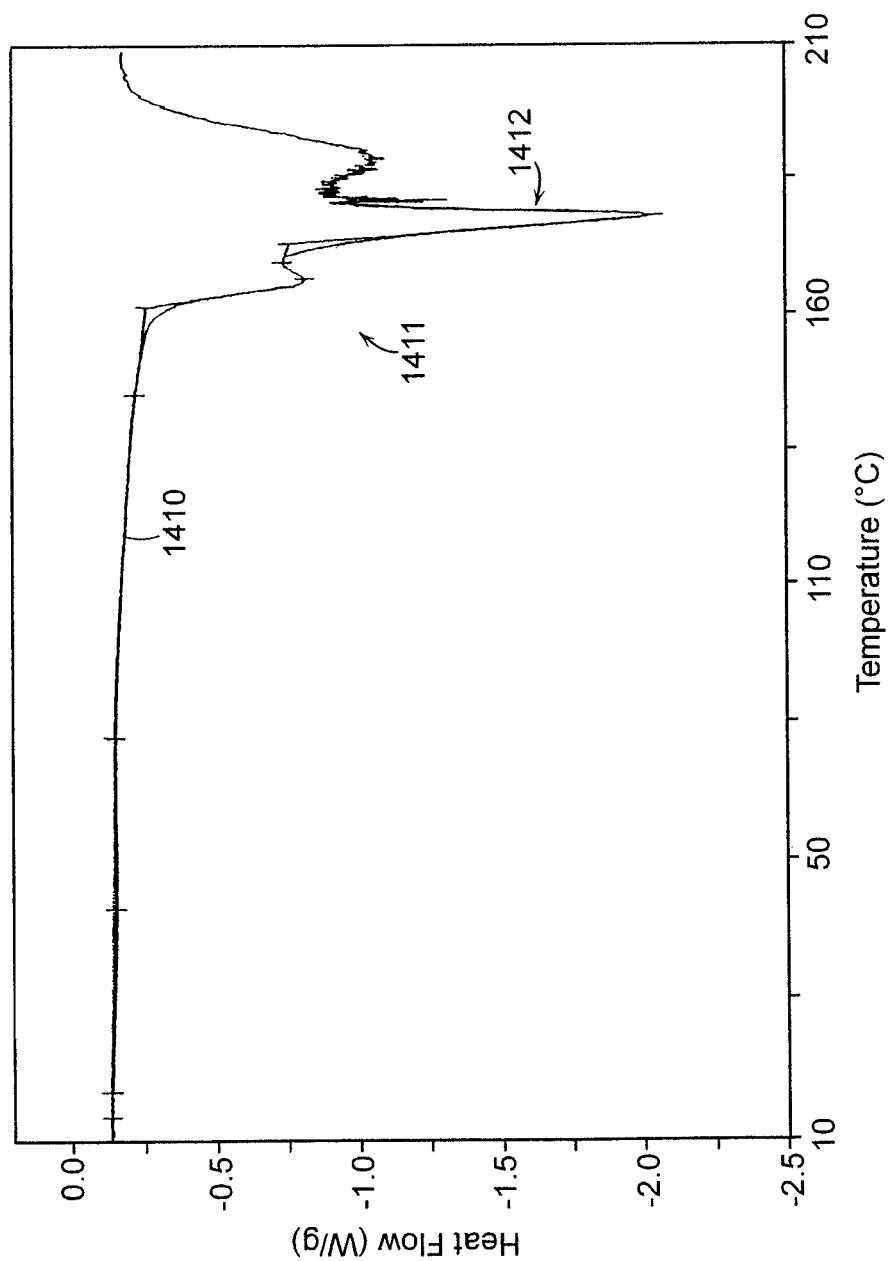
FIG. 14 depicts a differential scanning calorimetry result from a measurement of a sample containing Forms A and C taken at a heating rate of 5° C./min in accord with an embodiment of the invention.

The DSC measurement of FIG. 14 also characterize Form C. The curve 1410, generated from testing a sample including Forms A and C at a heating rate of 5° C./min, shows two strong endothermic transitions. In particular, Form C is characterized by the first endothermic transition 1411, interpolated to begin at about 161° C. and having a $T_{max}$=166° C. This is associated with the conversion of crystalline Form C to Form A. The second endothermic transition 1412, interpolated to begin at about 173° C. and having a $T_{max}$=178° C., corresponds with the melting/decomposition of Form A.

Alternatively, Form C is be characterized by a DSC measurement on a sample at a heating rate of 20° C./min. In particular, the endothermic transition corresponding to a transition between Form C and Form A is characterized by an interpolated beginning temperature of 165° C. and a $T_{max}$ of 171° C.

Figure 15:
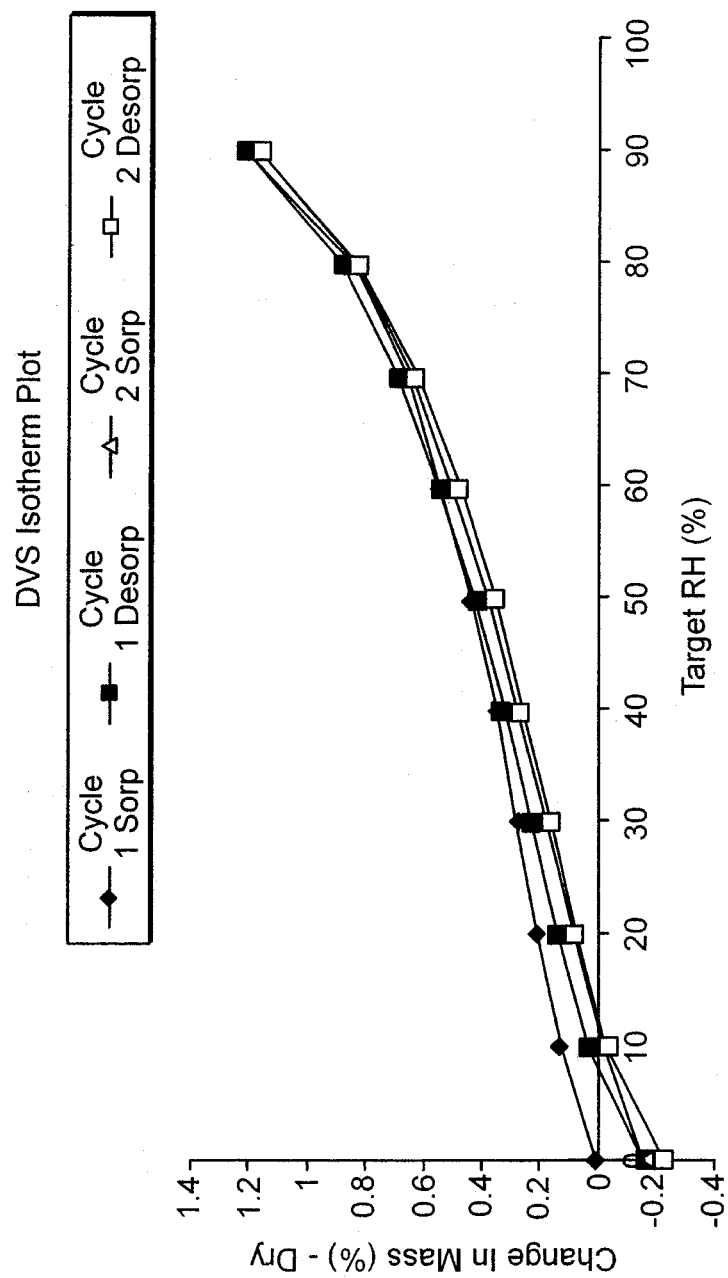
FIG. 15 depicts a water sorption/desorption isotherm result from a measurement of a sample containing Forms A and C taken at 25° C. in accord with an embodiment of the invention.

A single crystalline form of the Citrate Salt is also characterized by the curves of FIG. 15, corresponding to two consecutive water sorption/desorption cycles performed at 25° C. on a sample that includes Forms A and C, consistent with an embodiment of the invention. The graphs depict the percent change in mass, on a dry crystal basis, of the crystal as a function of relative humidity. Form C is characterized by being stable over a range of relative humidity from 0% to 90% as indicated by the overlap of the curves (i.e., the sorption phenomena is reversible with respect to the sample). XRPD scans of the sample before and after the sorption/desorption cycling show no structural modification (i.e., the proportion of Form A to Form C crystals is judged to be constant). Thus, the XRPD scans further characterize the stability of Form C over the relative humidities tested.

Form D

Figure 16:
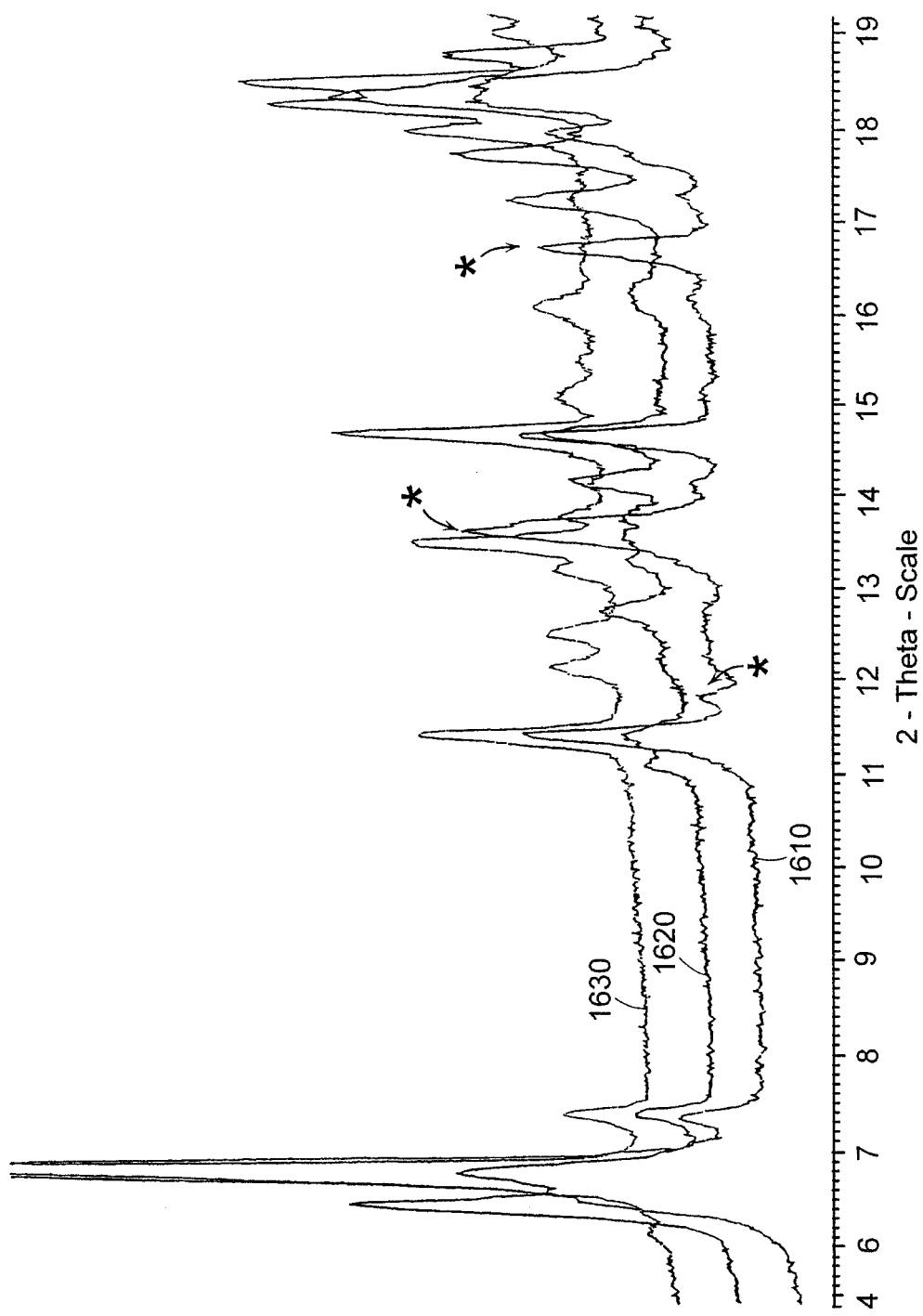
FIG. 16 depicts a X-ray powder diffraction patterns from measurements using CoK$\alpha_1$ ($\lambda$=1.7890 Å) and CoK$\alpha_2$ (λ=1.7929 Å) radiation on a sample of Form A, a sample containing Forms A and C, and a sample containing Forms A and D, consistent with an embodiment of the invention.

Some embodiments of the invention are directed to a crystalline Citrate Salt including Form D. In particular, Form D is characterized by features of XRPD measurements performed with CoKα$_1$ (λ=1.7890 Å) and CoKα$_2$ (λ=1.7929 Å) radiation as shown in FIG. 16. Scans 1610, 1620, 1630 graph the relative intensity as a function of 2θ for three samples. Scan 1610 corresponds to a sample of Forms A and D. Scans 1620, 1630, corresponding to samples of a combination of Forms A and C and pure Form A, respectively, are used to derive the unique features of scan 1610 corresponding with Form D. In one embodiment, Form D is characterized by any number of the peaks designated with a * on scan 1610 of FIG. 16.

Figure 17:
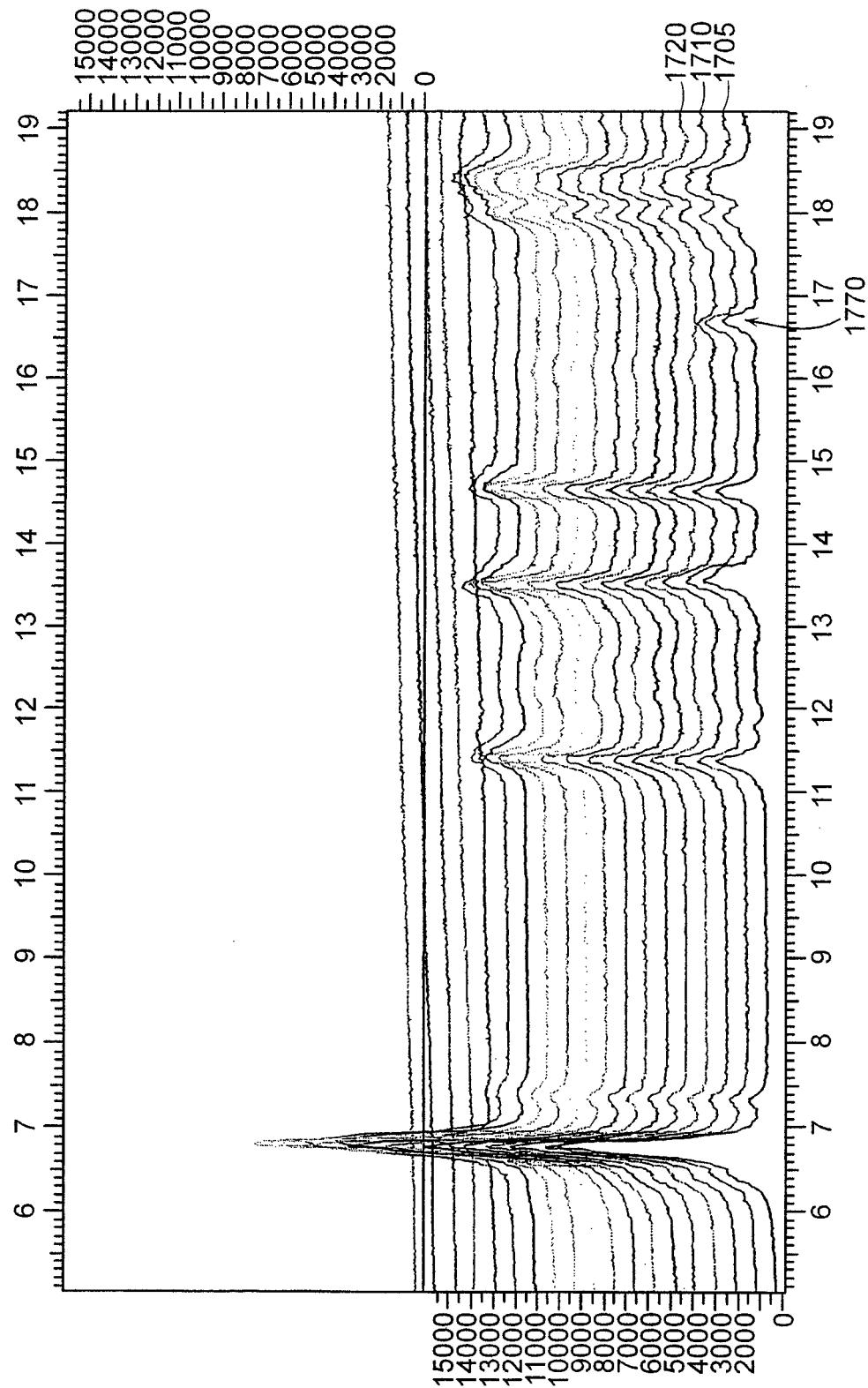
FIG. 17 depicts isothermal X-ray powder diffraction patterns from measurements using CoKα$_1$ (λ=1.7890 Å) and CoKα$_2$ (λ=1.7929 Å) radiation on a sample containing Forms A and D taken at temperatures from ambient to 210° C. at intervals of 10° C., in accord with an embodiment of the invention.

Form D is characterized by a loss of stability between 40° C. and 50° C. as observed by temperature controlled XRPD measurements. FIG. 17 presents isothermal XRPD measurements on sample containing Forms A and D at temperatures from ambient to 210° C., in steps of 10° C. in a dry nitrogen environment. For scans representing temperatures of 40° C. and lower (scan 1705 of FIG. 17 corresponding to T=40° C.), at least one characteristic line 1770 is present that is indicative of the presence of Form D. The scan 1710 representative of T=50° C. shows a diminishing of the line 1770. By T=60° C., the scan 1720 does not show the line 1770 characteristic of Form D. At this point, the sample has an XRPD scan resembling Form A. Thus, Form D is also characterized by a transition to Form A below 60° C., and a loss of stability of Form D below 50° C. The remaining scans show features at various temperatures that are indicative of Form A.

Figure 18:
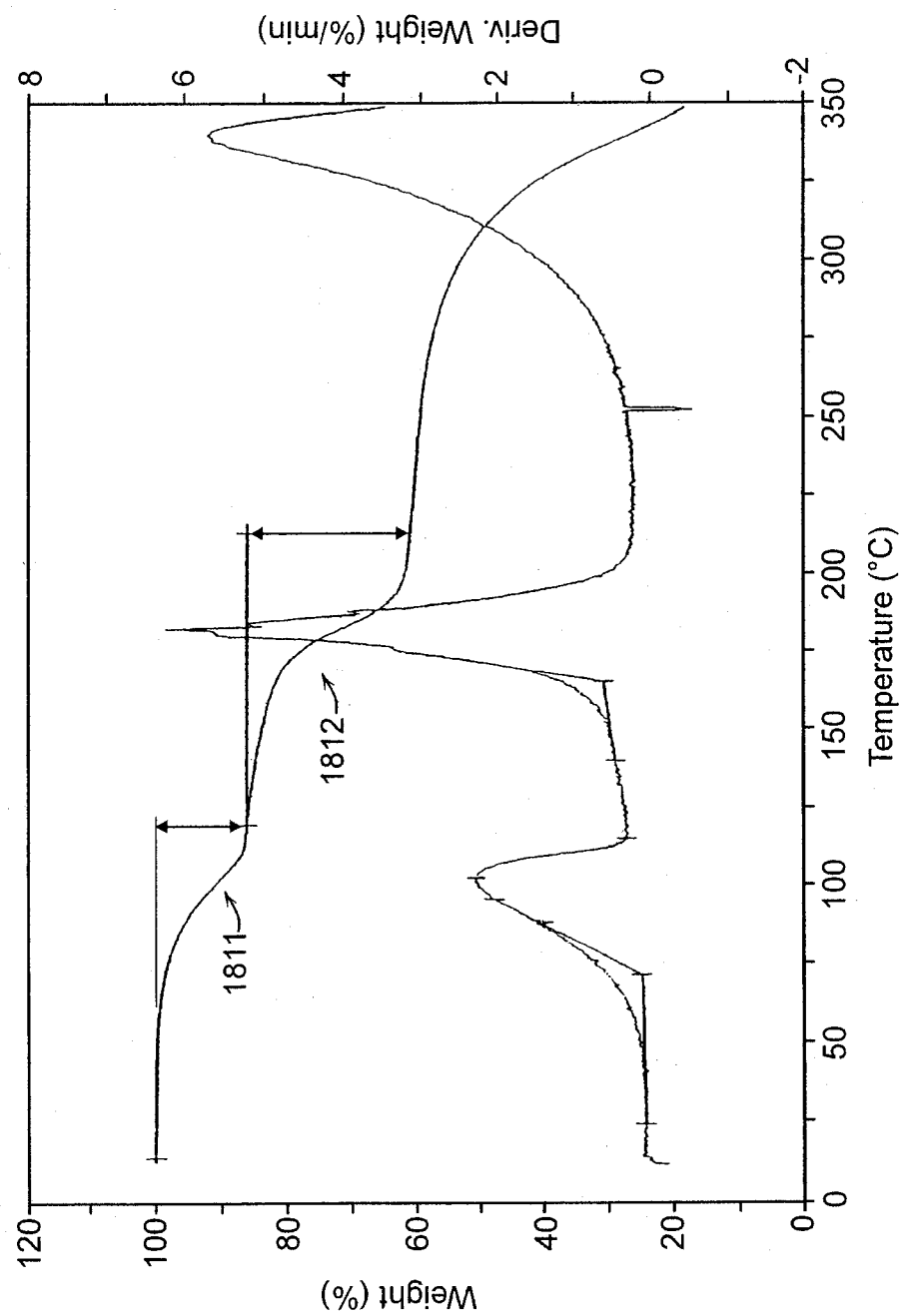
FIG. 18 depicts a thermal gravimetric analysis result from a measurement of a sample containing Forms A and D taken at a heating rate of 5° C./min in accord with an embodiment of the invention.

Form D is also characterized by the TGA measurement result shown in FIG. 18; the measurement is performed with a heating rate of 5° C./min on a sample containing Forms A and D. In particular, Form D is characterized as being anhydrous since the first weight loss transition 1811 begins above the temperature at which the Form D crystals interconvert to Form A according to the temperature controlled XRPD measurements. Rather the first weight loss is corresponds with the loss of THF from the crystals of the sample; this result is confirmed by simultaneous DSC and TGA coupled to mass spectrometry analysis. A second weight loss transition 1812 is observed with an interpolated beginning temperature of 164° C., having a maximum weight loss rate at 180° C. This is similar to the transition observed by TGA for Form A. Thus, the result confirms the temperature-dependent XRPD result of the transformation of the crystalline Form D fraction into Form A at high temperatures.

Figure 19:
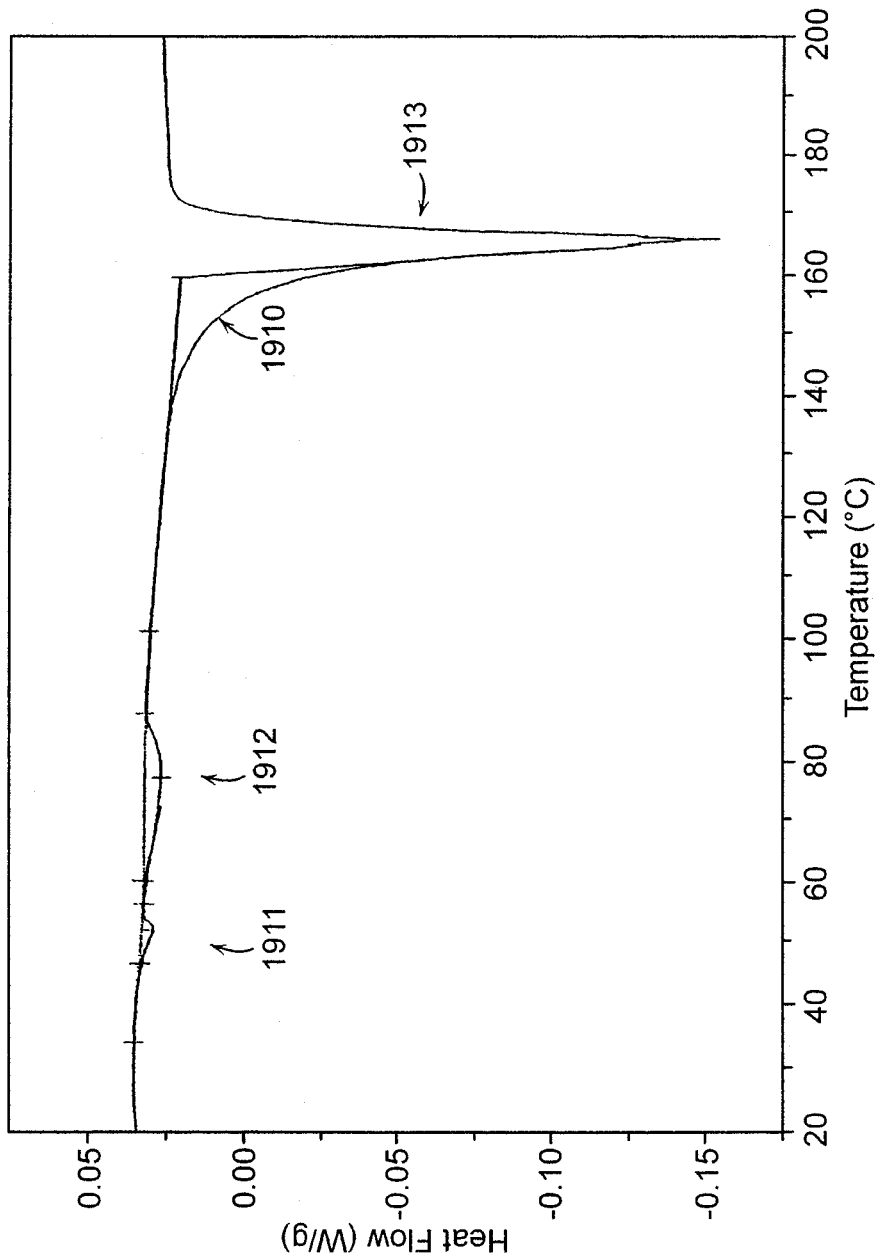
FIG. 19 depicts a differential scanning calorimetry result from a measurement of a sample containing Forms A and D taken at a heating rate of 0.3° C./min in accord with an embodiment of the invention.

A DSC measurement is also used to characterize Form D as shown in FIG. 19. The DSC measurement is performed on a mixture of Forms A and D of the Citrate Salt at a heating rate of 0.3° C./min The curve 1910 shows an endothermic transition 1911 interpolated to begin at about 47° C. and having a $T_{max}$=52° C.; this transition is corresponds with the conversion of crystalline Form D to Form A, and thus characterizes the crystalline form. The transition is also characterized by an integrated enthalpy of 3.7 J/g. The endothermic transition 1912, beginning at about 60° C. and having a $T_{max}$=77° C., corresponds with the release of THF as discussed in the TGA analysis. The enthalpy of the transition is integrated as 18.1 J/g. The endothermic transition 1913, interpolated to begin at about 160° C. and having a $T_{max}$=166° C., corresponds with the melting/decomposition of Form A.

Figure 20:
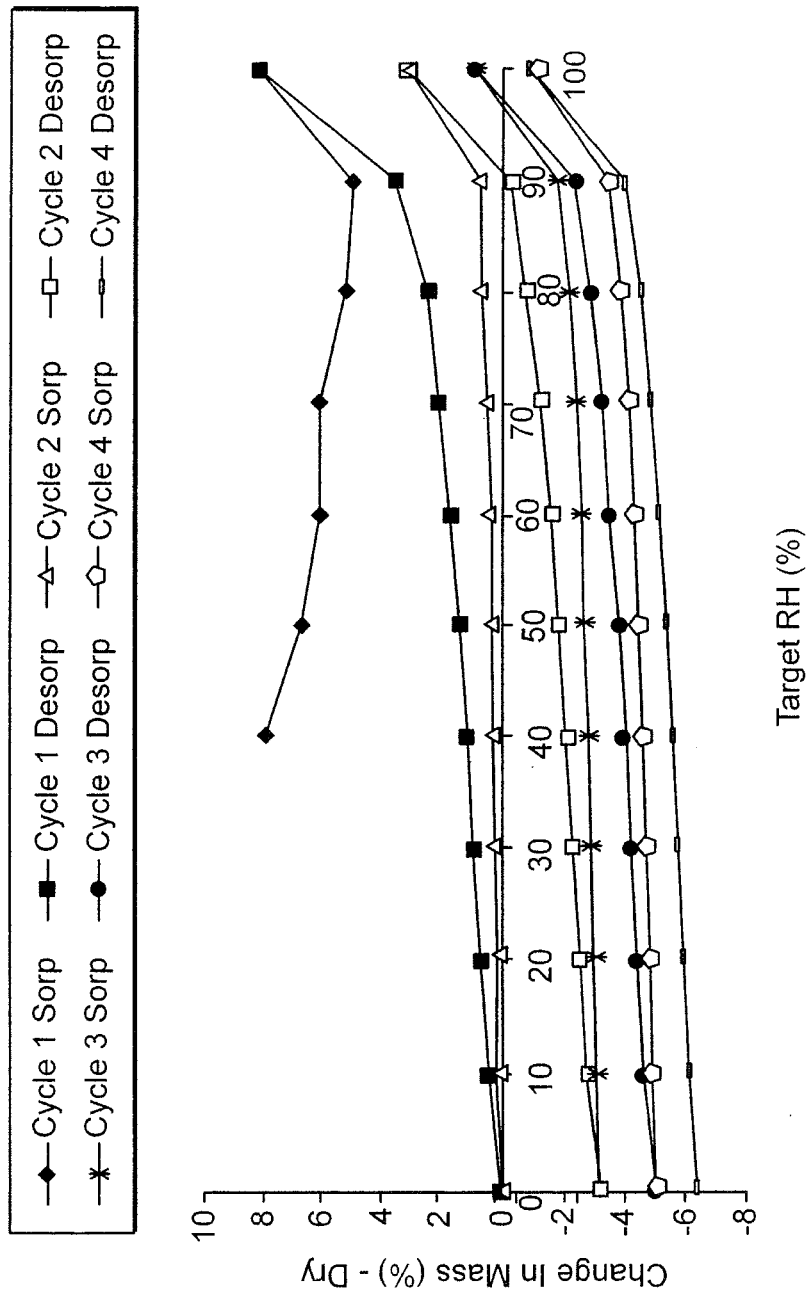
FIG. 20 depicts a water sorption/desorption isotherm result from a measurement of a sample containing Forms A and D taken at 25° C. in accord with an embodiment of the invention.

Form D is characterized by a loss of stability, and interconversion to Form A, after exposure to changes in relative humidity. FIG. 20 displays curves corresponding to four consecutive water sorption/desorption cycles performed at 25° C. on a sample containing Forms A and D. The curves depict the percent change in mass, on a dry crystal basis, of the crystal as a function of relative humidity. The sorption begins at 40% relative humidity, and is successively cycled between 100% relative humidity and 0% relative humidity. A hysteresis effect is observed with each humidification cycle, corresponding to a global weight loss of about 14.3% (w/w) after all 4 cycles.

XRPD measurements before and after the cycling show a structural modification in which the presence of Form D has disappeared after the cycling; only the signature of Form A remains.

Forms E and H

Form E is a single crystalline form of the Citrate Salt consistent with embodiments of the invention. A particular embodiment of the invention is directed toward the single crystalline form having a substantially similar XRPD pattern to what is displayed in FIG. 21. CuKα$_1$ radiation is used to generate the XRPD pattern. The single crystalline form is alternatively characterized by the first 30 lines of a XRPD pattern, as listed in Table 5 (the d spacing values given in angstroms).

TABLE 5

Figure 21:
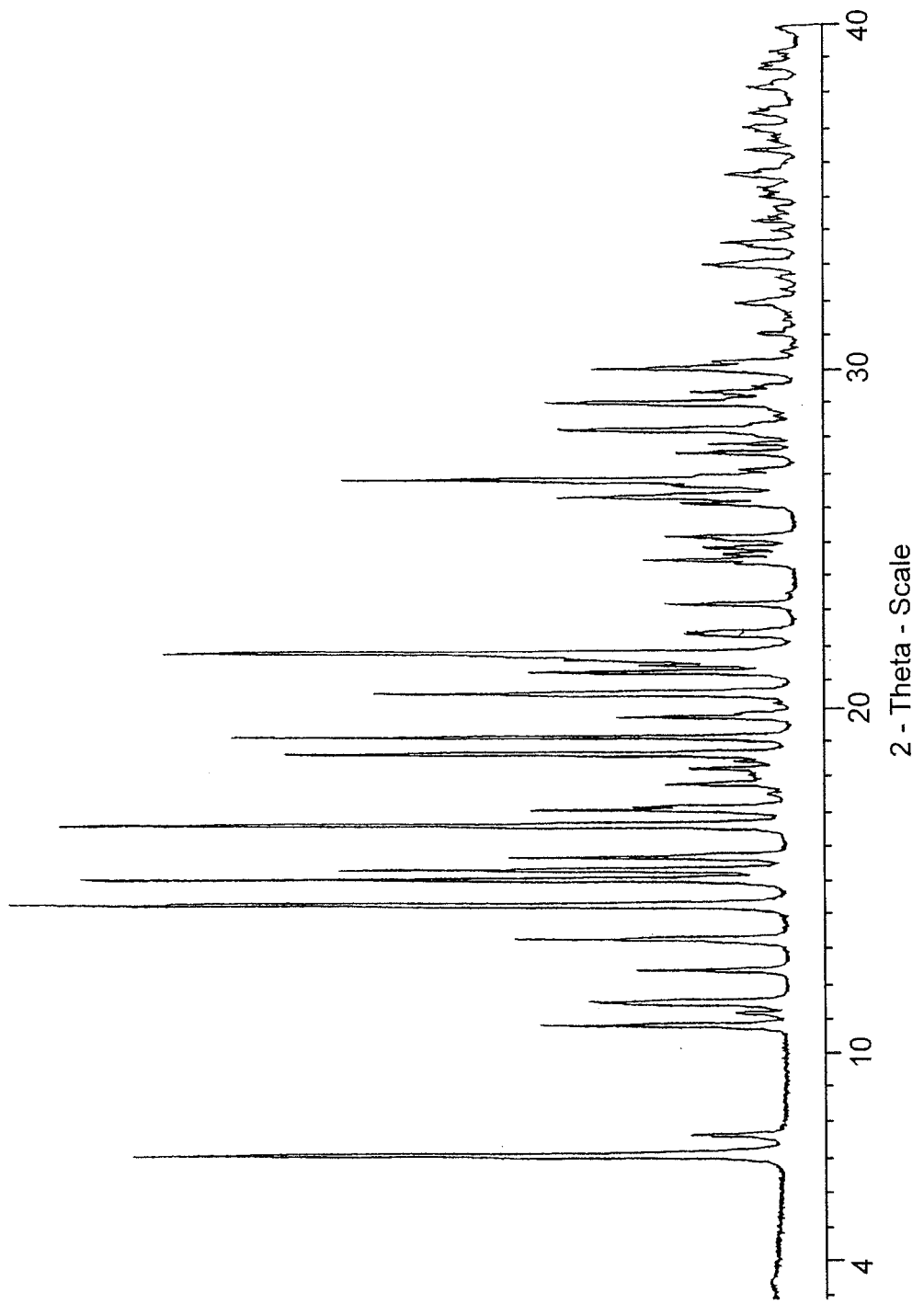
FIG. 21 depicts a X-ray powder diffraction pattern from a measurement on a sample of Form E using CuKα$_1$ radiation, consistent with an embodiment of the invention.

Indexing of XRPD Pattern of FIG. 21

| h | k | l | d-spacing | $2\theta$ $\lambda_{CuK\hat{a}}$ 1.54184 Å |
|---|---|---|---|---|
| 1 | 0 | 0 | 13.522 | 6.54 |
| 0 | 0 | 1 | 12.464 | 7.09 |
| −1 | 0 | 1 | 11.619 | 7.61 |
| −1 | 1 | 0 | 8.256 | 10.72 |
| 0 | 1 | 1 | 7.997 | 11.06 |
| 1 | 0 | 1 | 7.808 | 11.33 |
| −1 | 1 | 1 | 7.759 | 11.40 |
| −2 | 0 | 1 | 7.195 | 12.30 |
| −2 | 0 | 0 | 6.761 | 13.10 |
| −1 | 0 | 2 | 6.709 | 13.20 |
| 1 | 1 | 1 | 6.249 | 14.17 |
| 0 | 0 | 2 | 6.232 | 14.21 |
| −2 | 1 | 1 | 5.922 | 14.96 |
| −2 | 0 | 2 | 5.809 | 15.25 |
| −2 | 1 | 0 | 5.673 | 15.62 |
| −1 | 1 | 2 | 5.641 | 15.71 |
| 0 | 1 | 2 | 5.349 | 16.57 |
| 0 | 2 | 0 | 5.213 | 17.01 |
| 2 | 0 | 1 | 5.177 | 17.13 |
| −2 | 1 | 2 | 5.075 | 17.48 |
| 1 | 0 | 2 | 4.987 | 17.79 |
| −3 | 0 | 1 | 4.870 | 18.22 |
| −1 | 2 | 0 | 4.864 | 18.24 |
| 0 | 2 | 1 | 4.809 | 18.45 |
| −1 | 2 | 1 | 4.756 | 18.66 |
| 2 | 1 | 1 | 4.637 | 19.14 |
| −3 | 0 | 2 | 4.565 | 19.44 |
| 3 | 0 | 0 | 4.507 | 19.70 |
| 1 | 1 | 2 | 4.499 | 19.74 |
| −1 | 0 | 3 | 4.476 | 19.83 |

Form E is also characterized by one or more of the peaks in Table 5. Embodiments of the invention utilize any number of the listed peaks in Table 5 including the option of using all of them. In another alternate embodiment of the invention, Form E is characterized by one or more of the calculated cell parameters of Table 6, derived from analysis conducted on a XRPD measurement. The crystalline structure is also characterized to be orthorhombic P2$_1$ (Z=2 and Z'=1).

TABLE 6

Cell Parameters from XRPD Scan of Form E a = 14.612(3) Å
b = 10.425(1) Å
c = 13.469(2) Å
α = 90°
β = 112.27(1)°
γ = 90°
V = 1898.8 Å$^3$
Z = 2 and Z' = 1

Figure 22:
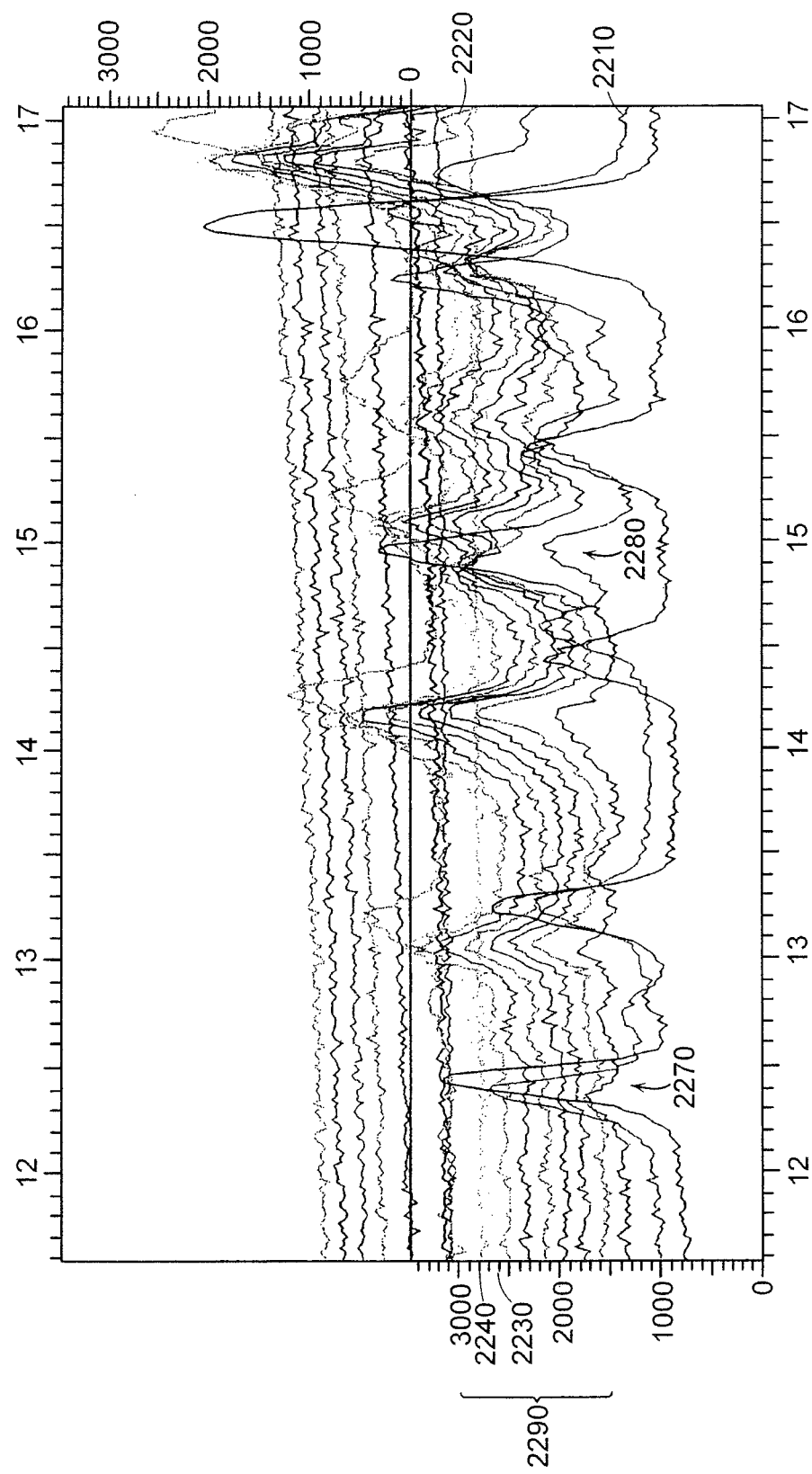
FIG. 22 depicts isothermal X-ray powder diffraction patterns from measurements on a sample of Form E using CoKα$_1$ (λ=1.7890 Å) and CoKα$_2$ (λ=1.7929 Å) radiation taken at temperatures from ambient to 210° C. at intervals of 10° C., in accord with an embodiment of the invention.

Isothermal XRPD measurements, using CoKα$_1$ (λ=1.7890 Å) and CoKα$_2$ (λ=1.7929 Å) radiation on a sample of Form E in a dry nitrogen environment, are presented in FIG. 22. The temperatures range from ambient temperature to 190° C. at intervals of 10° C.

In one embodiment of the invention, Form E is characterized by a loss of stability between 50° C. and 60° C. Scan 2210, corresponding to the XRPD at 40° C., shows particular lines (e.g., line 2270) beginning to disappear, while other lines (e.g., line 2280) start to grow. At 60° C. (scan 2220), the structure characteristic of Form E has disappeared. A new crystalline form of the Citrate Salt, designated Form H, is now present. The scan 2230 at 120° C. shows the beginnings of the destabilization of the crystalline Form H. The scan 2240 at 140° C. shows the that the sample has melted.

Thus, in another embodiment of the invention, Form H is characterized by each of the scans 2290 of FIG. 22 corresponding to temperatures between 60° C. and 130° C., and/or a loss of stability at a temperature between 130° C. and 140° C. It may also be characterized by the transition between Form E and Form H.

Figure 23:
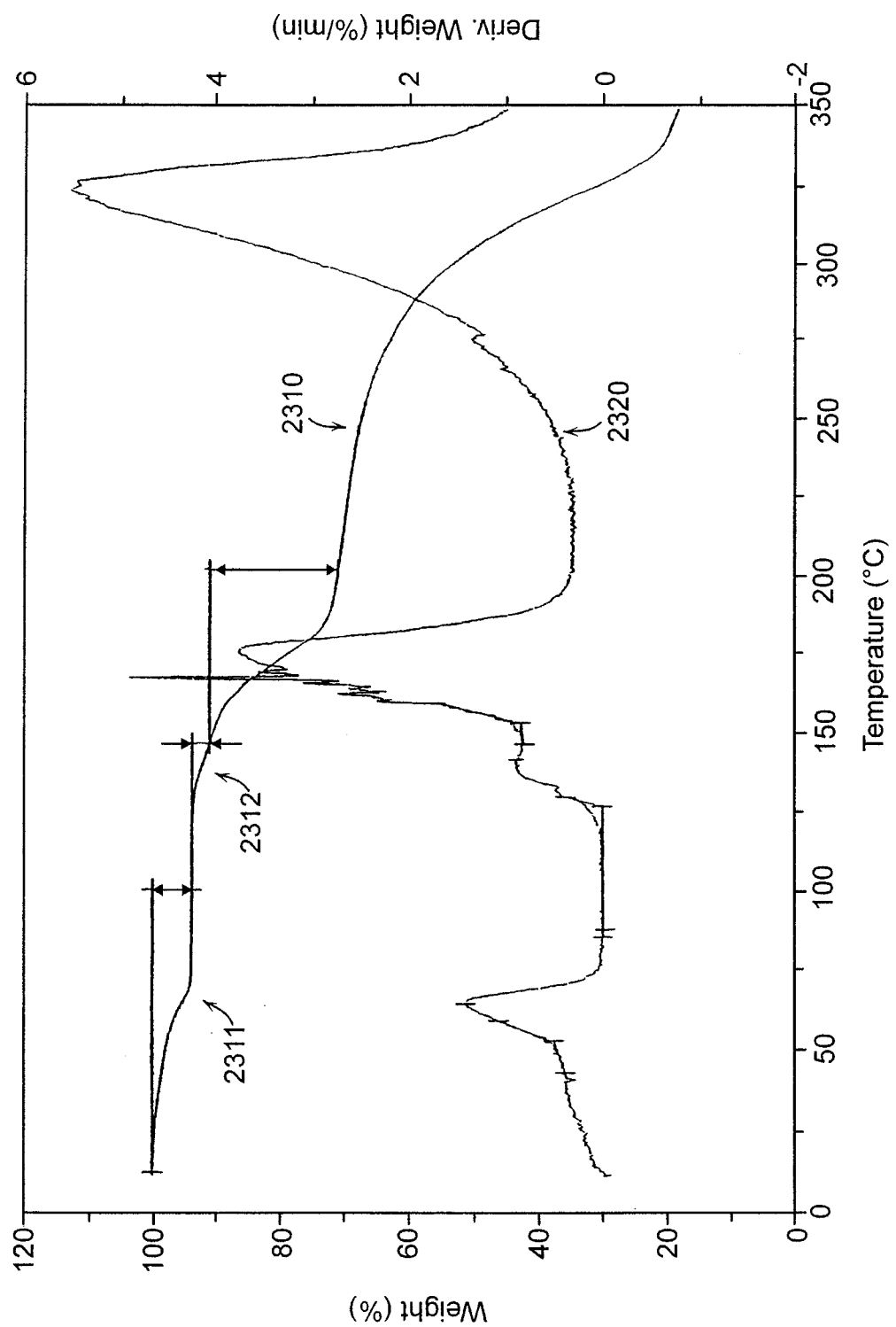
FIG. 23 depicts a thermal gravimetric analysis result from a measurement of a sample of Form E taken at a heating rate of 5° C./min in accord with an embodiment of the invention.

FIG. 23 shows the result of a TGA measurement on sample of crystalline Form E. The curve 2310 graphs the weight of the sample as a function of temperature; corresponding curve 2320 graphs the derived rate of weight loss as a function of temperature.

Form E is characterized by the weight loss transition 2311, in terms of the interpolated beginning temperature 52° C., the maximum rate of weight change temperature of 64° C., and/or the weight loss of 6.14% (w/w) associated with the transition. Form E is also characterized as a hydrated form of the Citrate Salt.

Form H of the Citrate Salt is characterized by the weight loss transition 2312, in terms of the interpolated beginning temperature of 127° C., the maximum rate of weight change temperature of 142° C., and/or the weight loss of 20.10% (w/w) associated with the transition. The transition 2311, as described above, also characterizes Form H.

Figure 24:
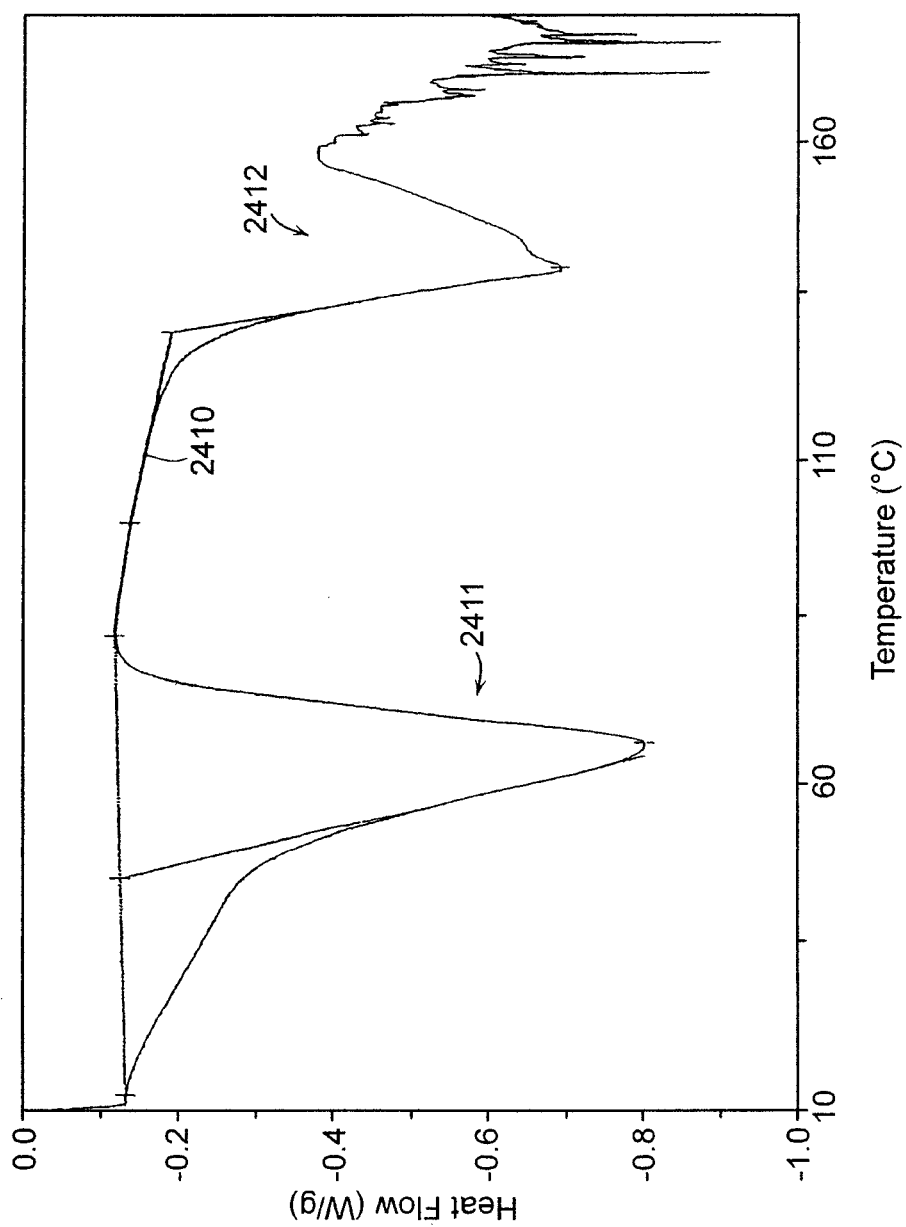
FIG. 24 depicts a differential scanning calorimetry result from a measurement of a sample of Form E taken at a heating rate of 5° C./min in accord with an embodiment of the invention.

FIG. 24 depicts the result of a DSC measurement on Form E of the Citrate Salt at a heating rate of 5° C./min. The curve 2410 graphs the heat flow into the sample as a function of temperature.

Form E is characterized by the endothermic transition 2411 of the curve 2410. The transition 2411 is characterized by an interpolated beginning temperature of 45° C., with the maximum rate of heat loss at T$_{max}$=67° C.; the integrated enthalpy change is calculated to be 178.3 J/g. The transition 2411 corresponds with loss of water in the sample, and the conversion of Form E to Form H (i.e., the loss of stability in Form E).

Form H is characterized by another endothermic transition 2412 of the curve 2410. The transition 2412 is characterized by an interpolated beginning temperature of 131° C., with the maximum rate of heat loss at T$_{max}$=141° C. The transition 2412 corresponds with the loss of water from Form H, and the decomposition/melting of the crystal. Transition 2411 also characterizes Form H.

Figure 25:
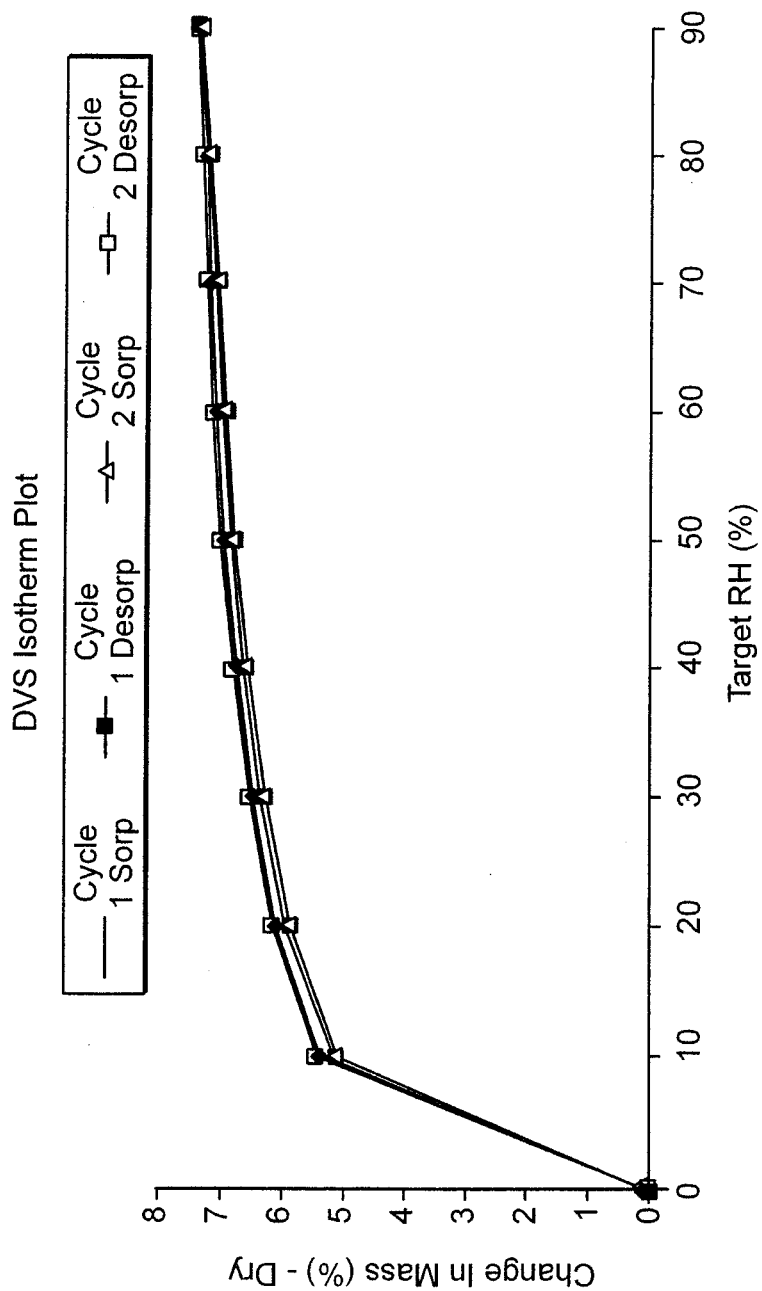
FIG. 25 depicts a water sorption/desorption isotherm result from a measurement of a sample of Form E taken at 25° C. in accord with an embodiment of the invention.

FIG. 25 shows curves corresponding to two consecutive water sorption/desorption cycles performed at 25° C. on a sample of Form E. The curves, depicting the percent change in mass on a dry crystal basis of the crystal as a function of relative humidity, overlap each other. This indicates that the sorption phenomena is reversible. The curves indicate the sample gains about 5.13% (w/w) as the relative humidity is increased from 0% to 10%. Between 10% and 90% relative humidity, the sample weight changes about 2.28% (w/w). XRPD measurements show that the crystal has a structure corresponding with Form E before the sorption/desorption cycles, and a structure corresponding with Form H after the cycling.

At ambient temperatures form E is stable from 10 to 90% relative humidity. Under 10% relative humidity, and as experimentally observed when exposed at 0% relative humidity, form E fully transforms into form H. As indicated by sorption/desorption curves, form H reversibly transforms into form E when exposed to 10% relative humidity or a higher relative humidity rate.

Forms F and G

Figure 26:
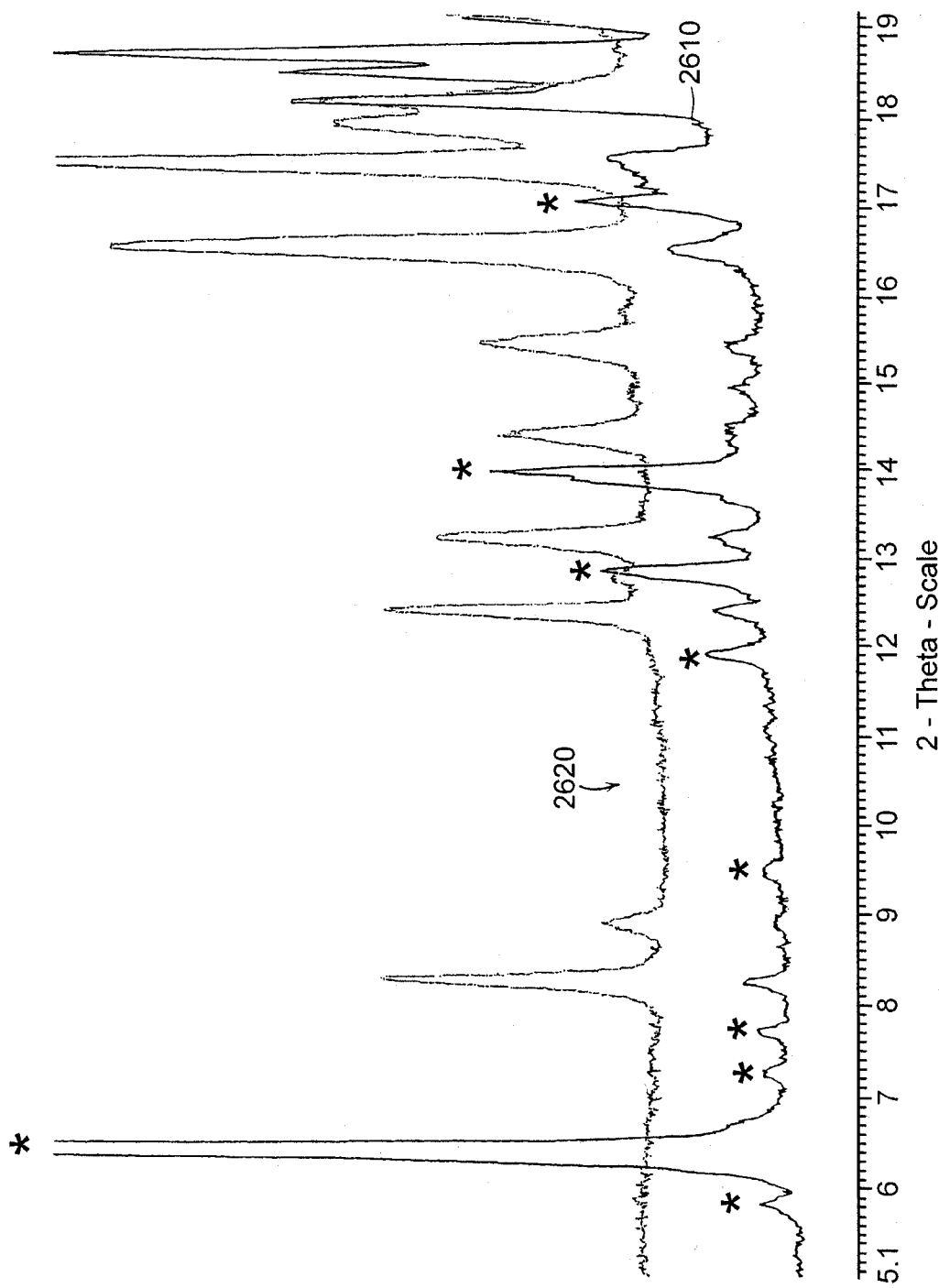
FIG. 26 depicts a X-ray powder diffraction patterns from measurements using CoKα$_1$ (λ=1.7890 Å) and CoKα$_2$ (λ=1.7929 Å) radiation on a sample of Form E and a sample containing Forms E, F, and G, consistent with an embodiment of the invention.

A crystalline containing a mixture of Forms F and G is characterized by any number of the lines identified by a * in the XRPD pattern of FIG. 26, in an embodiment of the invention. FIG. 26 presents the relative intensity as a function of 2θ for scans 3110, 3120 under dry nitrogen and ambient temperature using CoKα$_1$ (λ=1.7890 Å) and CoKα$_2$ (λ=1.7929 Å) radiation. Scan 2610 corresponds with a sample containing Forms E, F, and G. Scan 2620, corresponding with pure Form E, is used to distinguish the peaks of scan 2610 that are unique to Forms F and G.

Figure 27:
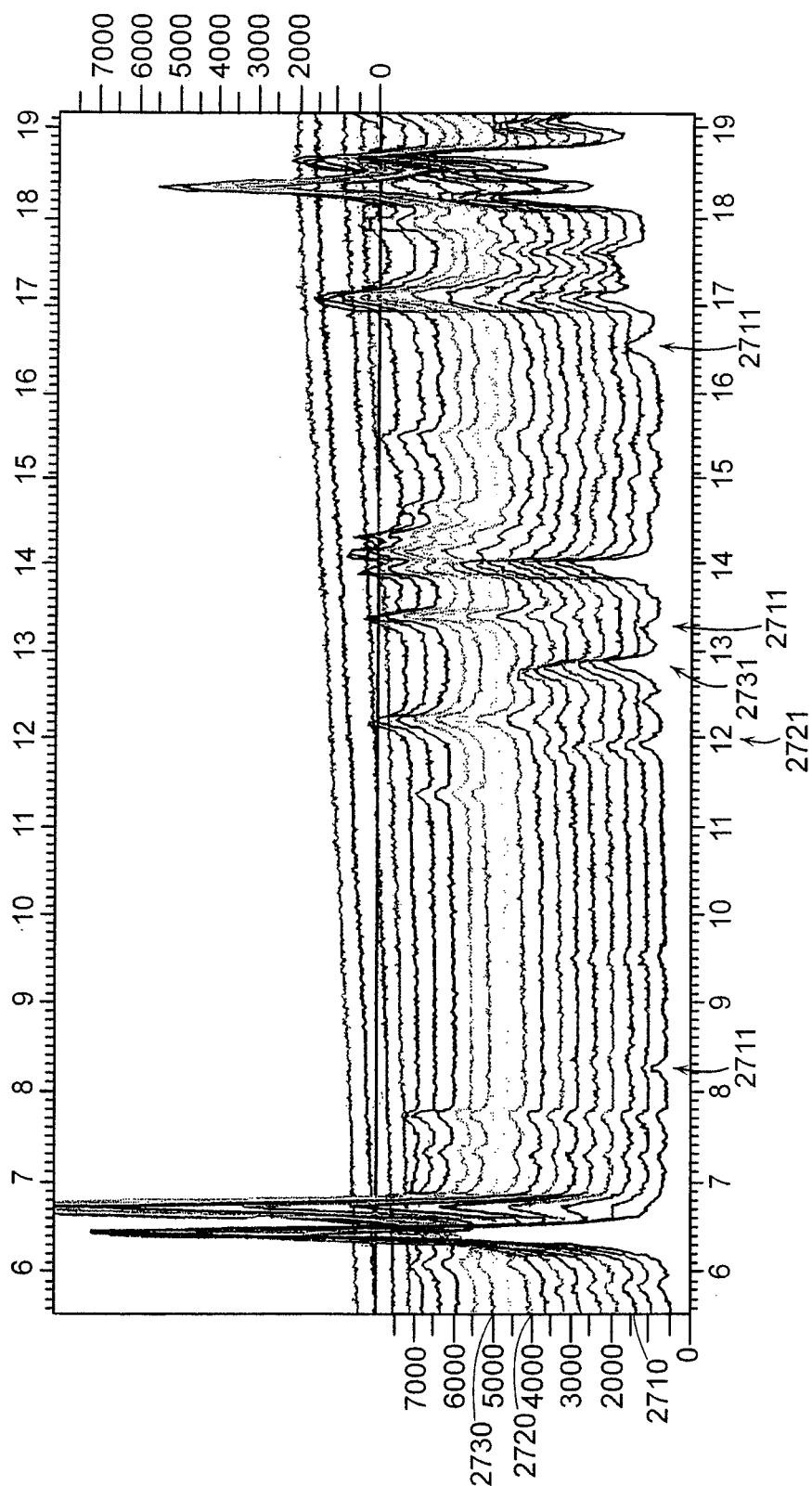
FIG. 27 depicts isothermal X-ray powder diffraction patterns from measurements using CoKα$_1$ (λ=1.7890 Å) and CoKα$_2$ (λ=1.7929 Å) radiation on a sample containing Forms E, F, and G taken at temperatures from ambient to 210° C. at intervals of 10° C., in accord with an embodiment of the invention.

FIG. 27 records isothermal XRPD measurements using CoKα$_1$ (λ=1.7890 Å) and CoKα$_2$ (λ=1.7929 Å) radiation on a sample containing Forms E, F, and G at temperatures from ambient to 210° C. in steps of 10° C. Each curve represents an isothermal scan of the sample in a dry nitrogen environment.

Form E is characterized by a loss of stability at temperatures above 50° C. The scan 2710, representing the measurement at 50° C., indicates that lines 2711 unique to Form E have disappeared at temperatures of 50° C. and higher. Scans with temperatures of 110° C. and higher show that lines unique to Form F (e.g., line 2721) have disappeared. Thus, Form F is characterized by a loss of stability of this form at temperatures greater than 110° C. (scan 2720 showing the measurement at 110° C.). Form G is characterized by a loss of stability at temperatures of 130° C. and higher; scans at temperatures of 130° C. 2730 and higher show lines corresponding with Form G have disappeared (e.g., line 2731).

Throughout the measurements as temperatures increase from ambient to 130° C., lines corresponding with Form B continue to grow in the various scans. At temperatures 130° C. and higher, the scans correspond substantially with the lines for Form B. Thus, the data from these scans indicates that each of Forms E, F, and G converts to Form B as the temperature is raised.

Figure 28:
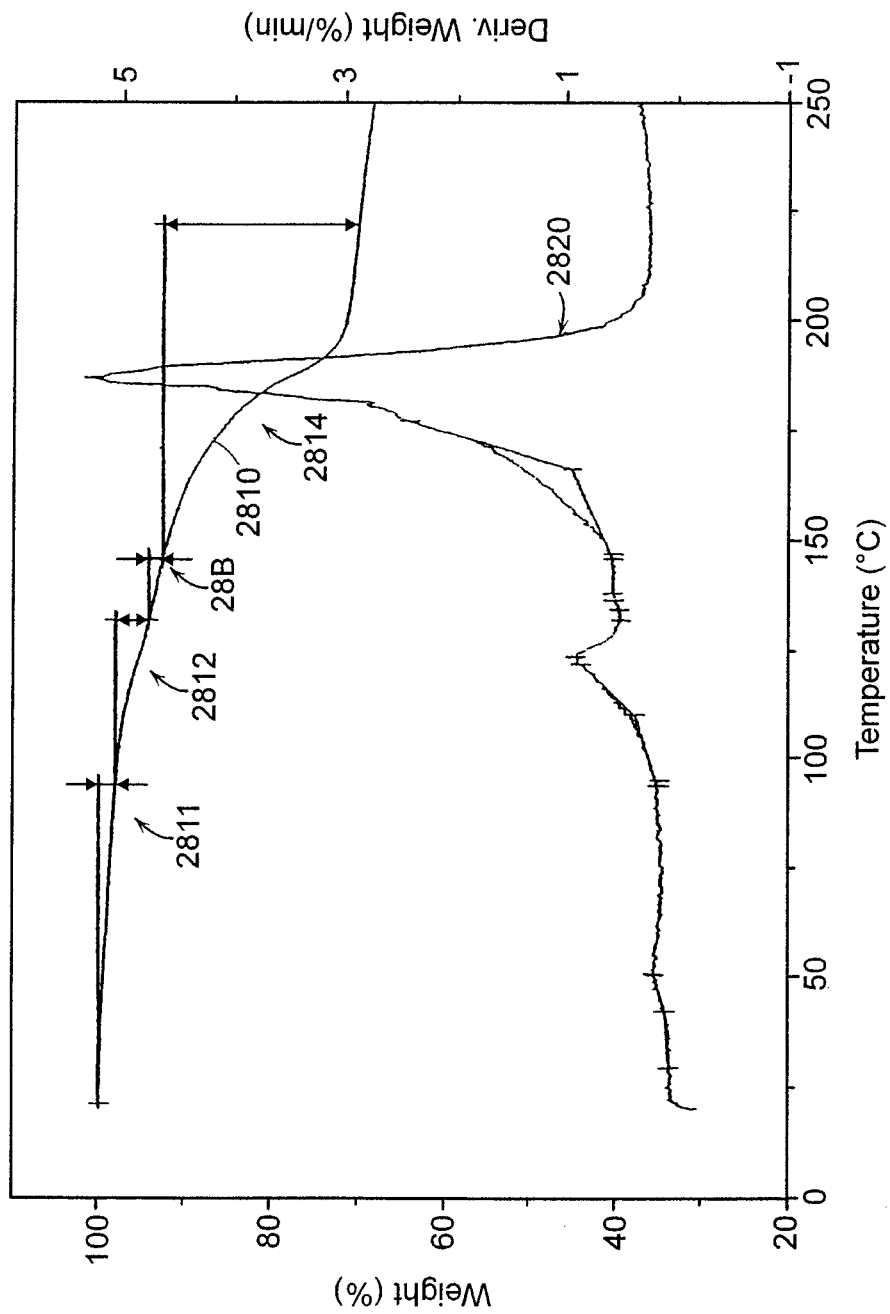
FIG. 28 depicts a thermal gravimetric analysis result from a measurement of a sample containing Forms E, F, and G taken at a heating rate of 5° C./min in accord with an embodiment of the invention.

A TGA measurement on a sample of containing Form E, F, and G is shown in FIG. 28. The curve 2810 records the weight of the sample as a function of temperature. Curve 2820 records the corresponding derived rate of weight loss as a function of temperature for a sample heated at 5° C./min. Four weight losses are observed in FIG. 28; the relevant data summarized in Table 7.

TABLE 7

Weight Transition Data for a TGA Measurement of a Sample Containing Form E, F, and G

| Weight Transition (label in FIG. 28) | Interpolated Starting T (° C.) | T (° C.) corresponding to Max. Rate of Weight Change | Weight Loss % (w/w) |
|---|---|---|---|
| 2811 | 42 | 50 | 1.9 |
| 2812 | 110 | 123 | 3.6 |
| 2813 | 131 | 138 | 1.6 |
| 2814 | 166 | 187 | 22.6 |

Form E is characterized by the weight loss 2811, which corresponds with the conversion away from Form E. Form F is characterized by the weight loss 2812, which corresponds with the conversion away from Form F. Form G is characterized by the weight loss 2813, which corresponds with the conversion away from Form G. The fourth weight loss 2814 is the decomposition/melting of crystalline Form B, and the corresponding loss of citrate.

Figure 29:
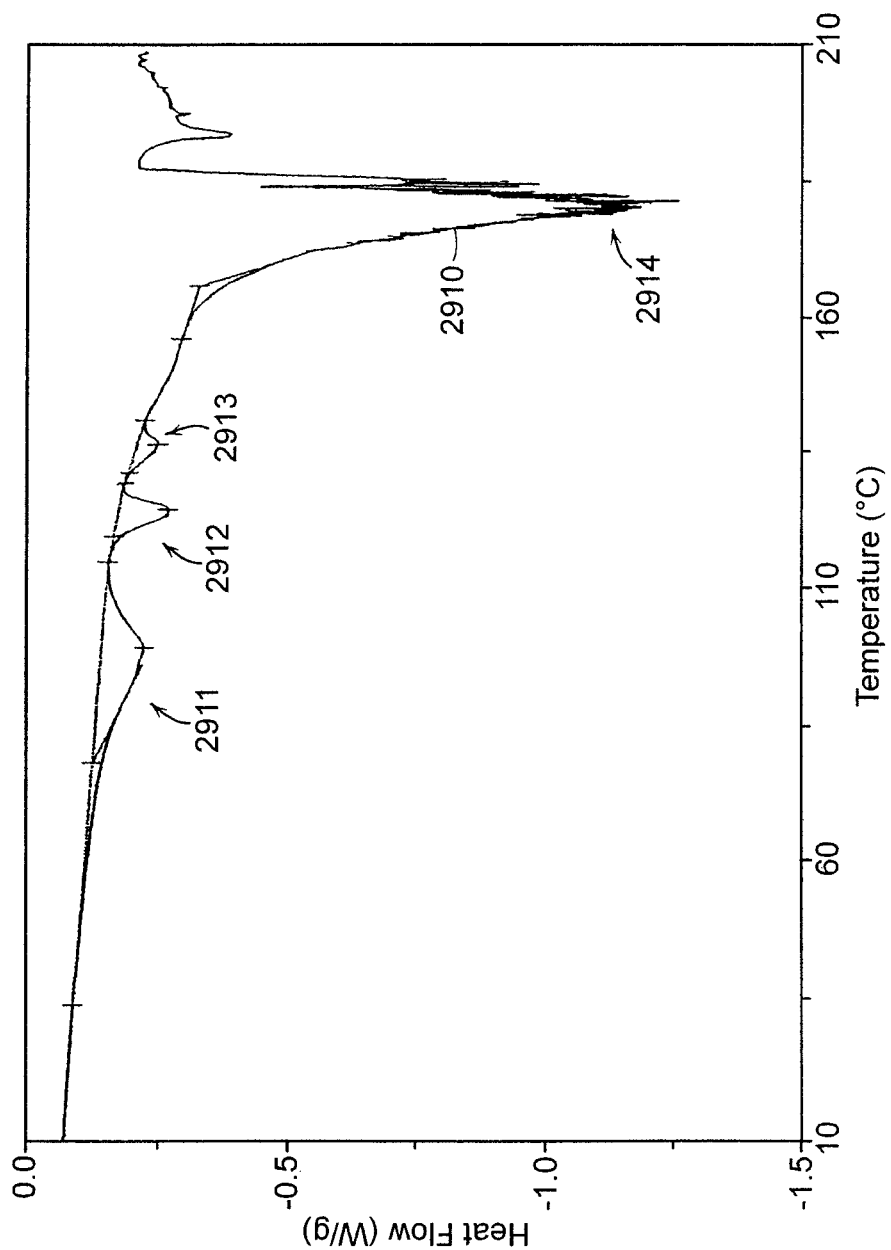
FIG. 29 depicts a differential scanning calorimetry result from a measurement of a sample containing Forms E, F, and G taken at a heating rate of 5° C./min in accord with an embodiment of the invention.

FIG. 29 presents the result of a DSC measurement on sample containing Forms E, F, and G at a heating rate of 5° C./min. The curve 2910 shows four endothermic transitions, the quantitative data summarized in Table 8.

TABLE 8

Heat Flow Transition Data for a DSC Measurement of a Sample Containing Form E, F, and G

| Transition (label in FIG. 34) | Interpolated Starting T (° C.) | T$_{max}$ (° C.) | Integrated Enthalpy Change (J/g) |
|---|---|---|---|
| 3411 | 78 | 99 | 20.3 |
| 3412 | 119 | 124 | 5.8 |
| 3413 | 131 | 136 | 2.4 |
| 3414 | 165 | 181 | N/A |

The first endothermic transition 2911 characterizes the conversion of crystals with Form E to Form B. The second endothermic transition 2912 characterizes the conversion of crystals with Form F to Form B. The third endothermic transition 2913 characterizes the conversion of crystals with Form G to Form B. The fourth endothermic transition 2914 characterizes the decomposition/melting of crystalline Form B.

Figure 30:
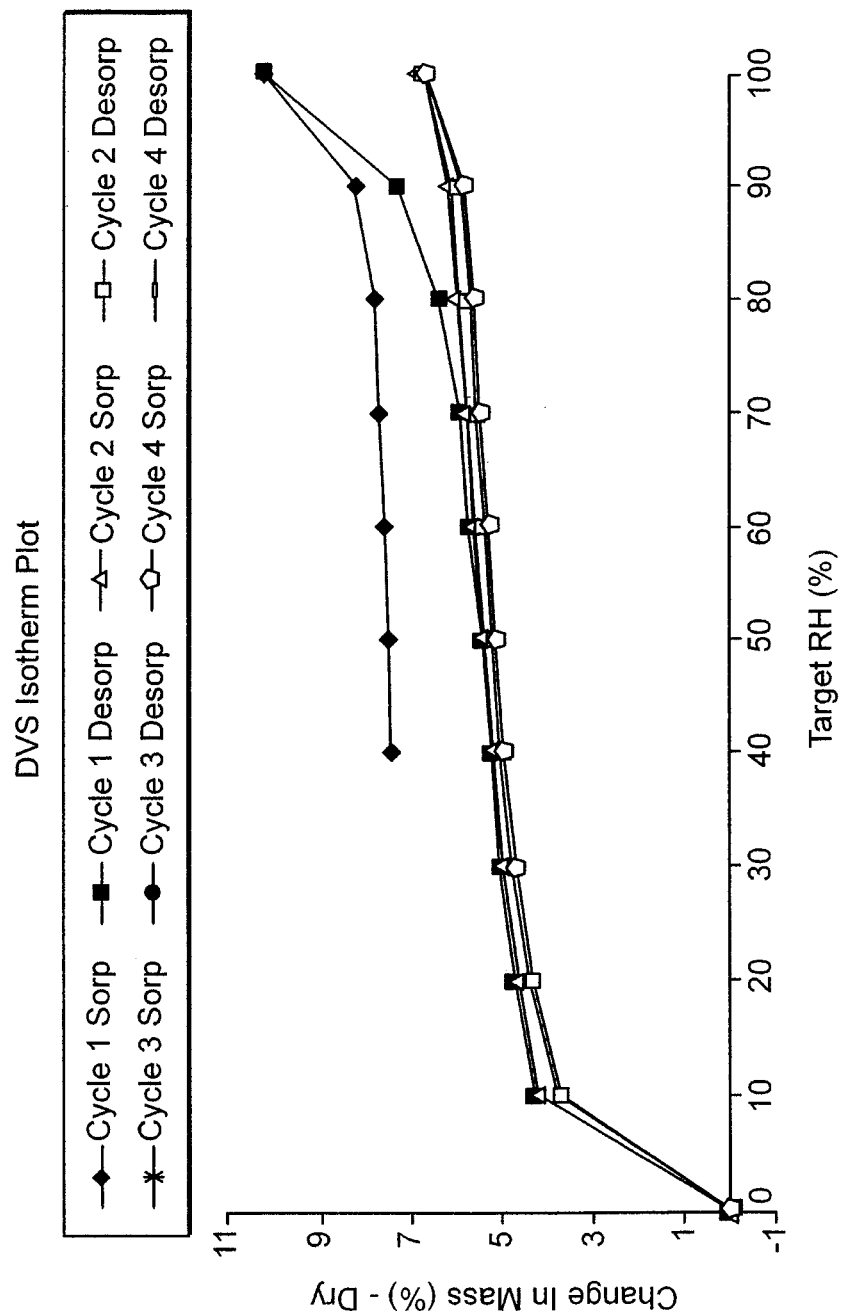
FIG. 30 depicts a water sorption/desorption isotherm result from a measurement of a sample containing Forms E, F, and G taken at 25° C. in accord with an embodiment of the invention.

FIG. 30 displays curves corresponding to four consecutive water sorption/desorption cycles performed at 25° C. on a sample containing Forms E, F, and G. The graphs depict the percent change in mass, on a dry crystal basis, of the crystal as a function of relative humidity. The first sorption run begins at 40% relative humidity, and is successively cycled between 100% relative humidity and 0% relative humidity. A hysteresis effect is observed for the first sorption/desorption cycle; the remaining 3 cycles being reversible and not displaying hysteresis. The net weight loss in the sample after sorption/desorption cycling with water is about 7.5% (w/w), which is similar to the total of the three weight transitions observed from the TGA analysis of FIG. 28 at the lower temperatures. Thus, heating the cycled sample to a temperature of about 131° C. or higher will convert the sample to anhydrous Form B.

Subjecting the sample to a change in relative humidity from 0% to 10% results in a water uptake corresponding to 3.76% (w/w). A change in relative humidity from 10% to 90% results in a water uptake corresponding to 2.10% (w/w). A change in relative humidity from 90% to 100% results in a water uptake corresponding between about 0.82% (w/w) to about 0.93% (w/w). These changes are all reversible.

XRPD measurements taken of the sample at 40% relative humidity before and after the sorption/desorption cycling show that Form F disappears and the lines of Form G have dissipated, while Form E lines grow, after the cycling is performed. The sorption/desorption weight changes between 10% and 90% relative humidity are similar to what is witnessed for Form E (c.f. FIG. 25). Thus, humidification cycling results in the conversion of Forms F and G to Form E.

The same change of the loss of lines of Form F and diminution of lines of Form G, while the lines of Form E grow, is witnessed when comparing XRPD of batch F1 before and after the sample is subjected to a relative humidity of 97.5% for about one month, or before and after the sample is rinsed with water.

XRPD measurements made on a sample of batch F1 subject to a relative humidity of 0% for about one month show a mixture of Forms E and B; total conversion to Form B is not observed.

Other embodiments of the invention are directed to a single crystalline form of the Citrate Salt characterized by a combination of the aforementioned characteristics of any of the single crystalline forms discussed herein. The characterization may be by any combination of one or more of the XRPD, TGA, DSC, and water sorption/desorption measurements described for a particular polymorph. For example, the single crystalline form of the Citrate Salt may be characterized by any combination of the XRPD results regarding the 2θ position of the major peaks in a XRPD scan; any combination of one or more of the cell parameters derived from a XRPD scan; and the temperature at which a crystalline form begins to destabilize, or decomposes/melts, as determined from XRPD scans of a sample of the crystalline form taken at different temperatures. The single crystalline form of the Citrate Salt may also be characterized by TGA determinations of the temperature at which a sample begins to undergo a weight loss transition and/or the temperature corresponding with the rate of maximum weight change during a weight loss transition. DSC determinations of $T_{max}$ and/or the temperature at which a sample begins to undergo a heat flow transition may also characterize the crystalline form. Weight change in a sample and/or change in sorption/desorption of water per molecule of anhydrous Citrate Salt as determined by water sorption/desorption measurements over a range of relative humidity (e.g., 0% to 90%) may also characterize a single crystalline form of the Citrate Salt.

Examples of combinations of single crystalline form characterizations using multiple analytical techniques include the 2θ location of at least one of the major peaks of a XRPD scan and the $T_{max}$ in a heat flow transition/endothermic transition observed by a corresponding DSC measurement; the location of at least one of the major peaks of a XRPD scan and the temperature at which a maximum rate of weight change is noticed for a weight loss transition in a corresponding TGA measurement; the 2θ location of at least one of the major peaks of a XRPD scan, the $T_{max}$ in a heat flow transition/endothermic transition observed by a corresponding DSC measurement, and the temperature at which a maximum rate of weight change is noticed for a weight loss transition in a corresponding TGA measurement; and the 2θ location of at least one of the major peaks of a XRPD scan, the $T_{max}$ in a heat flow transition/endothermic transition observed by a corresponding DSC measurement, the temperature at which a maximum rate of weight change is noticed for a weight loss transition in a corresponding TGA measurement, and the change in sorption/desorption of water per molecule of anhydrous salt as determined by water sorption/desorption measurements over a range of relative humidity. As well, each of the aforementioned examples may replace the use of the 2θ location of at least one of major peaks of a XRPD scan with one or more cell parameters of the single crystalline form, as determined from a XRPD scan, in consistent embodiments of the invention.

The combinations of characterizations that are discussed above may be used to describe any of the polymorphs of the Citrate Salt discussed herein (e.g., Form A, B, C, D, E, F, G, or H). In an alternative embodiment of the invention, a crystalline Citrate Salt, or a single crystalline form of the Citrate Salt, is characterized by the lack of one or more properties associated with a particular polymorph (e.g., not being Form A, not having a $T_{max}=167°$ C. when measured by DSC with a heating rate of 1° C./min, not having at least one of the major peaks of Form A as measured by XRPD). In another alternative embodiment of the invention, a crystalline Citrate Salt is characterized using a combination of the single crystalline form characterizations of different polymorphs (e.g., a crystalline form comprising Form A and Form B; a crystalline form characterized by have at least one of the major peaks listed for Form A and Form B from XRPD measurements; the crystalline form is anhydrous). Other alternative embodiments of the invention relate to a crystalline Citrate Salt characterized by not having a combination of single crystalline form characterizations of different polymorphs (e.g., a crystalline Citrate Salt not having the major peaks of XRPD patterns associated with Forms A, C, and D).

Certain other exemplary embodiments are described directly below.

In some embodiments, at least 10% by weight of the citrate salt of (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol ("Citrate Salt") is crystalline. In other embodiments, at least 70% by weight of the Citrate Salt is crystalline. In still other embodiments, at least 90% by weight of the Citrate Salt is crystalline.

In other embodiments, at least 10% by weight of the Citrate Salt is a single crystalline form. In yet other embodiments, at least 70% by weight of the Citrate Salt is a single crystalline form. In still other embodiments, at least 90% by weight of the Citrate Salt is a single crystalline form.

In other embodiments, at least 10% by weight of the Citrate Salt is other than Form A. In still other embodiments, at least 70% by weight of the Citrate Salt is other than Form A. In yet other embodiments, at least 90% by weight of the Citrate Salt is other than Form A.

In other embodiments, a citrate salt of (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol is provided, the citrate salt being substantially Form A. In still other embodiments, a citrate salt of (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol is provided the citrate salt being at least 10% by weight Form A. In yet other embodiments, a citrate salt of (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol is provided, the citrate salt being at least 70% by weight Form A.

In still other embodiments, the Citrate Salt is at least 70% by weight a single crystalline form and the crystalline form is characterized by at least one of the x-ray powder diffraction peaks at 2θ angles of 9.8, 11.7, 12.6, 15.5, 15.7, 15.9, 17.3, 17.5, 18.2, 19.0, and 19.7, when measured with CuKα$_1$ radiation. In other embodiments, the Citrate Salt is at least 70% by weight a single crystalline form and the crystalline form is characterized by x-ray powder diffraction peaks at 2θ angles of 9.8, 11.7, 12.6, 15.5, 15.7, 15.9, 17.3, 17.5, 18.2, 19.0, and 19.7, when measured with CuKα$_1$ radiation. In still other embodiments, the single crystalline form is characterized by a x-ray powder diffraction pattern substantially similar to FIG. 1 when measured with CuKα$_1$ radiation. In yet other embodiments, the single crystalline form is characterized by having a stability transition in the range of 150° C. and 160° C. as observed with controlled temperature x-ray powder diffraction.

In other embodiments, at least 70% by weight of the Citrate Salt is a single crystalline form, wherein the single crystalline form is characterized by a $T_{max}$ of 167° C.±3° C. during an endothermic transition observed by differential scanning calorimetry using a scanning rate of 1° C./minute. In still other embodiments, at least 70% by weight of the Citrate Salt is a single crystalline form, wherein the single crystalline form is characterized by a weight loss observed by thermal gravimetric analysis corresponding to decomposition of the citrate salt beginning at 164° C.±3° C. In still other embodiments, at least 70% by weight of the Citrate Salt is a single crystalline form, wherein the single crystalline form gains about 0.8 moles of water per mole of citrate salt over a relative humidity change from 0% to 90% at 25° C.

In still other embodiments, a citrate salt of (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol is provided, the citrate salt being substantially Form B. In yet other embodiments, a citrate salt of (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol is provided, the citrate salt being at least 10% by weight Form B. In still other embodiments, at least 70% by weight of the Citrate Salt is a single crystalline form, wherein the single crystalline form is Form B. In yet other embodiments, at least 70% by weight of the Citrate Salt is a single crystalline form, wherein the single crystalline form is characterized by at least one of the x-ray powder diffraction peaks at 2θ angles of 10.6, 11.6, 12.3, 14.8, 15.8, 16.1, 16.7, 18.8, 20.6, 21.7, and 24.5, when measured with CuKα₁ radiation. In yet other embodiments, at least 70% by weight of the Citrate Salt is a single crystalline form, wherein the single crystalline form is characterized by x-ray powder diffraction peaks at 2θ angles of 10.6, 11.6, 12.3, 14.8, 15.8, 16.1, 16.7, 18.8, 20.6, 21.7, and 24.5, when measured with CuKα₁ radiation. In still other embodiments, the single crystalline form is characterized by a x-ray powder diffraction pattern substantially similar to FIG. 6 when measured with CuKα₁ radiation. In yet other embodiments, the single crystalline form is characterized by having a stability transition in the range of 170° C. and 180° C. as observed with controlled temperature x-ray powder diffraction.

In yet other embodiments, at least 70% by weight of the Citrate Salt is a single crystalline form, wherein the single crystalline form is characterized by a $T_{max}$ of 179° C.±3° C. during an endothermic transition observed by differential scanning calorimetry using a scanning rate of 1° C./minute. In yet other embodiments, at least 70% by weight of the Citrate Salt is a single crystalline form, wherein the single crystalline form is characterized by a weight loss observed by thermal gravimetric analysis corresponding to decomposition of the citrate salt beginning at 180° C.±3° C. In yet other embodiments, at least 70% by weight of the Citrate Salt is a single crystalline form, wherein the single crystalline form gains about 0.4 moles of water per mole of citrate salt over a relative humidity change from 0% to 90% at 25° C.

Pharmaceutical Compositions

In another aspect, the present invention provides a pharmaceutical composition comprising a pharmaceutically acceptable carrier or diluent; and a citrate salt of (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol as discussed herein. In some embodiments, the Citrate Salt is substantially crystalline.

The present invention also provides a pharmaceutical composition comprising pharmaceutically acceptable carrier or diluent; and citrate salt of (S)-4-(4-Chloro-phenyl)-1-{3-[7-(1-hydroxy-1-methyl-ethyl)-1H-10-oxa-1-aza-dibenzo[a,d]cyclohepten-5-ylidene]-propyl}-3,3-dimethyl-piperidin-4-ol, wherein at least 10% by weight of the citrate salt is crystalline. In some embodiments, at least 10% by weight of the citrate salt is a single crystalline form. In still other embodiments, at least 10% by weight of the citrate salt is other than Form A.

The present invention further provides a pharmaceutical composition comprising a pharmaceutically acceptable carrier or diluent; and a citrate salt of (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol, wherein at least 70% by weight of the citrate salt is crystalline. In some embodiments, at least 70% by weight of the citrate salt is a single crystalline form. In other embodiments, at least 70% by weight of the citrate salt is other than Form A. In yet other embodiments, the single crystalline form is Form A. In still other embodiments, the single crystalline form is characterized by at least one of the x-ray powder diffraction peaks at 2θ angles of 9.8, 11.7, 12.6, 15.5, 15.7, 15.9, 17.3, 17.5, 18.2, 19.0, and 19.7, when measured with CuKα₁ radiation. In yet other embodiments, the single crystalline form is characterized by x-ray powder diffraction peaks at 2θ angles of 9.8, 11.7, 12.6, 15.5, 15.7, 15.9, 17.3, 17.5, 18.2, 19.0, and 19.7, when measured with CuKα₁ radiation. In still other embodiments, the single crystalline form is characterized by a x-ray powder diffraction pattern substantially similar to FIG. 1 when measured with CuKα₁ radiation. In yet other embodiments, the single crystalline form is characterized by having a stability transition in the range of 150° C. and 160° C. as observed with controlled temperature x-ray powder diffraction. In still other embodiments, the single crystalline form is characterized by a $T_{max}$ of 167±3° C. during an endothermic transition observed by differential scanning calorimetry using a scanning rate of 1° C./minute. In yet other embodiments, the single crystalline form is characterized by a weight loss observed by thermal gravimetric analysis corresponding to decomposition of the citrate salt beginning at 164° C.±3° C. In still other embodiments, single crystalline form gains about 0.8 moles of water per mole of citrate salt over a relative humidity change from 0% to 90% at 25° C. In still other embodiments, the single crystalline form is Form B. In yet other embodiments, the single crystalline form is characterized by at least one of the x-ray powder diffraction peaks at 2θ angles of 10.6, 11.6, 12.3, 14.8, 15.8, 16.1, 16.7, 18.8, 20.6, 21.7, and 24.5, when measured with CuKα₁ radiation. In still other embodiments, the single crystalline form is characterized by x-ray powder diffraction peaks at 2θ angles of 10.6, 11.6, 12.3, 14.8, 15.8, 16.1, 16.7, 18.8, 20.6, 21.7, and 24.5, when measured with CuKα₁ radiation. In still other embodiments, the single crystalline form is characterized by a x-ray powder diffraction pattern substantially similar to FIG. 6 when measured with CuKα₁ radiation. In yet other embodiments, the single crystalline form is characterized by having a stability transition between 170° C. and 180° C. as observed with controlled temperature x-ray powder diffraction. In still other embodiments, the single crystalline form is characterized by a $T_{max}$ of 179° C.±3° C. during an endothermic transition observed by differential scanning calorimetry using a scanning rate of 1° C./minute. In yet other embodiments, the single crystalline form is characterized by a weight loss observed by thermal gravimetric analysis corresponding to decomposition of the citrate salt beginning at 180° C.±3° C. In still other embodiments, the single crystalline form gains about 0.4 moles of water per mole of citrate salt over a relative humidity change from 0% to 90% at 25° C.

The present invention also provides a pharmaceutical composition comprising a pharmaceutically acceptable carrier or diluent; and a citrate salt of (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol, wherein at least 90% by weight of the citrate salt is crystalline. In some embodiments, at least 90% by weight of the citrate salt is a single crystalline form. In still other embodiments, at least 90% by weight of the citrate salt is other than Form A.

The present invention further provides a pharmaceutical composition comprising a pharmaceutically acceptable carrier or diluent; and a citrate salt of (S)-4-(4-Chloro-phenyl)-1-{3-[7-(1-hydroxy-1-methyl-ethyl)-11H-10-oxa-1-azadibenzo[a,d]cyclohepten-5-ylidene]-propyl}-3,3-dimethyl-piperidin-4-ol, the citrate salt being substantially Form A.

In yet other embodiments, the present invention also provides a pharmaceutical composition comprising a pharmaceutically acceptable carrier or diluent; and a citrate salt of (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol, the citrate salt being at least 10% by weight Form A.

In still other embodiments, the present invention provides a pharmaceutical composition comprising a pharmaceutically acceptable carrier or diluent; and a citrate salt of (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol, the citrate salt being substantially Form B. In yet other embodiments, the present invention provides a pharmaceutical composition comprising a pharmaceutically acceptable carrier or diluent; and a citrate salt of (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol, the citrate salt being at least 10% by weight Form B.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Mack Publishing Co., a standard reference text in this field, discloses various carriers used in formulating pharmaceutical compositions and known techniques for the preparation thereof. Except insofar as any conventional carrier medium is incompatible with the Citrate Salt, such as by producing any undesirable biological effect or otherwise interacting in a deleterious manner with any other component(s) of the pharmaceutical composition, its use is contemplated to be within the scope of this invention.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain stabilizers, pH modifiers, surfactants, bioavailability modifiers and combinations of these.

The quantity of active ingredient in the composition can range from about 0.1% to about 99.9% by weight, or about 20% to about 80% by weight. A unit dose preparation can contain from 1 mg to about 1000 mg active ingredient, preferably about 10 mg to about 100 mg active ingredient. The composition can, if desired, also contain other compatible therapeutic agents, including but not limited to, theophylline, β-adrenergic bronchodilators, corticosteroids, antihistamines, antiallergic agents, immunosuppressive agents (e.g., cyclosporine A, FK-506, prednisone, methylprednisolone), hormones (e.g., adrenocorticotropic hormone (ACTH)), cytokines (e.g., interferons (e.g., INFβ-1a, INFβ-1b)) and the like.

Treatment with Citrate Salt and Crystalline Forms Thereof

Another aspect of the invention relates to a method of treatment, including prophylactic and therapeutic treatments, of a disease associated with aberrant leukocyte recruitment and/or activation or mediated by chemokines or chemokine receptor function, including chronic inflammatory disorders characterized by the presence of RANTES, MIP-1α, MCP-2, MCP-3 and/or MCP-4 responsive T cells, monocytes and/or eosinophils, including but not limited to diseases such as arthritis (e.g., rheumatoid arthritis), atherosclerosis, arteriosclerosis, restenosis, ischemia/reperfusion injury, diabetes mellitus (e.g., type 1 diabetes mellitus), psoriasis, multiple sclerosis, inflammatory bowel diseases such as ulcerative colitis and Crohn's disease, rejection of transplanted organs and tissues (i.e., acute allograft rejection, chronic allograft rejection), graft versus host disease, chronic obstructive pulmonary disorder (COPD), as well as allergies and asthma. Other diseases associated with aberrant leukocyte recruitment and/or activation which can be treated (including prophylactic treatments) with the methods disclosed herein are inflammatory diseases associated with Human Immunodeficiency Virus (HIV) infection. Still other diseases associated with aberrant leukocyte recruitment and/or activation which can be treated (including prophylactic treatments) with the methods disclosed herein are cancer and osteolytic bone disorders. The method comprises administering to the subject in need of treatment an effective amount of a citrate salt of (S)-4-(4-Chloro-phenyl)-1-{3-[7-(1-hydroxy-1-methyl-ethyl)-11H-10-oxa-1-azadibenzo[a,d]cyclohepten-5-ylidene]-propyl}-3,3-dimethyl-piperidin-4-ol, as discussed herein. In some embodiments, the Citrate Salt is substantially crystalline. In other embodiments, at least 10% by weight of the Citrate Salt is crystalline. In yet other embodiments, at least 70% by weight of the citrate salt is at crystalline. In still other embodiments, at least 70% by weight of the Citrate Salt is a single crystalline form. In other embodiments, the single crystalline form is Form A. In still other embodiments, the single crystalline form is Form B. In still other embodiments, at least 70% by weight of the citrate salt is other than Form A.

In other embodiments, the method is useful for the treatment of rheumatoid arthritis, multiple sclerosis, atherosclerosis, inflammatory bowel disease, or psoriasis. In still other embodiments, the method is useful for the treatment of arteriosclerosis, restenosis, diabetes mellitus, colitis, or Crohn's disease. In yet other embodiments, the method is useful for the treatment of rejection of transplanted organs, graft versus host disease, allergies, asthma, or an inflammatory disease associated with Human Immunodeficiency Virus infection. In still other embodiments, the method is useful for the treatment of chronic obstructive pulmonary disorder (COPD).

In other embodiments the present invention provides a method for treating rheumatoid arthritis comprising administering to a subject in need thereof an effective amount of a citrate salt of (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol. In some embodiments, the Citrate Salt used for the treatment of rheumatoid arthritis has any one or more of the properties described above and herein for the Citrate Salt. In other embodiments, the Citrate Salt used for the treatment of rheumatoid arthritis has one or more of the following properties:
1. the Citrate Salt is substantially crystalline;
2. at least 70% by weight of the Citrate Salt is a single crystalline form;
3. at least 70% by weight of the Citrate Salt is a single crystalline form and the single crystalline form is Form A or Form B;
4. at least 70% by weight of the Citrate Salt is other than Form A.

In other embodiments, the present invention provides a method for treating multiple sclerosis comprising administering to a subject in need thereof an effective amount of a citrate salt of (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol. In some embodiments, the Citrate Salt used for the treatment of multiple sclerosis has any one or more of the properties described above and herein for the Citrate Salt. In other embodiments, the Citrate Salt used for the treatment of multiple sclerosis has one or more of the following properties:
1. the Citrate Salt is substantially crystalline;
2. at least 70% by weight of the Citrate Salt is a single crystalline form;
3. at least 70% by weight of the Citrate Salt is a single crystalline form and the single crystalline form is Form A or Form B;
4. at least 70% by weight of the Citrate Salt is other than Form A.

In yet other embodiments, the present invention provides a method for treating chronic obstructive pulmonary disorder (COPD) comprising administering to a subject in need thereof an effective amount of a citrate salt of (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol. In some embodiments, the Citrate Salt used for the treatment of chronic obstructive pulmonary disorder has any one or more of the properties described above and herein for the Citrate Salt. In other embodiments, the Citrate Salt used for the treatment of multiple sclerosis has one or more of the following properties:
1. the Citrate Salt is substantially crystalline;
2. at least 70% by weight of the Citrate Salt is a single crystalline form;
3. at least 70% by weight of the Citrate Salt is a single crystalline form and the single crystalline form is Form A or Form B;
4. at least 70% by weight of the Citrate Salt is other than Form A.

Other embodiments of the invention relate to methods of antagonizing a chemokine receptor, such as CCR1, in a subject comprising administering to the mammal the Citrate Salt as described herein.

According to the method, chemokine-mediated chemotaxis and/or activation of pro-inflammatory cells bearing receptors for chemokines can be inhibited. The amount of the Citrate Salt administered to the individual will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. Typically, an effective amount of the compound can range from about 0.1 mg per day to about 100 mg per day for an adult. Preferably, the dosage ranges from about 1 mg per day to about 100 mg per day. An antagonist of chemokine receptor function can also be administered in combination with one or more additional therapeutic agents, e.g. theophylline, β-adrenergic bronchodilators, corticosteroids, antihistamines, antiallergic agents, immunosuppressive agents (e.g., cyclosporin A, FK-506, prednisone, methylprednisolone), hormones (e.g., adrenocorticotropic hormone (ACTH)), cytokines (e.g., interferons (e.g., IFNβ-1a, IFNβ-1b)) and the like.

The Citrate Salt can be administered by any suitable route, including, for example, orally in capsules, suspensions or tablets or by parenteral administration. Parenteral administration can include, for example, systemic administration, such as by intramuscular, intravenous, subcutaneous, or intraperitoneal injection. The Citrate Salt can also be administered orally (e.g., dietary), transdermally, topically, by inhalation (e.g., intrabronchial, intranasal, oral inhalation or intranasal drops), or rectally, depending on the disease or condition to be treated. Oral or parenteral administration are preferred modes of administration.

The Citrate Salt can be administered to the individual in conjunction with an acceptable pharmaceutical or physiological carrier as part of a pharmaceutical composition for treatment the diseases discussed above. Formulation of a compound to be administered will vary according to the route of administration selected (e.g., solution, emulsion, capsule).

Preparation of Crystal Forms of the Citrate Salt

Some embodiments of the invention are directed toward a process of preparing a crystalline citrate salt of (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol. In one embodiment, citric acid is combined with a solution of (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol in a solvent to precipitate the crystalline citrate salt. The crystalline citrate salt is then isolated from the mixture using techniques known to those skilled in the art (e.g., filtration, evaporation, decanting, distillation (vacuum or at atmospheric pressure)).

Solvents that may be used to crystallize the Citrate Salt include ethanol, acetone, methanol, heptane, methyl ethyl ketone (MEK), water, toluene, isopropanol, n-propanol, tetrahydrofuran (THF), acetonitrile, dimethylsulfoxide (DMSO), dichlormethane, and combinations of one or more of the aforementioned solvents. The resulting crystalline Citrate Salt may include one or more single crystalline forms.

In particular embodiments, solvents such as acetone or toluene may be used to crystallize Form A of the Citrate Salt.

In other particular embodiments, solvents such as ethanol, methanol/heptane, MEK/water, n-propanol, isopropanol, isopropanol/water, acetonitrile/water, or methanol may be used to crystallize Form B. More particularly, Form B may be created by taking samples of Form A and exposing them to one of the solvent systems listed above. The particular conditions of the exposure are listed in Table 9.

In another particular embodiment of the invention, a mixture of Forms A and C is prepared by dissolving a sample of Form A in a mixture of THF and water at high temperature, and subsequently crystallizing the mixture of forms. Alternatively, a mixture of Forms A and C is prepared by exposing a sample of Forms A and B to THF at ambient temperature, and letting the crystal mature to Forms A and C.

In another particular embodiment of the invention, a mixture of Forms A and D is prepared by dissolving a sample of Form A in THF and slowly evaporating the solvent at ambient temperature and atmospheric pressure.

A particular embodiment of the invention is directed to preparing Form E by exposing a sample of Form A to water at ambient temperature, and allowing the sample to mature to Form E.

An alternate embodiment of the invention is directed to forming a crystalline Citrate Salt including Forms E, F, and G. A sample of the amorphous form of the Citrate Salt is exposed to water at ambient temperature. The sample subsequently matures to include a mixture of Forms E, F, and G.

A preferred embodiment of the invention is a process of preparing Form A of the citrate salt of (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol. The process comprises combining citric acid and a solution of (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol in acetone to precipitate the crystalline citrate salt. The salt is subsequently isolated from the combination. The mixture is typically held at a temperature between 30° C. and 40° C. during the precipitation, but other suitable temperatures can also be used. The temperature may be held for at least 10 minutes. Typically, at least one equivalent of citric acid is used per equivalent of (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol; preferably 1.0 to 1.5 equivalents of the citric acid are used.

In another preferred embodiment of the invention, a process for preparing Form B of the Citrate Salt includes combining citric acid with the (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol in ethanol to precipitate the crystalline citrate salt, and isolating the salt subsequently. Processes in accord with embodiments of the invention may further include seeding the mixture for precipitation with crystals of the Citrate Salt. In a preferred related embodiment, the crystals are Form B of the Citrate Salt. The process is typically conducted between 18° C. and 22° C. while combining the elements of the mixture; other suitable temperatures may also be utilized. The temperature is typically held for at least 2 hours while the crystals precipitate. Typically, at least one equivalent of citric acid is used per equivalent of (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol.

Some embodiments of the invention are directed toward a mixture for crystallizing a citrate salt of (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol. The mixture comprises citric acid; (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol; and a crystallization medium.

A crystallization medium is a solvent or a solvent system (e.g., combination of solvents) in which the citric acid and (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol are soluble, but the crystalline Citrate Salt is insoluble or at most sparingly soluble. The solubility of the (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol and Citrate Salt depends upon the temperature of the mixture (i.e., the solubility being higher at higher temperature).

Examples of crystallization mediums include ethanol, acetone, methanol, heptane, methyl ethyl ketone (MEK), water, toluene, isopropanol, n-propanol, tetrahydrofuran (THF), acetonitrile, dimethylsulfoxide (DMSO), dichlormethane, and combinations of one or more of the aforementioned solvents. In a particular embodiment of the invention, the crystallization medium is ethanol; acetone; methanol; MEK; n-propanol; isopropanol; THF; toluene; acetonitrile; water; heptane; a mixture of methanol and heptane; a mixture of MEK and water; a mixture of acetonitrile and water; a mixture of isopropanol and water; or a mixture of THF and water. In another particular embodiment of the invention, the crystallization medium is acetone. In yet another particular embodiment of the invention, the crystallization medium is ethanol. In still another particular embodiment of the invention, the crystallization medium is any of the solvents/solvent systems used in Table 9 herein.

Mixtures for crystallizing a Citrate Salt may include one or more seeds of a crystal that are optionally slurried in a medium; a precipitation/crystallization aid; and/or being held at various times at various temperatures to aid crystallization of the Citrate Salt. Other additives, such as those used to enhance the rate of crystallization as recognized by those of ordinary skill, are also within the scope of the invention.

Though embodiments of the invention described herein refer specifically to the (S)-enantiomer of the compound 4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol, it is well understood to those of ordinary skill in the art that related embodiments of the invention include use of the (R)-enantiomer, a racemic mixture of the compound, and any fractional combination of the (R) and (S) enantiomers.

EXPERIMENTAL

Analytical Characterization of Samples of Crystalline Forms of the Citrate Salt

Crystalline forms of the Citrate Salt are characterized with the results from operating one or more analytical techniques on a sample of the crystalline form. Such techniques include various types of X-ray powder diffraction (XRPD), thermal gravimetric analysis (TGA), differential scanning calorimetry (DSC), dynamic vapor sorption measurements (DVS), and optical microscopy. For each of the polymorphs of the Citrate Salt, in accord with an embodiment of the invention, one or more of these analytical techniques are utilized to characterize the polymorph. The individual techniques are described below.

X-ray powder diffraction (XRPD) is performed on various samples of the Citrate Salt using one of three instruments. XRPD measurements with Instrument 1 utilize a Siemens-Bruker D5000 Matic powder diffractometer with a Bragg-Brentano (vertical θ-2θ configuration) parafocusing geometry. X-rays are produced from a sealed cobalt anode running at 40 kV and 30 mA. Two lines are typically emitted: $CuK\alpha_1$ ($\lambda=1.7890$ Å) and $CoK\alpha_2$ ($\lambda=1.7929$ Å). An iron β-filter limits the $CuK\alpha_1$ ($\lambda=1.6208$ Å) radiation to about 1% of the diffracted beam at the detector. The primary beam passes through a parallel plate collimator (0.2 mm Soller slits), then through a divergence slit (0.2 mm). Diffracted X-rays are detected with a Braun 50 M multichannel linear detector having a 10°-wide detection window in angle 2θ. Scans are performed from 1.5° to 50.0° in 2θ, the scan time being 10 to 40 seconds per degree in 2θ. The error in the 2θ locations are typically within ±0.10 degrees.

In Instrument 2, high resolution XRPD diagrams are obtained with a Philips Analytical X'Pert Pro MPD powder diffractometer utilizing the Bragg-Brentano (vertical θ-2θ configuration) parafocusing geometry coupled with a X'Celerator detector. A sealed copper anode X-ray tube, running at 45 kV and 40 mA, generates the impinging X-rays. An incident beam monochromator (Johansson type: a symmetrically cut curved germanium (111) crystal) produces pure $CuK\alpha_1$ radiation ($\lambda=1.54060$ Å). A thin layer of the product is deposited on a single-crystal silicon wafer, cut out according to Si(510) crystallographic orientation that, by systematic extinction, impedes any Bragg reflection. In order to bring more crystallites into the diffraction position, and thus reduce the influence of particle statistics on the measurements, a sample spinner is used. The spinner rotation speed is set at 1 revolution per second. The angular range extends from 3° to 40° or 50° in 2θ, with a 0.02° step size in 2θ. A counting time of 1250 to 3500 seconds per step is used. The error in the 2θ locations are typically within ±0.10 degrees.

Scans performed with Instrument 2 may be analyzed with the "Profile Fitting" module of the Diffrac-AT program furnished by the Bruker Corporation to determine the 2θ angular position of each of the observable lines. Comparison of full widths at half maximum of the lines provided by the module resolves peak overlapping, and reveals the presence or absence of another phase. The best solution, the highest figure of merit, given by the Accelrys company's "X-Cell" indexing program is subsequently optimized by Pawley refinement. The treatment accounts for the whole profile of the diagram, and not simply the position of the lines. The treatment seeks to reproduce the experimental diagram as closely as possible by utilizing the diffracted intensities as variables.

In Instrument 3, XRPD measurements are performed at different temperatures to elucidate the evolution of crystal structure with temperature. Tests are carried out with a Siemens-Bruker D5000 diffractometer equipped with the Bragg Brentano parafocusing (θ-θ) geometry and an Anton-Paar TTK temperature chamber. Measurements utilize dry nitrogen or nitrogen streams having a particular humidity. The instrument specifications are substantially similar to the Siemens-Bruker D5000 Matic instrument described above (Instrument 1). Temperature is allowed to rise at a rate of 0.05° C./sec. Scans are recorded under the following conditions: a 1.5 to 50.0 degree scan in angle 2θ, 10 to 20 seconds counting time per degree in 2θ. Data are acquired in isotherm mode when the requested temperature is reached.

Measurements utilizing thermal gravimetric analysis (TGA) are carried out on a T.A. instruments TGAQ500 analyzer. Mass calibration is performed with 10 and 100 mg certified masses. Temperature calibration is performed with Alumel® and nickel standards (Curie points of respectively 154° C. and 354° C.). Samples are exposed to a constant nitrogen stream of 60 ml/min, and temperature ranges from room temperature to 350° C. at a 5° C./min rate. The quantity of product tested is between 2 and 13 mg. The sample is deposited in an open aluminum sample pan, which is itself placed in a platinum pan. The temperatures identified from TGA scans of a particular sample are accurate to within ±3° C.

Differential scanning calorimetry (DSC) analyses are performed using a T.A Instruments Q1000 thermal analyser. Analyses are carried out using nitrogen purge gas flowing at an average rate of 50 ml/min. A mechanical compressor cools the system, and equilibrates the instruments being used at ambient temperature between analyses. The calorimeter is temperature calibrated with materials such as indium and lead (onset of melting temperatures of 156.6° C. and 327.5° C. respectively). Energy calibration is performed with a certified indium calibrator (melting enthalpy of 28.45 J/g), applying a heating rate of 5° C./min. The temperatures identified from DSC scans of a particular sample are accurate to within ±3° C.

The samples are submitted to the following experimental temperature programs: after the equilibration of the sample at 10° C., the specimens were heated from 10° C. to 210° C. (or 250° C. or 260° C.) at a rate of 1 to 50° C./min.

Modulated temperature differential scanning calorimetry (MTDSC) is also used since deconvolution of the total heat flow into reversing and non-reversing heat flows allows the transitions to be easily identified. The samples were submitted to the same experimental temperature program: after the equilibration of the sample at −5° C., the samples were heated through a modulated program from −5° C. to 210° C. at a rate of 1° C./min. On the basis of the classical recommendations, the set of MTDSC parameters chosen for analysing all specimens was amplitude of 0.5° C. and period of 80 seconds.

Experiments are performed using crimped aluminium sample pans or open pans in some cases. The quantity of product analysed is typically between 2 and 13 mg.

Simultaneous TGA and DSC measurements are carried out using a SETSYS thermal analysis system produced by the Setaram corporation. A liquid nitrogen cooling system makes it possible to work at temperatures below 20° C. The emitted gases, upon sample heating, are carried by a transfer capillary tube to a Pfeiffer mass spectrometer, the capillary tube heated to 150° C. The mass spectrometer can analyze molecular fragments at <<m/e>> ratios between 1 and 200 uma. A sample with a mass between 1 and 27 mg is contained in an open concave aluminum sample pan (75 μl, capacity) exposed to a nitrogen stream. The sample is heated at a rate of 1 or 5° C./min.

Water sorption measurements are performed on a DVS-1 automated gravimetric vapor sorption analyser (Surface Measurement Systems Ltd., London, UK). The DVS-1 measures the uptake and loss of vapor gravimetrically using a Cahn D200 recording ultra-microbalance with a mass resolution of ±0.1 The relative humidity around the sample is controlled by mixing saturated and dry carrier gas streams using mass flow controllers. The temperature is maintained within ±0.1° C. by enclosing the entire system in a temperature-controlled incubator. A sample size between 15 and 20 mg is used. In general, the error in % (w/w) identified in a tested sample is ±0.1% (w/w).

Two protocols are utilized to operate the DVS. In one protocol, a sample is dried at 0% relative humidity (RH) to remove any surface water present and establish a dry, baseline mass. Next, the sample is exposed to the following relative humidity profile: 0%, 10%, 20%, 30%, 40%, 50%, 60%, 70%, 80%, 90%, 80%, 70%, 60%, 50%, 40%, 30%, 20%, 10%, 0%. In some instances, this profile is repeated, yielding 4 sets of data going up and down in RH. In another protocol, the sample is first equilibrated at 40% RH, then it was exposed to the following relative humidity profile: 40%, 50%, 60%, 70%, 80%, 90%, 100%, 90%, 80%, 70%, 60%, 50% 40% 30%, 20% 10%, 0%, 10%, 20%, 30%, 40%. At each stage, the sample mass is allowed to reach equilibrium before the relative humidity was increased or decreased; equilibrium is met when the time rate of change of mass did not exceed the value of 0.02%/min over a period of 30 or 60 minutes. If equilibrium state is not reached, the change in relative humidity took place automatically after 360 or 600 minutes. From the complete moisture sorption and desorption profile, an isotherm is calculated using the DVS Advanced Analysis Suite v3.6. All experiments were performed at 25° C.

Some embodiments of the invention are described more specifically by the use of the following examples, which are not intended in anyway to limit the scope of the present invention.

EXAMPLES

Example 1

Preparation of different polymorphs of the citrate salt of (S)-4-(4-Chloro-phenyl-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol Eight different crystalline forms of the Citrate Salt are prepared by crystallizing the citrate salt of (S)-4-(4-Chlorophenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol under a variety conditions. In each instance, Form A of the Citrate Salt is exposed to a solvent or solvent system under the particular conditions listed in Table 9 to generate the particular form(s) or amorphous Citrate Salt.

TABLE 9

Crystallization Conditions for Various Samples of the Citrate Salt

| Form(s) identified | Crystallization Conditions |
| --- | --- |
| B | Crystallization after dissolution at high temperature in ethanol. |
| B | Crystallization after dissolution at ambient temperature in methanol/heptane. |
| B | Crystallization after dissolution in MEK/water and azeotropic distillation (isolation in MEK). |
| B | Crystallization after dissolution in n-propanol, followed by a slow evaporation at ambient temperature. |
| A + C | Crystallization after dissolution at high temperature in THF/water. |
| A | Maturation in toluene at ambient temperature. |
| B | Crystallization after dissolution at high temperature in isopropanol. |
| B | Crystallization after dissolution at high temperature in isopropanol/water. |
| B | Crystallization after dissolution at high temperature in n-propanol. |
| A + D | Crystallization after dissolution THF, followed by a slow evaporation at ambient temperature and atmospheric pressure. |
| B | Crystallization after dissolution in azeotropic mixture acetonitrile/water. |
| Amorphous | Dissolution at ambient temperature in DMSO/water. |
| Amorphous | Dissolution in dichloromethane/methanol, followed by a quick evaporation at ambient temperature and low pressure. |
| Amorphous | Dissolution in THF/water and azeotropic distillation (isolation in water). |
| E + F + G | Maturation in water of the amorphous form at ambient temperature. |
| E | Maturation in water of Form A at ambient temperature. |
| B | Maturation in ethanol of Forms A and B at ambient temperature. |
| A + C | Maturation in THF of Forms A and B at ambient temperature. |
| B | Maturation in methanol of Forms A and B at ambient temperature. |

Example 2

Preparation of Form A of the citrate salt of (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol The tartrate of (S)-4-(4-Chloro-phenyl)-3,3-dimethylpiperidin-4-ol (7.5 kg) is mixed with 2-[5-(3-Bromo-propylidene)-5,11-dihydro-10-oxa-1-aza-dibenzo[a,d]cyclohepten-7-yl]-propan-2-ol (7.5 kg) and acetonitrile (90 liters) in a 250 liter glass-lined reactor inerted with nitrogen gas. The (S)-isomer is obtained by mixing 4-(4-Chloro-phenyl)-3,3-dimethylpiperidin-4-ol with an excess of (R,S)-tartaric acid to precipitate the (S) tartrate. The mixture is agitated with an impeller and cooled to between 0° C. and 5° C.

Water (23 liters) is charged to the vessel, followed by potassium carbonate (9.56). The solution is warmed to 20±5° C.; the temperature was maintained for at least 3 days. HPLC is utilized to follow the course of the reaction.

Water (45 liter) is added to the reactor. The total contents are concentrated using vacuum distillation at a pressure selected to maintain the temperature below 40° C. When the total contents volume is about 60 liters, the distillation is halted. The contents are brought to atmospheric pressure and a temperature between 20° C. to 30° C.

Next, dichloromethane 62 liters is charged to the reactor; the reactor is agitated for 15 minutes. The total volume is then allowed to sit for 15 minutes. The aqueous phase is subsequently discarded, and the organic phase returned to the reactor. The organic phase is twice washed with water (45 liters each time); each wash including agitating for 15 minutes, sitting for 15 minutes, and discarding the upper aqueous phase.

Di-tert-butyl dicarbonate (0.12 kg.) in dichloromethane (4 liters) is added to the reactor. The doseur is rinsed with 4 liters of dichloromethane. The solution is maintained at 20° C. for 10-20 minutes. The solution is analyzed for the presence of the tartrate of (S)-4-(4-Chloro-phenyl)-3,3-dimethylpiperidin-4-ol. If the tartrate is still present, di-tert-butyl dicarbonate was added in a 2:1 ratio molar ratio with the remaining tartrate. In this particular instance, more di-tert butyl dicarbonate (0.12 kg) in dichloromethane (4 liter) was required.

The contents of the reactor are again concentrated by vacuum distillation, maintaining the temperature at or below 40° C., until the residual volume is about 40 liters. The remaining contents are brought to a temperature between 20° C. and 30° C., and atmospheric pressure.

Next, acetone (31 liters) is charged to the reactor. The reactor's contents are concentrated to 40 liters by vacuum distillation while maintaining the temperature at or below 40° C. The remaining volume is then brought to a temperature between 20° C. and 30° C., and atmospheric pressure. The solvent exchange with acetone is repeated three more times.

Next, acetone (58 liters) and an acetonic slurry of decolorizing carbon (L3S, 0.38 kg of carbon; 2 liters acetone) is added to the reactor. The mixture is held for one hour at 20±5° C. The solution is filtered through a 0.22 um solvex-type filter, the filtrate being sent to a 160 liter reactor.

Citric acid (3.68 kg) and acetone (24 liters) are charged to the 250 liter reactor. The mixture is agitated at 20±5° C. until a solution was formed. The contents are heated to 35° C., and then transferred to the 160 liter reactor. The temperature of the 160 liter reactor is maintained at 35±5° C. during the transfer. The product begins to crystallize during the transfer. The temperature of 35±5° C. is maintained for 10 to 20 minutes after the transfer is complete.

The crystals and solution dispersion is filtered (filter drier; cake: d=55 cm, h=13 cm; filter time 4 hours). The filter cake is twice washed with acetone (34 liters of acetone each wash; wash time 10 hours total). The product is dried in a filter drier (40±5° C./−0.99 bar, non-agitated, ca. 100 hours) to produce 10.42 kg product (75% yield), which assays to 99% (w/w) of the citrate salt of (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol.

Example 3

Preparation of Form B of the citrate salt of (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol The tartrate of (S)-4-(4-Chloro-phenyl)-3,3-dimethylpiperidin-4-ol (20 kg) is mixed with 2-[5-(3-Bromo-propylidene)-5,11-dihydro-10-oxa-1-aza-dibenzo[a,d]cyclohepten-7-yl]-propan-2-ol (20 kg) and acetonitrile (240 liters) in a 600 liter glass-lined reactor inerted with nitrogen gas. The mixture is agitated with an impeller and cooled to between 0° C. and 5° C.

Water (60 liters) is charged to the vessel, followed by addition of potassium carbonate 25.5 kg. The solution is warmed to 20±5° C.; the temperature was maintained for about 4 days. HPLC is utilized to follow the course of the reaction.

Water (120 liters) is added to the reactor. The total contents are concentrated using vacuum distillation at a pressure selected to maintain the temperature below 40° C. When the total volume is about 90 liters, the distillation is halted. The remaining volume is brought to a temperature between 20° C. and 30° C. and atmospheric pressure.

Next, dichloromethane (165 liters) is charged to the reactor; the reactor is then agitated for 15 minutes. The total volume is subsequently allowed to sit for 15 minutes. The aqueous phase is discarded, and the organic phase returned to the reactor. The organic phase is twice washed with water (120 liters each time); each wash including agitating for 15 minutes, sitting for 15 minutes, and discarding the upper aqueous phase.

The organic phase is analyzed for the presence of the tartrate of (S)-4-(4-Chloro-phenyl)-3,3-dimethylpiperidin-4-ol. Di-tert-butyl dicarbonate in dichloromethane is added to the reactor in an approximate amount of 2 moles of dicarbonate for each mole of tartrate remaining. In this particular instance, about 0.3 kg of dicarbonate is used with about 5 liters of dichloromethane. The doseur is rinsed with 5 liters of dichloromethane. The solution is maintained at 20° C. for 10 to 20 minutes. The solution is again analyzed for the presence of the tartrate. If the tartrate is still present, more di-tert-butyl dicarbonate in dichloromethane is added to the reactor in an amount of dicarbonate to tartrate of 2:1 on a molar basis.

The contents of the reactor are again concentrated by vacuum distillation, maintaining the temperature at or below 40° C., until the residual volume is about 90 liters. The remaining contents are brought to a temperature between 20° C. and 30° C., and atmospheric pressure.

Next, absolute ethanol (71 liters) is charged to the reactor. The reactor's contents are concentrated to 90 liters by vacuum distillation while maintaining the temperature at or below 40° C. The remaining volume is then brought to a temperature 20° C. and 30° C. between and atmospheric pressure. The solvent exchange with absolute ethanol is repeated two more times.

Next, ethanol (71 liters) and an ethanolic slurry of decolorizing carbon (L3S, 1.15 kg of carbon; ethanol, qsp) are added to the reactor. The mixture is held for one hour at 20±5° C. The solution is filtered through a 0.22 um solvex-type filter, the filtrate being sent to a 400 liter reactor.

Citric acid (9.85 kg) and ethanol (37 liters) are charged to a 100 liter hastelloy reactor. The mixture is agitated at 20±5° C. until a solution is formed, the citric acid solution being transferred to a drum subsequently. The citric acid solution (13 kg) is added to the 400 liter reactor containing the filtrate, while maintaining a temperature of 20±2° C. in the reactor. The reactor is seeded with a slurry of Form B crystals of the Citrate Salt made from a portion of the solution in the 400 liter reactor. The crystals are milled for 30 seconds in a Thurrax-type mixer in liquid from the 400 liter reactor. The seeded crystallization mixture is maintained for 30 minutes.

The remainder of the citric acid solution is transferred to the 400 liter reactor over a 2.5 to 3 hour time period, while maintaining the temperature in the reactor at 20±2° C. The product crystallized during this transfer. Any excess citric acid solution is rinsed into the reactor with 5 liters of ethanol.

The reactor is cooled to 0±2° C. over 30 minutes; this temperature is subsequently maintained for at least 1 hour. The suspension is subsequently filtered (Nutsch filter, filter time 1 hour) to produce a filter cake. The cake is twice rinsed with ethanol (55 liters each rinse; wash time ~36 hours total). The cake is dried in a tray drier (40±5° C./–0.99 bar, non-agitated, ca. 48 hours) to produce 27.3 kg. of product (73% yield), which assays to 97% (w/w) of the citrate salt of 4-(4-Chloro-phenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A process for preparing the Form A of a crystalline citrate salt of (S)-4-(4-Chloro-phenyl)-1-{3-[7-(1-hydroxy-1-methyl-ethyl)-11H-10-oxa-1-aza-dibenzo [a,d]cyclohepten-5-ylidene]-propyl}-3,3-dimethyl-piperidin-4-ol, comprising:
   a) combining citric acid with a solution of (S)-4-(4-Chloro-phenyl)-1-{3-[7-(1-hydroxy-1-methyl-ethyl)-11H-10-oxa-1-aza-dibenzo[a,d]cyclohepten-5-ylidene]propyl}-3,3-dimethyl-piperidin-4-ol in acetone to precipitate the crystalline citrate salt; and
   b) isolating the crystalline citrate salt.

2. The process of claim 1, wherein combining includes maintaining a temperature between 30° C. and 40° C. of combined citric acid and the solution of (S)-4-(4-Chloro-phenyl)-1-{3-[7-(1-hydroxy -1-methyl-ethyl)-11H-10-oxa-1-aza-dibenzo [a,d]cyclohepten-5-ylidene]-propyl}-3,3-dimethyl-piperidin-4-ol in acetone.

3. The process of claim 2, wherein the temperature between 30° C. and 40° C. is maintained for at least 10 minutes.

4. The process of claim 1, wherein at least 1 equivalent of the citric acid is used per equivalent of (S)-4-(4-Chloro-phenyl)-1-{3[7-(1-hydroxy-1-methyl-ethyl)-11H-10-oxa-1-aza-dibenzo[a,d]cyclohepten-5-ylidene]-propyl}-3,3-dimethyl-piperidin-4-ol.

5. A process for preparing the Form B of a crystalline citrate salt of (S)-4-(4-Chloro-phenyl)-1-{3-[7-(1-hydroxy -1-methyl-ethyl)-11H-10-oxa-1-aza-dibenzo[a, d]cyclohepten-5-ylidene]-propyl}-3,3-dimethyl-piperidin-4-ol, comprising:
   a) combining citric acid with a solution of (S)-4-(4-Chloro-phenyl)-1-{3[7-(1-hydroxy-1-methyl-ethyl)-11H-10-oxa-1-aza-dibenzo[a,d]cyclohepten-5-ylidene]-propyl}-3,3-dimethyl-piperidin-4-ol in ethanol to precipitate the crystalline citrate salt; and
   b) isolating the crystalline citrate salt.

6. The process of claim 5, wherein combining includes seeding with citrate salt crystals of Form B.

7. The process of claim 5, wherein combining includes maintaining a temperature between 18° C. and 22° C. of combined citric acid and the solution of (S)-4-(4-Chlorophenyl)-1-{3-[7-(1-hydroxy-1-methyl-ethyl)-11H-10-oxa-1-aza-dibenzo[a,d]cyclohepten-5-ylidene]-propyl}-3,3-dimethyl-piperidin-4-ol in ethanol.

8. The process of claim 7, wherein the temperature between 18° C. and 22° C. is maintained for at least 2 hours.

9. The process of claim 5, wherein at least 1 equivalent of the citric acid is used per equivalent of (S)-4-(4-Chloro-phenyl)-1-{3-[7-(1-hydroxy-1-methyl-ethyl)-11H-10-oxa-1-aza-dibenzo[a,d]cyclohepten-5-ylidene]-propyl-}3,3-dimethyl-piperidin-4-ol.

\* \* \* \* \*